(12) United States Patent
Johnson et al.

(10) Patent No.: US 10,106,789 B2
(45) Date of Patent: Oct. 23, 2018

(54) SYSTEM AND METHODS FOR MASSIVELY PARALLEL ANALYSIS OF NUCLEIC ACIDS IN SINGLE CELLS

(71) Applicant: GigaGen, Inc., South San Francisco, CA (US)

(72) Inventors: David Scott Johnson, San Francisco, CA (US); Everett Hurteau Meyer, Redwood City, CA (US)

(73) Assignee: GigaGen, Inc., South San Francisco, CA (US)

( * ) Notice: Subject to any disclaimer, the term of this patent is extended or adjusted under 35 U.S.C. 154(b) by 0 days.

(21) Appl. No.: 15/431,660

(22) Filed: Feb. 13, 2017

(65) Prior Publication Data

US 2017/0166889 A1   Jun. 15, 2017

Related U.S. Application Data

(60) Continuation of application No. 15/159,674, filed on May 19, 2016, now Pat. No. 9,695,474, which is a division of application No. 13/993,047, filed as application No. PCT/US2011/065600 on Dec. 16, 2011, now abandoned.

(60) Provisional application No. 61/459,600, filed on Dec. 16, 2010.

(51) Int. Cl.
| | | |
|---|---|---|
| *C12N 15/10* | (2006.01) | |
| *C12Q 1/68* | (2018.01) | |
| *C40B 50/06* | (2006.01) | |
| *C12Q 1/6888* | (2018.01) | |
| *C12Q 1/6874* | (2018.01) | |

(52) U.S. Cl.
CPC ..... *C12N 15/1065* (2013.01); *C12N 15/1075* (2013.01); *C12Q 1/6874* (2013.01); *C12Q 1/6888* (2013.01); *C40B 50/06* (2013.01)

(58) Field of Classification Search
None
See application file for complete search history.

(56) References Cited

U.S. PATENT DOCUMENTS

| | | | |
|---|---|---|---|
| 5,830,663 | A | 11/1998 | Embleton et al. |
| 6,013,445 | A | 1/2000 | Albrecht et al. |
| 6,858,412 | B2 | 2/2005 | Willis et al. |
| 7,749,697 | B2 | 7/2010 | Oleksiewicz et al. |
| 8,507,205 | B2 | 8/2013 | Faham et al. |
| 9,090,674 | B2 | 7/2015 | Reddy et al. |
| 9,388,465 | B2 | 7/2016 | Hindson et al. |
| 2005/0064421 | A1 | 3/2005 | Gehrmann et al. |
| 2005/0221357 | A1 | 10/2005 | Shannon et al. |
| 2006/0246477 | A1 | 11/2006 | Hermans et al. |
| 2007/0141048 | A1 | 6/2007 | Oleksiewicz et al. |
| 2009/0098555 | A1 | 4/2009 | Roth et al. |
| 2010/0151471 | A1 | 6/2010 | Faham et al. |
| 2010/0310558 | A1 | 12/2010 | Oleksiewicz et al. |
| 2013/0274117 | A1* | 10/2013 | Church et al. ....... C12Q 1/6869 506/4 |
| 2013/0296535 | A1 | 11/2013 | Church et al. |
| 2015/0031555 | A1 | 1/2015 | Johnson et al. |
| 2015/0141261 | A1 | 5/2015 | Hunicke-Smith et al. |
| 2015/0167078 | A1 | 6/2015 | Johnson et al. |

FOREIGN PATENT DOCUMENTS

| | | |
|---|---|---|
| EP | 1516929 A2 | 3/2005 |
| WO | WO 1993/003151 A1 | 2/1993 |
| WO | WO 2006/086406 | 8/2006 |
| WO | WO 2009/049889 A1 | 4/2009 |
| WO | WO 2010/126614 | 11/2010 |
| WO | WO 2011/139371 A1 | 11/2011 |
| WO | WO 2012/104851 A1 | 8/2012 |
| WO | WO 2013/109935 | 7/2013 |
| WO | WO 2013/112655 | 8/2013 |
| WO | WO 2013/188772 | 12/2013 |
| WO | WO 2014/004124 | 1/2014 |

OTHER PUBLICATIONS

Office Action for U.S. Appl. No. 15/462,763, dated Oct. 27, 2017, 9 Pages.

Atanassov, Ivan I. et al., A simple, flexible and efficient PCR-fusion/Gateway cloning procedure for gene fusion, site-directed mutagenesis, short sequence insertion and domain deletions and swaps, Plant Methods, 2009, vol. 5, No. 14, pp. I-11.

Bonarius, H., et al., "Monitoring the T-Cell Receptor Repertoire at Single-Clone Resolution," PLOS ONE, Public Library of Science, US, vol. 1 1, No. 1, Dec. 20, 2006, pp. E55 1-10.

Boyd, S., et al., "Measurement and Clinical Monitoring of Human Lymphocyte Clonality by Massively Parallel V-D-J Pyrosequencing," Science Translational Medicine, Dec. 23, 2009, vol. 1, Issue 12 12ra23, pp. 1-8.

Brouzes, E., et al., "Droplet microfluidic technology for single-cell high-throughput screening," PNAS, Aug. 25, 2009, vol. 106, No. 34, pp. 14195-14200.

Chial, H., "Tumor Suppressor (TS) genes and the two-hit hypothesis," Nature Education 1 (1):177, 6 Pages, [online] 2008 [retrieved on Jun. 26, 2015] retrieved from the Internet <URL:http://www.nature.com/scitable/nated/topicpage/Tumor-Suppressor-TS-Genes-and-the-Two-887>.

Communication pursuant to Article 94(3) EPC for European Patent Application No. EP 11848932.7, dated Mar. 13, 2015, 4 pages.

(Continued)

*Primary Examiner* — Kaijiang Zhang
(74) *Attorney, Agent, or Firm* — Fenwick & West LLP

(57) ABSTRACT

Methods and systems are provided for massively parallel genetic analysis of single cells in emulsion droplets or reaction containers. Genetic loci of interest are targeted in a single cell using a set of probes, and a fusion complex is formed by molecular linkage and amplification techniques. Methods are provided for high-throughput, massively parallel analysis of the fusion complex in a single cell in a population of at least 10,000 cells. Also provided are methods for tracing genetic information back to a cell using barcode sequences.

16 Claims, 31 Drawing Sheets

Specification includes a Sequence Listing.

(56) References Cited

OTHER PUBLICATIONS

Dongen, J., et al., Design and standardization of PCR primers and protocols for detection of clonal immunoglobulin and T-cell receptor gene recombinations in suspect lymphoproliferations: report of the BIOMED-2 Concerted Action BMHC-CT98-3936', Leukemia, 2003, vol. 17, No. 12, pp. 2257-2317.
Embleton, M.J., et al., "In-cell PCR from mRNA: amplifying and linking the rearranged immunoglobulin heavy and light chain V-genes within single cells," Nucleic Acids Research, 1992, vol. 20, No. 15, pp. 3831-3837.
Hardenbol, P., et al., "Highly Multiplexed molecular inversion probe genotyping: Over 10,000 targeted SNPs genotyped in a single tube assay," Genome Research, 2005, vol. 15, pp. 269-275.
Hardenbol, P., et al., "Multiplexed genotyping with sequence-tagged molecular inversion probes," Nature Biotechnology, Jun. 2003, vol. 21, No. 6, pp. 673-678.
Horton, R., et al., Engineering hybrid genes without the use of restriction enzymes: gene splicing by overlap extension, Gene, 1989, vol. 77, No. 1, pp. 61-68.
Horton, R., et al., "Gene splicing by overlap extension: tailor-made genes using the polymerase chain reaction", Biotechniques, 1990, Vol .8, No. 5, pp. 528-535.
HVIID, T.V., In-Cell PCR Method for Specific Genotyping of Genomic DNA from One Individual in a Mixture of Cells from Two Individuals: A Model Study with Specific Relevance to Prenatal Diagnosis Based on Fetal Cells in Maternal Blood, Clinical Chemistry, 2002, vol. 48, pp. 2115-2123.
Johnston, D., et al., "De novo discovery of a tissue-specific gene regulatory module in a chordate," Genome Research, 2005, vol. 15, pp. 1315-1324.
Johnston, K.P., et al., "Water-in-Carbon Dioxide Microemulsions: An Environment for Hydrophiles Including Proteins," Science, Feb. 2, 1996, vol. 271, pp. 624-626.
Kiss, M.M., et al., "High-Throughput Quantitative Polymerase Chain Reaction in Picoliter Droplets," Anal. Chem., 2005, vol. 80, pp. 8975-8981.
Maheswaran, S., et al., "Detection of Mutations in EGFR in Circulating Lung-Cancer Cells," The New England Journal of Medicine, 2008, vol. 359, pp. 366-377.
Markoulatos, P., et al., "Multiplex Polymerase Chain Reaction: A Practical Approach", Journal of Clinical Laboratory Analysis, 2002, vol. 16, pp. 47-51.
Monod, M.Y., et al., "IMGT/JunctionAnalysis: the first tool for the analysis of the immunoglobulin and T cell receptor complex V-J and V-D-J JUNCTIONs," Bioinformatics, 2004, vol. 20, pp. i379-i385.
Moskalev, E., et al., "Correction of PCR-bias in quantitative DNA methylation studies by means of cubic polynomial regression", Nucleic Acids Research, 2011, vol. 39, No. 11.
Nagrath, S., et al., "Isolation of rare circulating tumour cells in cancer patients by microchip technology," Nature, 2007, vol. 450, pp. 1235-1239.
PCT International Search Report and Written Opinion for PCT/US2013/022210, dated May 14, 2013, 10 Pages.
PCT International Search Report and Written Opinion for PCT/US2013/022843, dated May 13, 2013, 9 Pages.
PCT International Search Report and Written Opinion for PCT/US2013/045864, dated Mar. 14, 2014, 12 Pages.
PCT International Search Report and Written Opinion for PCT/US2013/045904, dated Sep. 5, 2013, 12 Pages.
PCT International Search Report and Written Opinion, Application No. PCT/US2011/065600, dated Apr. 9, 2012, 16 pages.
Porreca, G., et al., "Multiplex amplification of large sets of human exons," Nature Methods, Nov. 2007, vol. 4, No. 11, pp. 931-936.
Ravn, U., et al., "By-passing in vitro screening—next generation sequencing technologies applied to antibody display and in silico candidate selection," Nucleic Acids Research, 2010, vol. 38, No. 21, pp. 1-11, e193.
Reddy, S., et al., "Monoclonal antibodies isolated without screening by analyzing the variable-gene repertoire of plasma cells," Nature Biotechnology, Sep. 2010, vol. 28, No. 9, pp. 965-959.
Robins, H., et al., "Comprehensive assessment of T-cell receptor β-chain diversity in αβ cells," Blood, 2009, vol. 114, pp. 4099-4107.
Robins, H., et al., "Overlap and Effective Size of the Human CD8+ T Cell Receptor Repertoire," Science Translational Medicine, Sep. 1, 2010, vol. 2, Issue 47 47ra64, pp. 1-9.
Sandberg, Y., et al., "BIOMED-2 Multiplex Immunoglobulin/T-Cell Receptor Polymerase Chain Reaction Protocols Can Reliably Replace Southern Blot Analysis in routine Clonality Diagnostics," Journal of Molecular Diagnostics, Oct. 2005, vol. 7, No. 4, pp. 495-503.
Shigematsu, H., et al., "Clinical and Biological Features Associated With Epidermal Growth Factor Receptor Gene Mutations in Lung Cancers," Journal of the National Cancer Institute, 2005, vol. 97, pp. 339-346.
Supplementary European Search Report for European Patent Application No. EP 11848932.7, dated Apr. 11, 2014, 10 Pages.
Van Dongen, J.J.M., et al., "Design and standardization of PCR primers and protocols for detection of clonal immunoglobulin and T-cell receptor gene recombinations in suspect lymphoproliferations: Report of the BIOMED-2 Concerted Action BMH4-CT98-3936," Leukemia, 2003, vol. 17, pp. 2257-2317.
Venturi, V., et al., "A Mechanism for TCR Sharing between T Cell Subsets and Individuals Revealed by Pyrosequencing," The Journal of Immunology, 2011, pp. 4285-4294, vol. 186.
Venturi, V., et al., "Methods for comparing the diversity of samples of the T cell receptor repertoire," Journal of Immunological Methods, 2007, vol. 321, No. 1, pp. 182-195.
Wagner, A., et al., "Surveys of Gene Families Using Polymerase Chain Reaction: PCR Selection and PCR Drift", Systematic Biology, Jun. 1994, vol. 43, No. 2, pp. 250-261.
Wurch, T., et al., "A modified overlap extension PCR method to create chimeric genes in the absence of restriction enzymes", Biotechnology Techniques, Sep. 1998, vol. 12, No. 9, pp. 653-657.
Yang, L., et al., "Rapid production of gene replacement constructs and generation of a green fluorescent protein-tagged centromeric marker in Aspergillus nidulans", Eukaryotic Cell, 2004, vol. 3, No. 5, pp. 1359-1362.
Zagordi et al., "Error correction of next-generation sequencing data and reliable estimation of HIV quasispecies", Nucleic acids Research, Jul. 29, 2010, vol. 38, No. 21, pp. 7400-7409.
Zeng, Y., et al., High-Performance Single Cell Genetic Analysis Using Microfluidic Emulsion Generator Arrays, Anal. Chem., 2010, vol. 82, pp. 3183-3190.
United States Office Action, U.S. Appl. No. 15/159,674, dated Nov. 28, 2016, 22 pages.
Zheng, G., et al., "Massively parallel digital transcriptional profiling of single cells," 10x Genomics, Inc., Pleasanton, CA, USA, Jul. 26, 2016, 46 pages.
Zilionis, R., et al., "Single-cell barcoding and sequencing using droplet microfluidics," *Nature Protocols*, Dec. 8, 2016, vol. 12, No. 1, pp. 44-73.

* cited by examiner sequencing in bulk reverse emulsion and sequence major amplicon in bulk reverse emulsion and sequence major amplicons in bulk

SYSTEM AND METHODS FOR MASSIVELY PARALLEL ANALYSIS OF NUCLEIC ACIDS IN SINGLE CELLS

CROSS REFERENCE TO RELATED APPLICATIONS

This application is a continuation of U.S. application Ser. No. 15/159,674, filed May 19, 2016, which is a divisional of U.S. application Ser. No. 13/993,047, filed Jun. 10, 2013, which is a national stage entry of International Application No. PCT/US2011/065600, filed Dec. 16, 2011, which claims the benefit of U.S. Provisional Application No. 61/459,600, filed Dec. 16, 2010, the disclosures of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Feb. 15, 2017, is named 35792_US_CRF_Sequencelisting.txt and is 17,383 bytes in size.

BACKGROUND OF THE INVENTION

Field of the Invention

The invention relates to the fields of molecular biology and molecular diagnostics, and more specifically to methods for massively parallel genetic analysis of nucleic acids in single cells.

Description of the Related Art

Certain quantitative genetic analyses of biological tissues and organisms are best performed at the single cell level. However, single cells only contain picograms of genetic material. Conventional methods, such as polymerase chain reaction (PCR), RNA sequencing (Mortazavi et al., 2008 Nature Methods 5:621-8), chromatin immunoprecipitation sequencing (Johnson et al., 2007 Science 316:1497-502), or whole genome sequencing (Lander et al., 2001 Nature 409:860-921), require more genetic material than is found in a single cell and are usually performed with thousands to millions of cells. These techniques provide useful genetic information at the cell population level, but have serious limitations for understanding biology at the single cell level. Current biological tools also lack the capacity to assay genetic measurements in many single cells in parallel.

Conventional single cell techniques are slow, tedious, and limited in the quantity of cells that can be analyzed at once. For example, in pre-implantation genetic diagnosis (PGD), a single cell is removed from a cleavage stage human embryo for genome-wide analysis of genetic diseases (Johnson et al., 2010 Human Reproduction 25:1066-75). Applications such as PGD require time-consuming, hand-guided biopsy technology, and the largest studies include hundreds of single cells. In another example, genetic recombination between loci of interest can be measured in single sperm cells (Jiang et al., 2005 Nucleic Acids Research 33:e91), but a manual analysis of thousands of single sperm would be time-consuming and impractical.

An established method for single cell analysis is fluorescence-activated cell sorting (FACS). Single cells are diluted into reaction wells, and various genetic and molecular biology techniques can be performed in the wells, from whole genome amplification to single locus PCR assays. However, due to the physical limits of parallelization using reaction wells, FACS is only useful for analyzing hundreds of single cells, rather than hundreds of thousands of single cells.

Single cells can also be used as reaction compartments for performing various genetic analyses (Embleton et al., 1992 Nucleic Acids Research 20:3831-37; Hviid, 2002 Clinical Chemistry 48:2115-2123; U.S. Pat. No. 5,830,663). Single cells can be sorted in aqueous-in-oil microdroplet emulsions, and molecular analyses can be performed in the microdroplets (Johnston et al., 1996 Science 271:624-626; Brouzes et al., 2009 PNAS 106:14195-200; Kliss et al., 2008 Anal Chem 80:8975-81; Zeng et al., 2010 Anal Chem 82:3183-90). These single cell assays are limited to single cell PCR in emulsions, or in situ PCR in single fixed and permeabilized cells. Moreover, when analyzing large populations of cells, it is difficult to trace back each gene product to a single cell or subpopulations of cells.

Thus, there is a need for methods for high-throughput, massively parallel genetic characterization of single cells and methods for identifying the cell or subpopulation of cells that originated the genetic material.

SUMMARY OF THE INVENTION

Disclosed herein is a method for analyzing at least two nucleic acid sequences in a single cell contained within a population of at least 10,000 cells. The method includes providing a providing a first set of nucleic acid probes, the first set comprising a first probe comprising a sequence that is complementary to a first target nucleic acid subsequence, a second probe comprising a sequence that is complementary to a second subsequence of the first target nucleic acid and a second sequence that is complementary to an exogenous sequence, a third probe comprising the exogenous sequence and a sequence that is complementary to a first subsequence of a second target nucleic acid, and a fourth probe comprising a sequence that is complementary to a second subsequence of the second target nucleic acid sequence.

The method includes isolating the single cells with at least one set of nucleic acid probes; amplifying the first and second target nucleic acid sequences independently, wherein the first target nucleic acid sequence is amplified using the first probe and the second probe, and wherein the second target nucleic acid sequence is amplified using the third probe and the fourth probe; hybridizing the exogenous sequence to its complement; and amplifying the first target nucleic acid sequence, the second target nucleic acid sequence, and the exogenous sequence using the first and fourth probes, thereby generating a fused complex.

The method also provides performing a bulk sequencing reaction to generate sequence information for at least 100,000 fused complexes from at least 10,000 cells within the population of cells, wherein the sequence information is sufficient to co-localize the first target nucleic acid sequence and the second target nucleic acid sequence to a single cell from the population of at least 10,000 cells.

In one aspect, the single cell is isolated in an emulsion microdroplet. In another aspect, the single cell is isolated in a reaction container.

In one embodiment, the amplifying step includes performing a polymerase chain reaction, wherein the amplifying step comprises performing a polymerase chain reaction, and wherein the first and third probes are forward primers and the second and fourth probes are reverse primers for the polymerase chain reaction. In another embodiment, the amplifying step includes performing a polymerase chain reaction, wherein the first and third amplification primers are forward primers and the second and fourth amplification primers are reverse primers for the polymerase chain reaction. In some embodiments, the amplifying step comprises performing a ligase chain reaction. The amplifying step can include performing a polymerase chain reaction, a reverse-transcriptase polymerase chain reaction, a ligase chain reaction, or a ligase chain reaction followed by a polymerase chain reaction.

In another embodiment, the fused complex is circular. In some embodiments, the first or second target nucleic acid sequence is an RNA sequence. The first or second target nucleic acid sequence can also be a DNA sequence. In one embodiment, the first or second target nucleic acid sequence comprises a T-cell receptor sequence. In another embodiment, the first target nucleic sequence, the second target nucleic acid sequence or both target nucleic acid sequences comprises an immunoglobulin sequence. In other embodiments, the first target nucleic acid comprises a T-cell receptor sequence, and the second target nucleic sequence comprises a second molecule that is associated with immune cell function. In another embodiment, the first target nucleic acid sequence comprises an immunoglobulin sequence, and the second sequence comprises a second molecule associated with immune cell function. In one embodiment, the second molecule associated with immune cell function is selected from the group consisting of: interleukin-2 (IL-2), interleukin-4 (IL-4), interferon gamma (IFNγ), interleukin-10 (IL-10), interleukin-1 (IL-1), interleukin-13 (IL-13), interleukin-17 (IL-17), interleukin-18 (IL-18), tumor necrosis factor alpha (TNFα), tumor necrosis factor beta (TNFβ), T-box transcription factor 21 (TBX21), forkhead box P3 (FOXP3), cluster of differentiation 4 (CD4), cluster of differentiation 8 (CD8), cluster of differentiation 1d (CD1d), cluster of differentiation 161 (CD161), cluster of differentiation 3 (CD3), major histocompatibility complex (MHC), cluster of differentiation 19 (CD19), interleukin 7 receptor (IL-17 receptor), cluster of differentiation 10 (CD10), cluster of differentiation 20 (CD20), cluster of differentiation 22 (CD22), cluster of differentiation 34 (CD34), cluster of differentiation 27 (CD27), cluster of differentiation 5 (CD5), and cluster of differentiation 45 (CD45), cluster of differentiation 38 (CD38), cluster of differentiation 78 (CD78), interleukin-6 receptor, Interferon regulatory factor 4 (IRF4), cluster of differentiation 138 (CD138).

In an embodiment, the first or second target nucleic acid includes a rare gene sequence. In some embodiments, the rare gene sequence is present in fewer than 5% of the cells, fewer than 1% of the cells, or fewer than 0.1% of the cells. In one embodiment, the rare gene sequence results from a genetic mutation. In another embodiment, the genetic mutation is a somatic mutation. In an embodiment, the genetic mutation is a mutation in a gene selected from the group consisting of epidermal growth factor receptor (EGFR), phosphatase and tensin homolog (PTEN), tumor protein 53 (p53), MutS homolog 2 (MSH2), multiple endocrine neoplasia 1 (MEN1), adenomatous polyposis coli (APC), Fas receptor (FASR), retinoblastoma protein (Rb1), Janus kinase 2 (JAK2), (ETS)-like transcription factor 1 (ELK1), v-ets avian erythroblastosis virus E26 oncogene homolog 1 (ETS1), breast cancer 1 (BRCA1), breast cancer 2 (BRCA2), hepatocyte growth factor receptor (MET), ret protoco-oncogene (RET), V-erb-b2 erythroblastic leukemia viral oncogene homolog 2 (HER2), V-Ki-ras2 Kirsten rat sarcoma viral oncogene homolog (KRAS), B-cell lymphoma 2 (BCL2), V-myc myelocytomatosis viral oncogene homolog (MYC), neurofibromatosis type 2 gene (NF2), v-myb myeloblastosis viral oncogene homolog (MYB), and mutS homolog 6 (*E. coli*) (MSH6). In other embodiments, the mutation is associated with a disease, and in one embodiment, the disease is cancer. In some embodiments, the cancer is a cancer selected from the group consisting of lung carcinoma, non-small cell lung cancer, small cell lung cancer, uterine cancer, thyroid cancer, breast carcinoma, prostate carcinoma, pancreas carcinoma, colon carcinoma, lymphoma, Burkitt lymphoma, Hodgkin lymphoma, myeloid leukemia, leukemia, sarcoma, blastoma, melanoma, seminoma, brain cancer, glioma, glioblastoma, cerebellar astrocytoma, cutaneous T-cell lymphoma, gastric cancer, liver cancer, ependymona, laryngeal cancer, neck cancer, stomach cancer, kidney cancer, pancreatic cancer, bladder cancer, esophageal cancer, testicular cancer, medulloblastoma, vaginal cancer, ovarian cancer, cervical cancer, basal cell carcinoma, pituitary adenoma, rhabdomyosarcoma, or Kaposi sarcoma.

In addition, the method can include in certain embodiments fixing and permeabilizing the cells prior to performing the amplification step. The method can also include lysing the cells prior to performing the amplification step and quantifying the sequence information generated from the bulk sequencing reaction.

In some embodiments, the method for analyzing the single cell includes a single cell contained within a population of at least 25,000 cells, at least 50,000 cells, at least 75,000 cells, or at least 100,000 cells. In some embodiments, the single cell is a unique cell with respect to the remaining cells in the population. In other embodiments, the single cell is a representative of a subpopulation of cells within the population. The population can be considered in some embodiments to be the total number of cells analyzed in a method of the invention.

In one embodiment, performing the bulk sequencing reaction to generate sequence information is carried out for at least 1,000,000 fused complexes from at least 10,000 cells within the population of cells.

The method includes providing a second set of nucleic acid probes, the second set comprising a fifth probe comprising a sequence that is complementary to a third target nucleic acid subsequence, a sixth probe comprising a sequence that is complementary to a second subsequence of the third target nucleic acid sequence and a second sequence that is complementary to a second exogenous sequence, a seventh probe comprising the exogenous sequence and a sequence that is complementary to a first subsequence of a fourth target nucleic acid sequence, and an eighth probe comprising a sequence that is complementary to a second subsequence of the fourth target nucleic acid sequence.

The method also provides isolating the single cells with the first and second sets of nucleic acid probes; amplifying the third and fourth target nucleic acid sequences independently, wherein the third target nucleic acid sequence is amplified using the fifth probe and the sixth probe, and wherein the fourth target nucleic acid sequence is amplified using the seventh probe and the eighth probe; hybridizing the exogenous sequence to its complement; amplifying the third target nucleic acid sequence, the fourth target nucleic acid sequence and the exogenous sequence using the fifth and eighth probes, thereby generating a fused complex; and performing a bulk sequencing reaction to generate sequence information for at least 100,000 fused complexes from at least 10,000 cells within the population of cells, wherein the sequence information is sufficient to co-localize the first target nucleic acid sequence, the second target nucleic acid sequence, the third target nucleic acid sequence, and the fourth target nucleic acid sequence to a single cell from the population of at least 10,000 cells.

In some aspects, the first target nucleic acid sequence and the third target nucleic acid sequence are the same. In other aspects, the first target nucleic acid sequence and the third target nucleic acid sequence are different.

In other embodiments, the method includes providing N sets of nucleic acid probes, wherein each of the N sets comprise an $I_1$ probe comprising a sequence that is complementary to an $I_a$ target nucleic acid first subsequence, an $I_2$ probe comprising a sequence that is complementary to an $I_a$ target nucleic acid second subsequence and a second sequence that is complementary to an I exogenous sequence, an $I_3$ probe comprising the I exogenous sequence and a sequence that is complementary to an $I_b$ target nucleic acid first subsequence, and an $I_4$ probe comprising a sequence that is complementary to an $I_b$ target nucleic acid second subsequence, wherein I ranges from 1 to N The method also includes isolating the single cells with the N sets of nucleic acid probes; amplifying for all values of I, the $I_a$ and $I_b$ target nucleic acid sequences independently, wherein the $I_a$ target nucleic acid sequence is amplified using the $I_1$ probe and the $I_2$ probe and the $I_b$ target nucleic acid sequence is amplified using the $I_3$ probe and the $I_4$ probe; hybridizing the I exogenous sequence to its complement; amplifying for each I, the $I_a$ target sequence, the $I_b$ target sequence and the I exogenous sequence using the $I_1$ and $I_4$ probes, thereby generating N fused complexes; and performing a bulk sequencing reaction to generate sequence information for at least 100,000 fused complexes from at least 10,000 cells within the population of cells, wherein the sequence information is sufficient to co-localize the N $I_a$ target nucleic acid sequence and the $I_b$ target nucleic acid sequence to a single cell from the population of at least 10,000 cells.

In other embodiments, N is less than or equal to 10, less than or equal to 100, less than or equal to 1000, less than or equal to 10,000, less than or equal to 100,000 or N represents all of the polyadenylated transcripts in a cell.

In some embodiments the method includes introducing a unique barcode sequence comprising at least six nucleotides into each of the plurality of single cells, wherein each barcode sequence is selected from a pool of barcode sequences with greater than 1000-fold diversity in sequences. For each of the plurality of single cells, the method includes providing at least one set of nucleic acid probes. The method includes steps for analyzing at least two nucleic acid sequences in a single cell contained within a population of at least 10,000 cells, comprising isolating each of a plurality of single cells from a population of at least 10,000 cells in an emulsion microdroplet or a reaction container. The method includes introducing a unique barcode sequence comprising at least six nucleotides into each of the plurality of single cells, wherein each barcode sequence is selected from a pool of barcode sequences with greater than 1000-fold diversity in sequence.

For each of the plurality of single cells, the method provides at least one set of nucleic acid probes, the set comprising a first probe comprising a sequence that is complementary to a nucleic acid sequence that is located at the 5' end of the barcode sequence, a second probe comprising a sequence that is complementary to a nucleic acid sequence that is located at the 3' end of the barcode sequence and a second region of sequence that is complementary to a non-human, exogenous sequence, a third probe comprising a sequence that comprises the non-human, exogenous sequence and a sequence that is complementary to a first subsequence of a second target nucleic acid sequence, and a fourth probe comprising a sequence that is complementary to a second subsequence of the second target nucleic acid sequence.

The method continues by amplifying the first and second nucleic acid sequences independently, wherein the first target nucleic acid sequence is amplified using the first probe and the second probe, and wherein the second target nucleic acid sequence is amplified using the third probe and the fourth probe; hybridizing the exogenous sequence to its complement; amplifying the first target nucleic acid sequence, the second target nucleic acid sequence, and the exogenous sequence using the first and fourth probes; performing bulk sequencing of the fused complexes; and identifying a single cell for each of the fused complexes based on the barcode sequence.

In some embodiments, the barcode sequence is affixed to a bead or a solid surface. The bead or the solid surface can be isolated in the emulsion microdroplet or the reaction container.

In other embodiments, the method includes introducing a unique barcode sequence comprises fusing the emulsion microdroplet or a reaction container comprising the single cell with the emulsion microdroplet or a reaction container comprising the barcode sequence affixed to the bead or the solid surface. The second target nucleic acid sequence can be complementary to an RNA sequence. The second target nucleic acid sequence can be complementary to a DNA sequence.

In certain embodiments, amplifying comprises performing a polymerase chain reaction, performing a ligase chain reaction, or performing by ligase chain reaction followed by polymerase chain reaction.

In one embodiment, the single cell is contained within a population of at least 25,000 cells. In other embodiments, the single cell is contained within a population of at least 50,000 cells. The single cell can be contained within a population of at least 75,000 cells or within a population of at least 100,000 cells.

In certain embodiments, the method also includes quantifying the fused complexes. In other embodiments, the fused complexes are circular.

In one aspect, the method includes providing N sets of nucleic acid probes, wherein each of the N sets comprise an $I_1$ probe comprising a sequence that is complementary a first subsequence of a barcode sequence, an $I_2$ probe comprising a sequence that is complementary to a second subsequence of the barcode sequence and a second sequence that is complementary to an I exogenous sequence, an $I_3$ probe comprising the I exogenous sequence and a sequence that is complementary to an $I_b$ target nucleic acid first subsequence, and an $I_4$ probe comprising a sequence that is complementary to an $I_b$ target nucleic acid second subsequence, wherein I ranges from 1 to N.

The method also provides isolating the single cells with the N sets of nucleic acid probes; amplifying for all values of I, the barcode sequence and the $I_b$ target nucleic acid sequences independently, wherein the barcode sequence is amplified using the $I_1$ probe and the $I_2$ probe and the $I_b$ target nucleic acid sequence is amplified using the $I_3$ probe and the $I_4$ probe; hybridizing the I exogenous sequence to its complement; amplifying for each I, the barcode sequence, the $I_b$ target sequence and the I exogenous sequence using the $I_1$ and $I_4$ probes, thereby generating N fused complexes; and performing a bulk sequencing reaction to generate sequence information for at least 100,000 fused complexes from at least 10,000 cells within the population of cells, wherein the sequence information is sufficient to co-localize the barcode sequence and the $I_b$ target nucleic acid sequence to a single cell from the population of at least 10,000 cells.

In other aspects, N is less than or equal to 10, less than or equal to 100, less than or equal to 1000, less than or equal to 100,000, or N represents all of the polyadenylated transcripts in a cell. In some embodiments, the barcode sequence is the same sequence for all N.

In other embodiments the invention also provides a method for introducing said barcode sequences into reaction containers or emulsion microdroplets. The method includes providing a pool of unique barcode sequences, wherein each barcode sequence is linked to a selection resistance gene. The method also includes providing a population of single cells, transfecting the population of single cells with the pool of unique barcode sequences, selecting cells containing a unique barcode sequence and the selection resistance gene, and isolating each of the selected cells into reaction containers or emulsion microdroplets. The selection resistance gene can encode resistance to gentamycin, neomycin, hygromycin, or puromycin, for example.

BRIEF DESCRIPTION OF THE SEVERAL
VIEWS OF THE DRAWINGS

These and other features, aspects, and advantages of the present invention will become better understood with regard to the following description, and accompanying drawings, where:

FIG. 1A shows an example of sequence linkage in a single cell by intra-cellular multiprobe circularization of a molecular complex, according to one embodiment of the invention. Each probe has a region of complementarity to each of the target loci. The complex includes two nucleic acid probes (a and b) and two target nucleic acids (c and d). The single cell (e) can be contained in a reaction container or an emulsion droplet (j).

Figure 3:
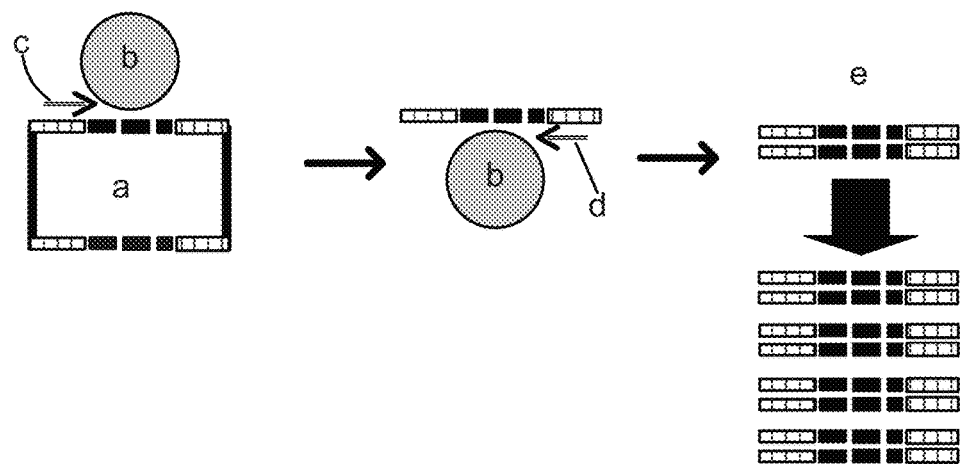

FIG. 3 illustrates an example of amplification of a circularized probe-target linkage complex (a) using a polymerase (b) and primers (c and d), according to one embodiment of the invention. The primers (c and d) are used to amplify the region of the circularized probe-target complex that is complementary to the target nucleic acid. Multiple copies (e) of a linear double-stranded polynucleic acid amplicon are generated and sequenced in bulk.

Figure 4:
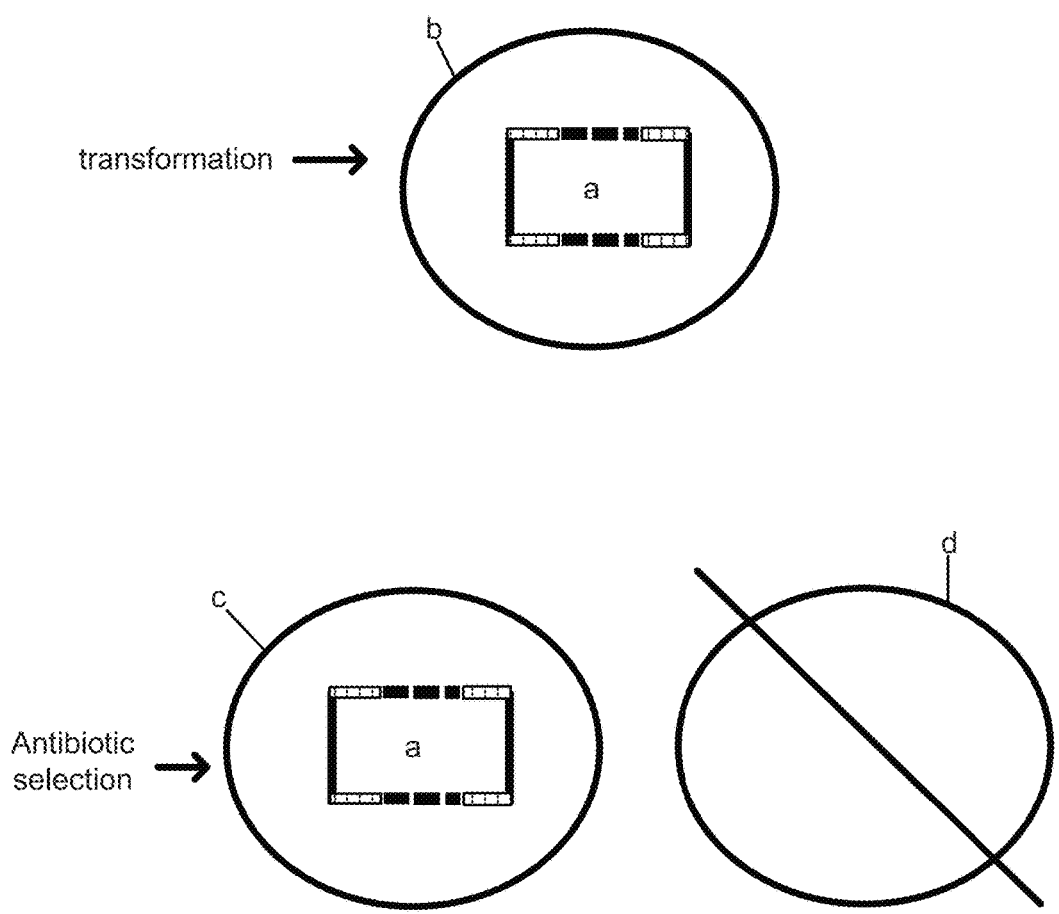

FIG. 4 illustrates an example of amplification of a circularized probe-target linkage complex (a) in a single cell (b), according to one embodiment of the invention. Amplification occurs by transformation into bacteria and subsequent selection with antibiotics. The amplicon (a) contains an antibiotic resistant gene and cells (c) that are transformed with the amplicon are selected in the presence of antibiotics. Cells without the circularized probe-target complex (d) are not selected.

Figure 5A:
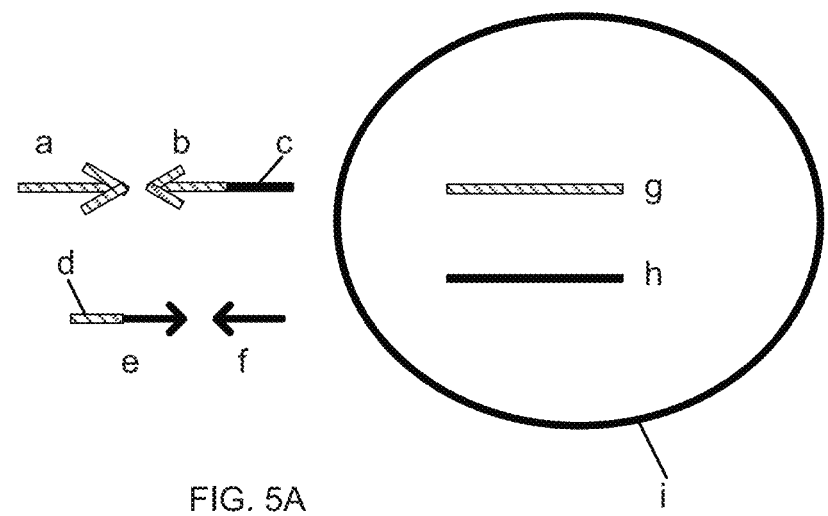

FIG. 5A shows an example of single cell sequence linkage by intracellular overlap extension polymerase chain reaction, according to one embodiment of the invention. A forward primer (a) targets one locus of a first target nucleic acid (g). A reverse primer (b) targets another locus of the first target nucleic acid (g) and has a region of complementarity (c) to a region (d) of the forward primer (e). The forward primer (e) has a region of complementarity to the second target nucleic acid (h) and the reverse primer (f) targets another region of the second target nucleic acid (h). The steps of FIG. 5 can be performed in a reaction container or an emulsion droplet.

Figure 5B:
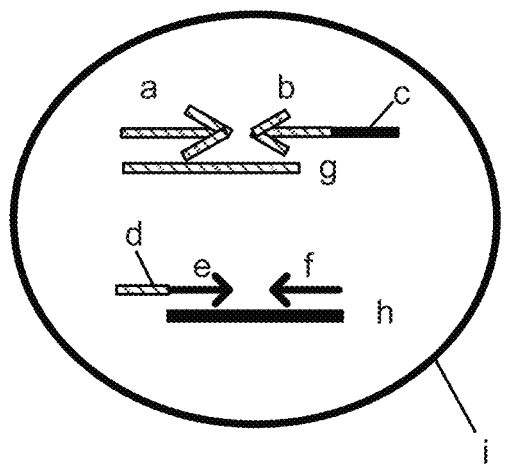

FIG. 5B illustrates an example of the hybridization of the probes (a, b, e and f) to respective target nucleic acids (g and h), according to one embodiment of the invention.

Figure 6A:
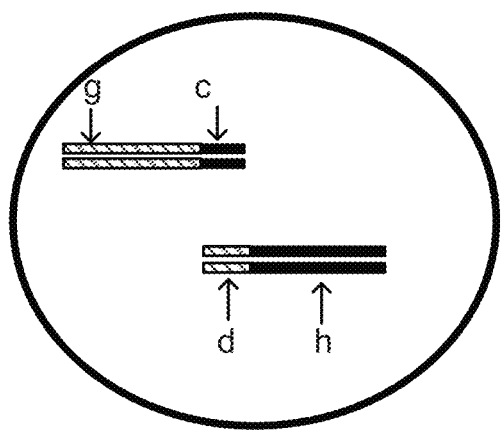
Figure 6B:
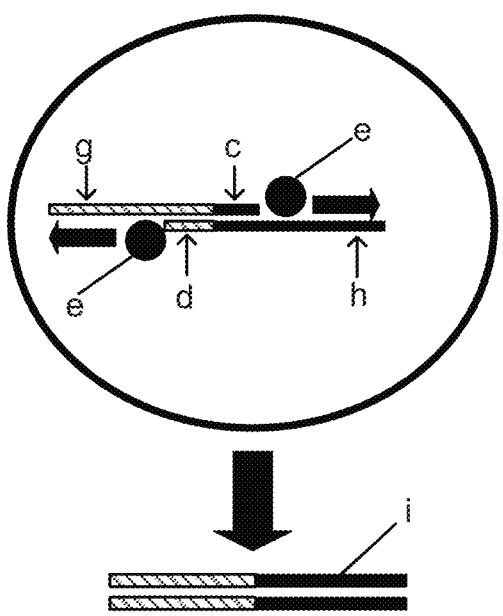

FIG. 6A illustrates an example of the complementary regions (c) and (d) between amplicons (g) and (h), according to one embodiment of the invention. FIG. 6B shows linkage amplification of the amplicons (g) and (h) using polymerase (e) to create a linked major amplicon (i). The end product is a library of "major amplicons" that include the linked amplicons (g) and (h), which can be sequenced in bulk. The steps of FIG. 6B can be performed in a reaction container or an emulsion droplet.

Figure 7A:
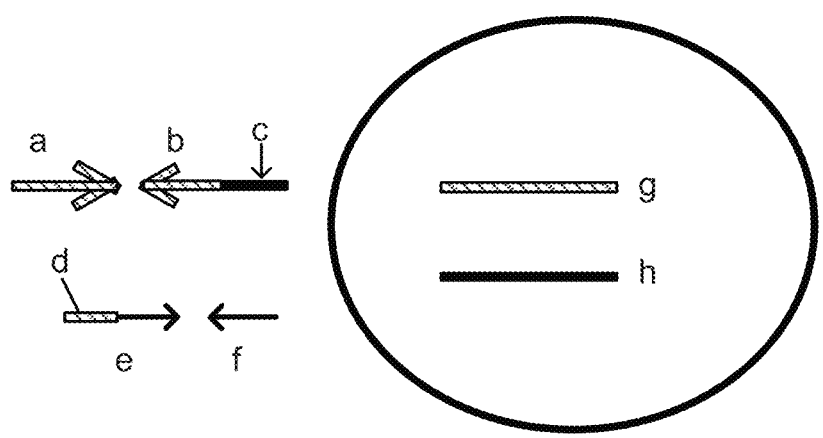
Figure 7B:
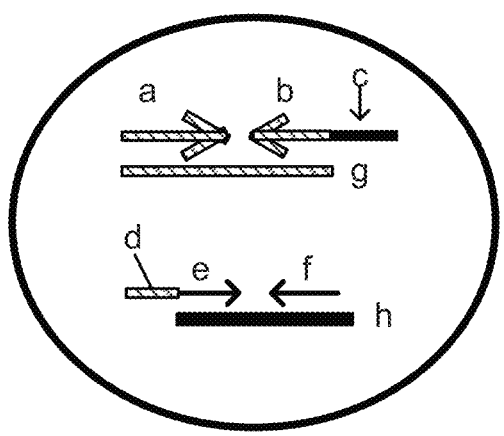

FIGS. 7A and 7B illustrate an example of single cell sequence linkage by intracellular ligase chain reaction combined with overlap extension polymerase chain reaction, according to one embodiment of the invention.

Figure 8A:
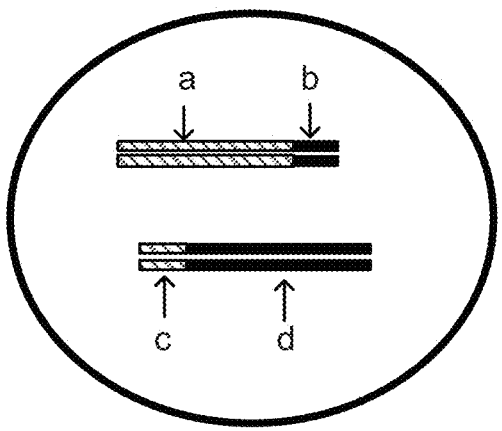
Figure 8B:
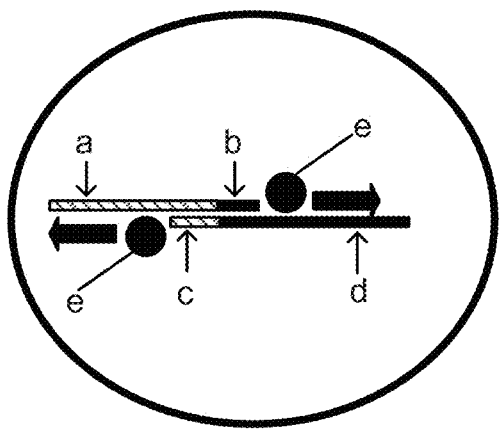

FIG. 8A shows an example of the complementary regions between amplicons (a) and (d), according to one embodiment of the invention. FIG. 8B shows linkage amplification of the amplicons using polymerase (e) to create a linked major amplicon. The steps of FIGS. 7A and 7B, and FIGS. 8A and 8B can be performed in a reaction container or an emulsion droplet.

Figure 9A:
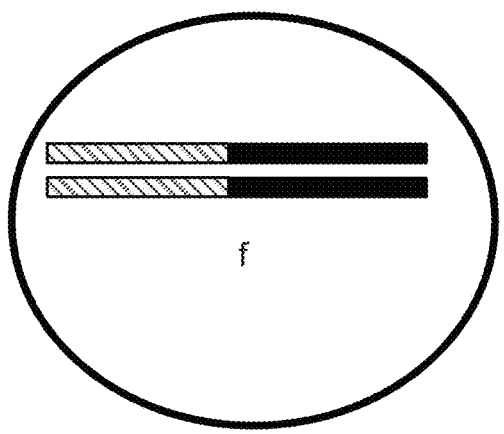
Figure 9B:

FIG. 9A shows an example of a linked amplicon (f), according to one embodiment of the invention. FIG. 9B shows the resulting amplicon produced from the steps shown in FIGS. 8A and 8B. The end product can be a library of "major amplicons" and are be sequenced in bulk.

Figure 10:
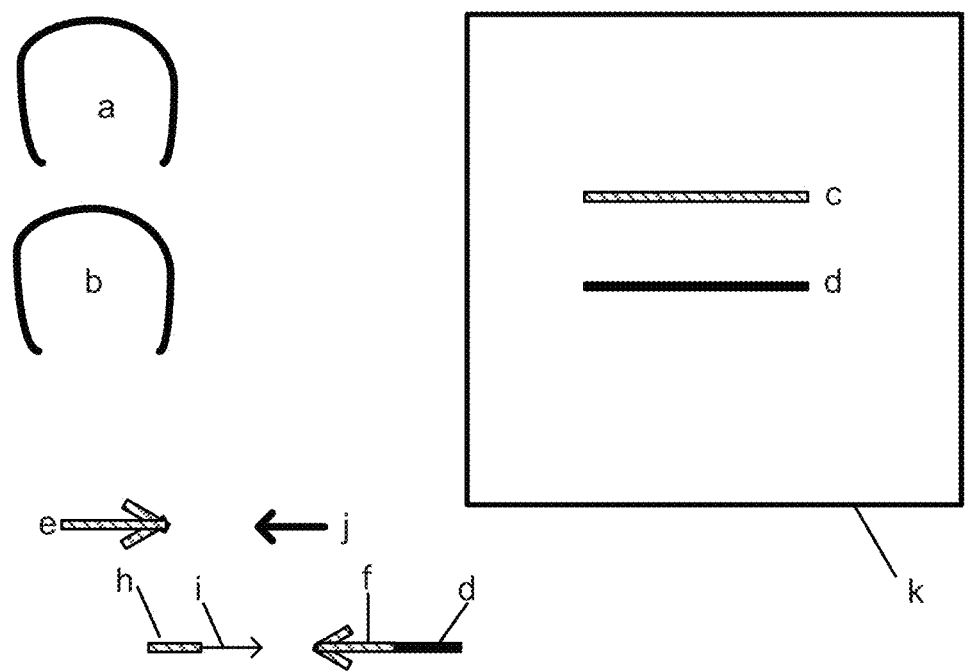

FIG. 10 illustrates an example of the components required for a single cell sequence linkage by padlock probes combined with overlap extension polymerase chain reaction, according to one embodiment of the invention.

Figure 11:
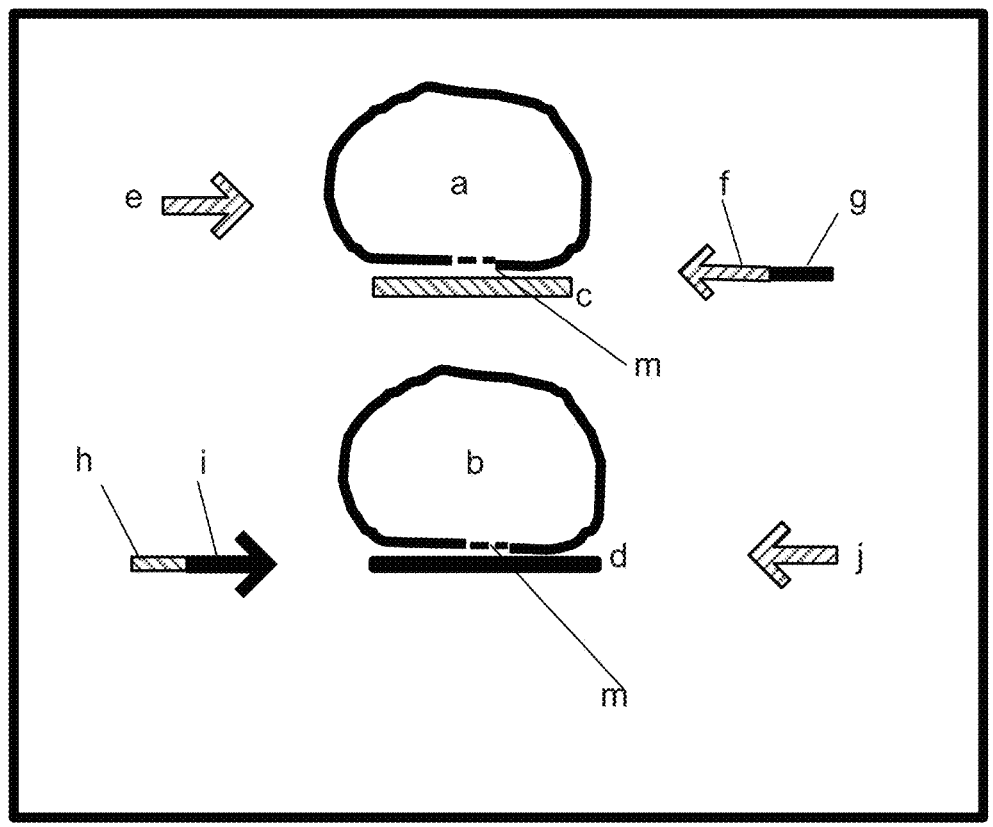

FIG. 11 shows the complementary regions between a first padlock probe (a) and the first target nucleic acid (c) and between a second padlock probe (b) and a second target nucleic acid (d) in a single cell, according to one embodiment of the invention.

Figure 12:
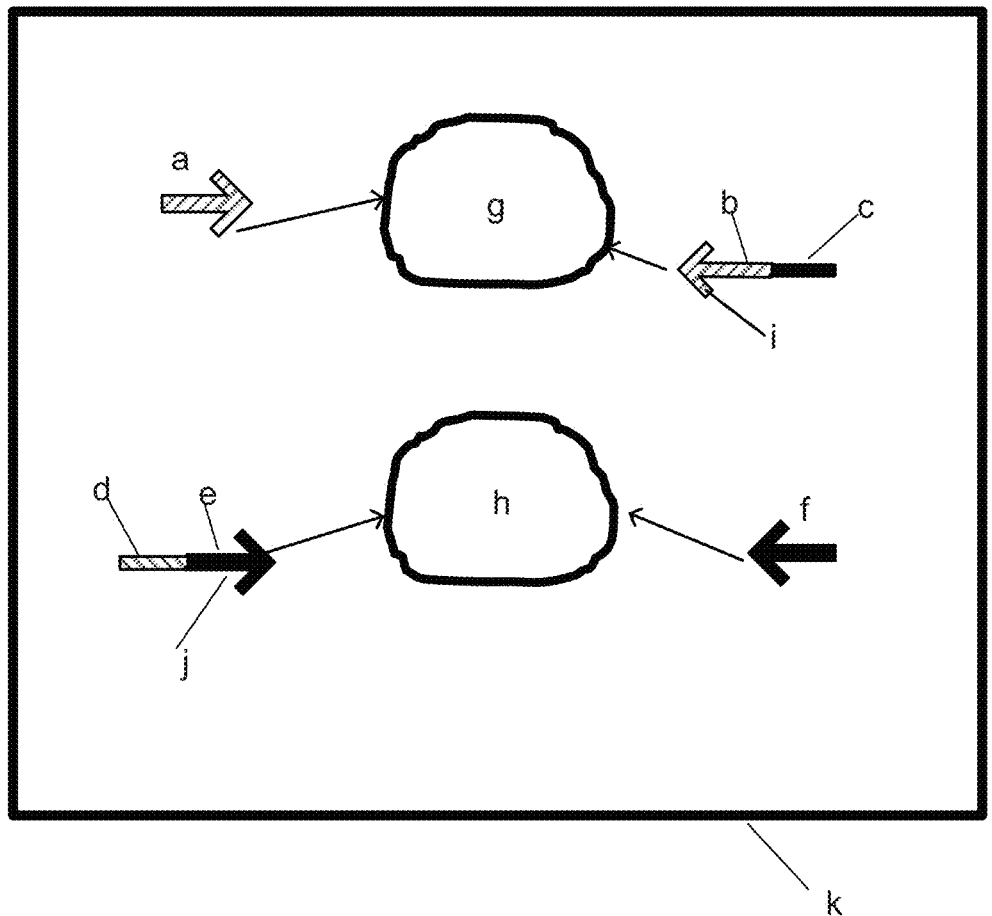

FIG. 12 illustrates the resulting circularized amplicons (g) and (h) and the primers that are used to amplify the circularized amplicons, according to one embodiment of the invention.

Figure 13:
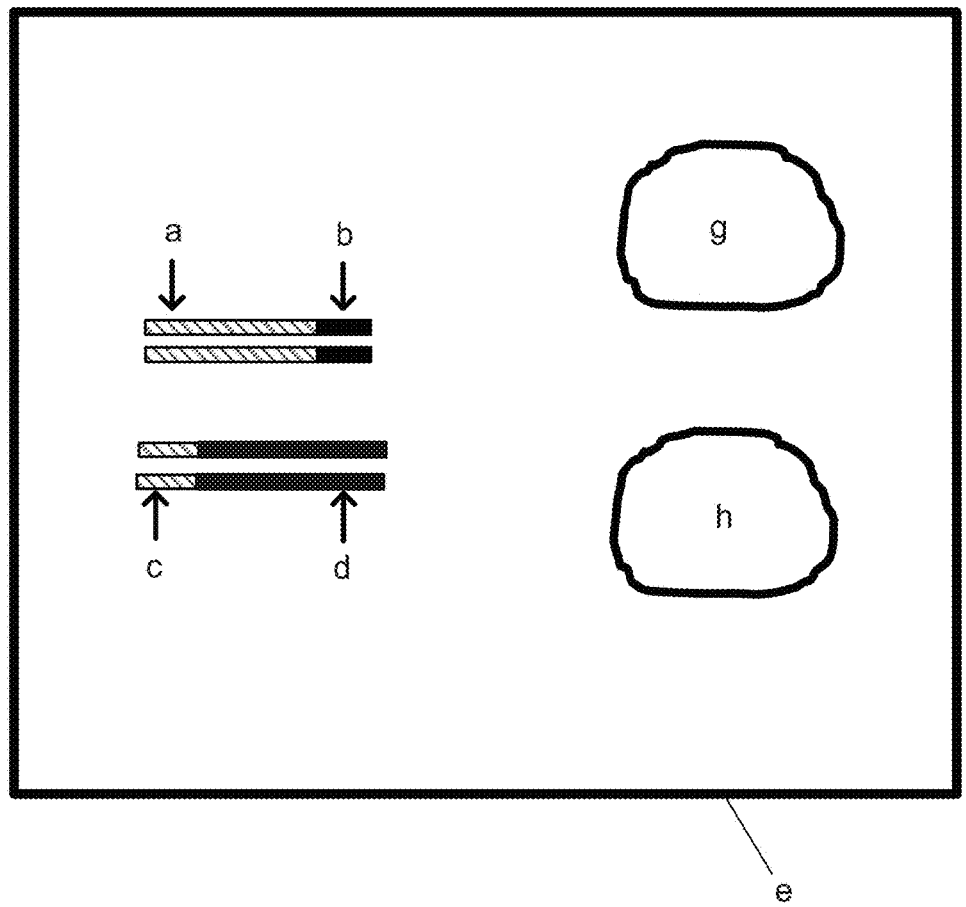

FIG. 13 shows an example of the resulting amplicons from amplification of the circular probes (g) and (h), according to one embodiment of the invention.

Figure 14:
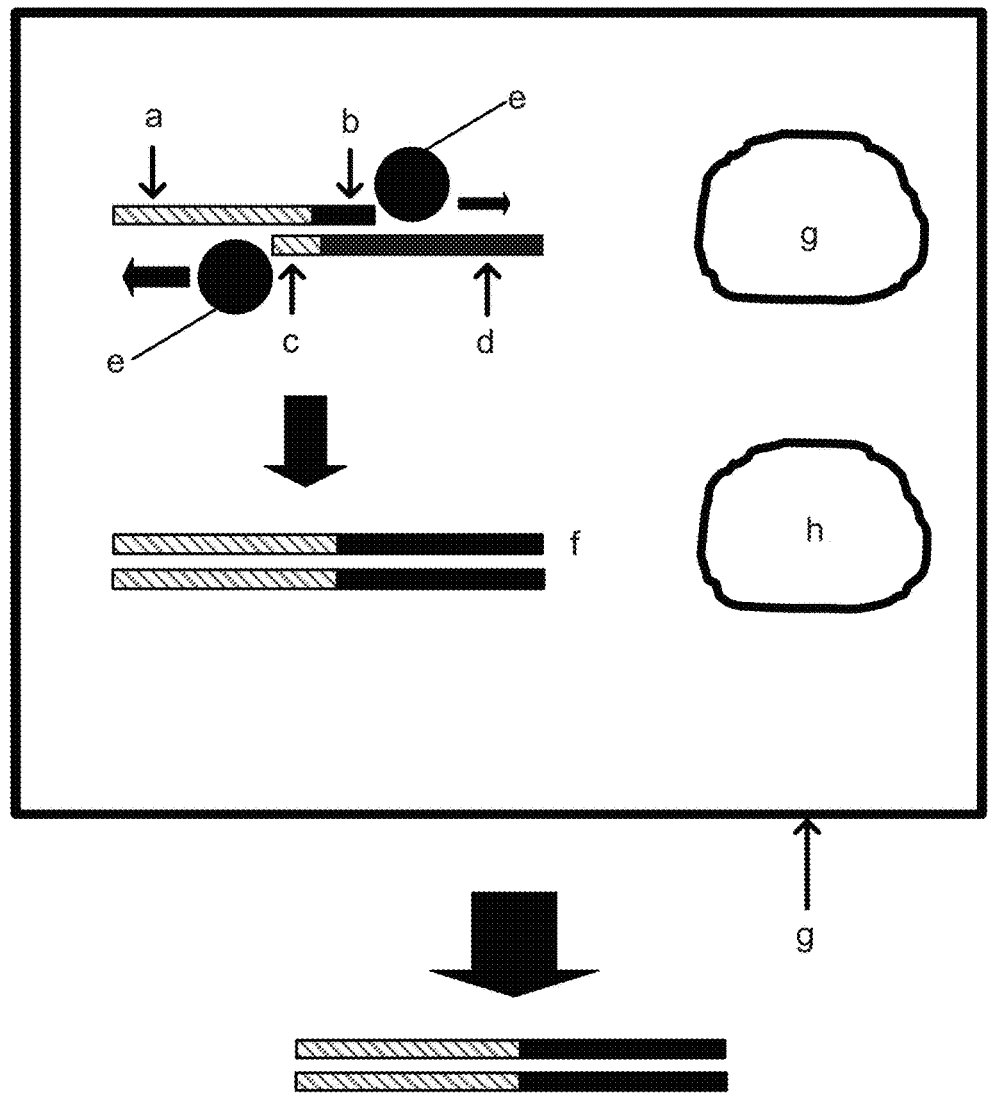

FIG. 14 shows an example of overlap extension PCR amplification of the amplicons using a polymerase (e), according to one embodiment of the invention.

Figure 15:
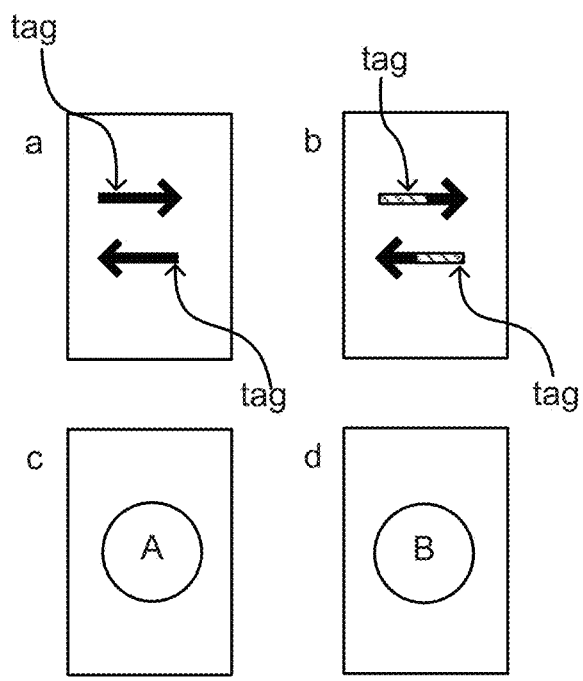

FIG. 15 illustrates an example of plasmid library deconvolution by barcoded tailed end (5'-end barcoded) polymerase chain reaction, which is followed by bulk sequencing and informatics, according to one embodiment of the invention. The barcode sequence can be traced back to a well and plate position, the barcode sequence can then be traced to a nucleic acid sequence, and the nucleic acid sequence is traced back to a well. Each of the primers in (a) and (b) have a 5'-end barcoded tag. The target nucleic acids in (c) and (d) are amplified using the primers in (a) and (b). The steps can be performed in enclosed containers or emulsion droplets, as shown in (c) and (d).

Figure 16:
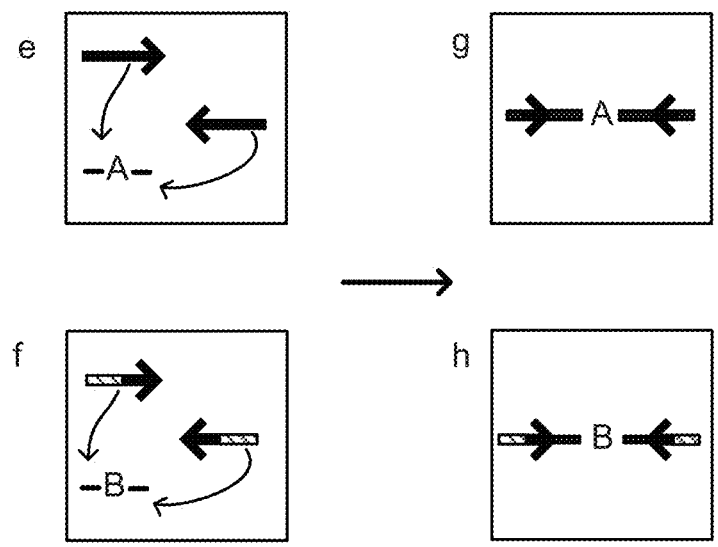

FIG. 16 shows an example of amplification (e, f) of two target nucleic acids (A and B) using primers that include barcode sequences, according to one embodiment of the invention. The resulting amplicons that include the barcode sequences are shown in (g) and (h).

Figure 17:
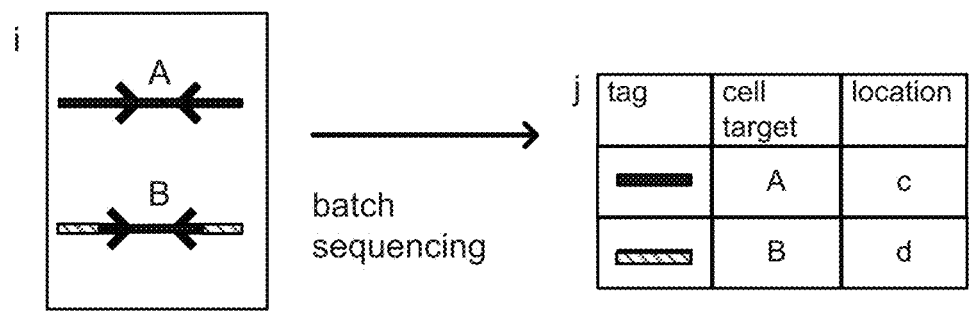

FIG. 17 shows a simplified example of tracing back a barcode sequence in an amplicon to a cell target (A or B), and tracing back the cell target to a physical location (c, d) (e.g., a well), according to one embodiment of the invention.

Figure 18:
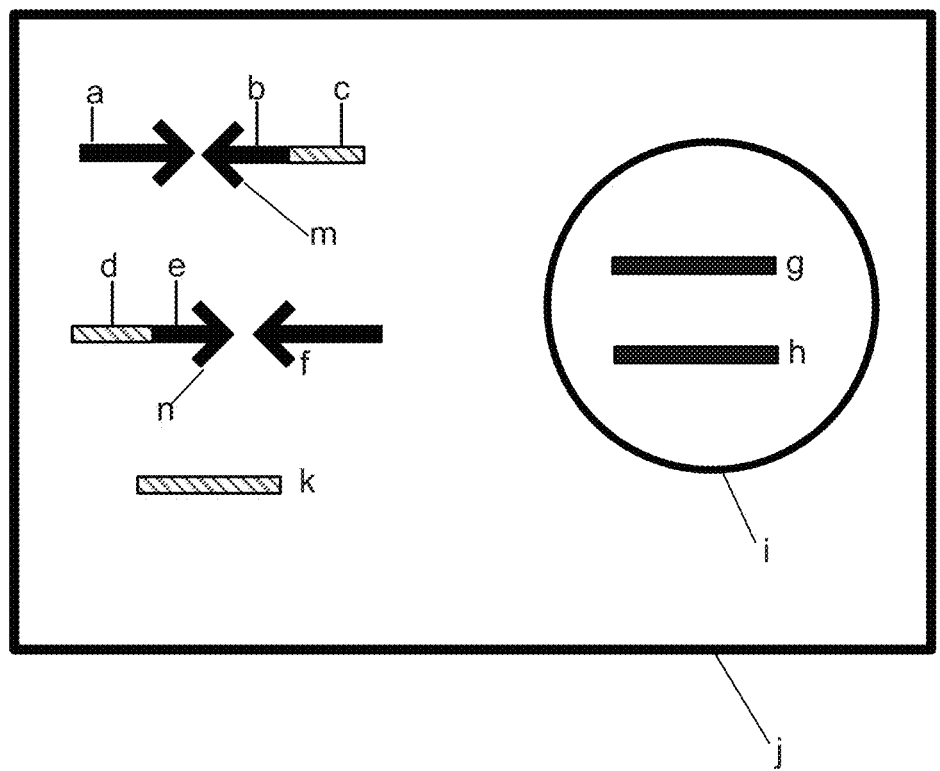

FIG. 18 illustrates molecular linkage between two transcripts (g and h) and a molecular barcode sequence (k), according to one embodiment of the invention.

Figure 19:
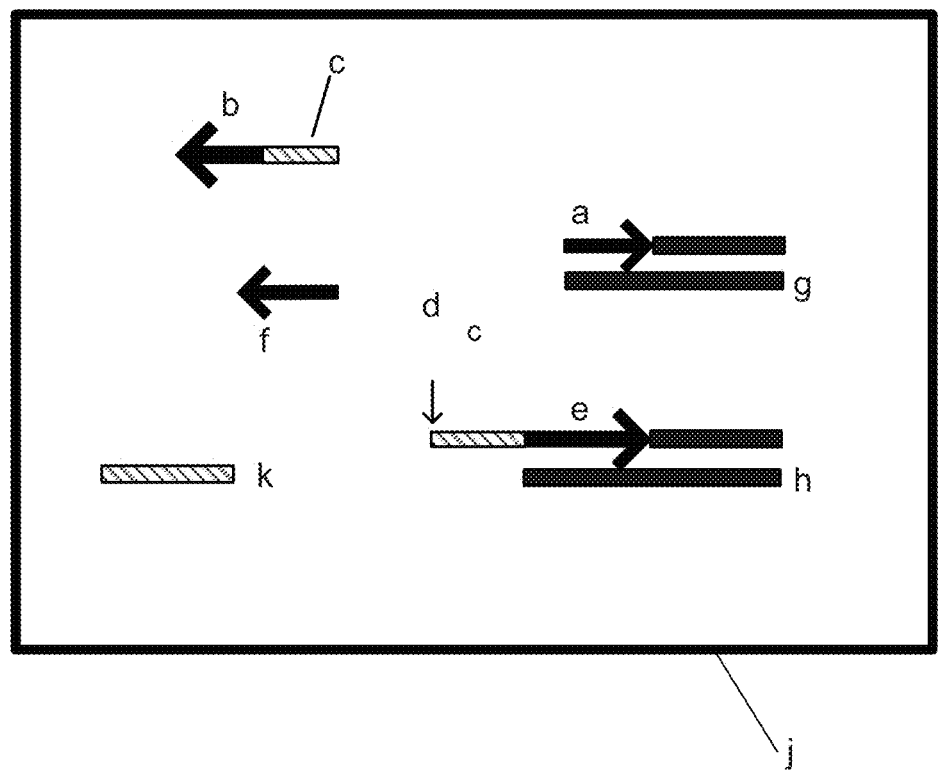

FIG. 19 shows an example of amplification of the target nucleic acids (g and h) using primers as shown, according to one embodiment of the invention.

Figure 20:
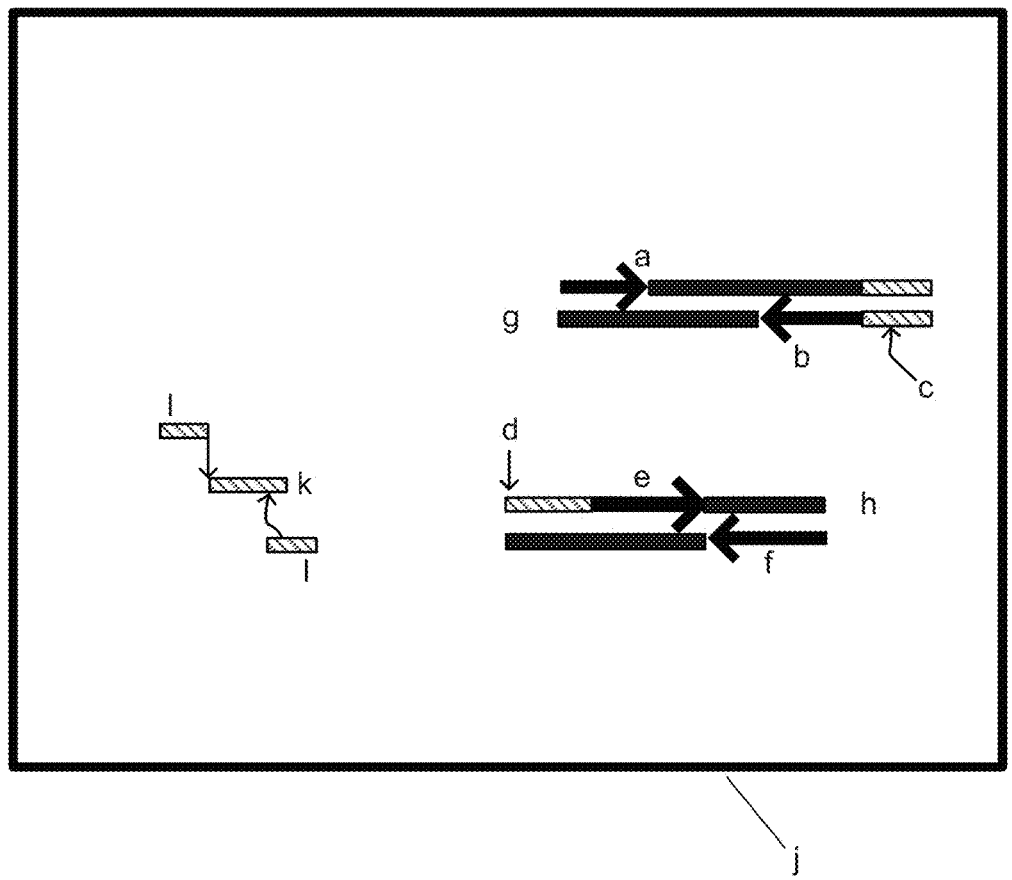

FIG. 20 shows an example of amplicons resulting after amplification of two target nucleic acids and a barcode sequence (k), according to one embodiment of the invention.

Figure 21:
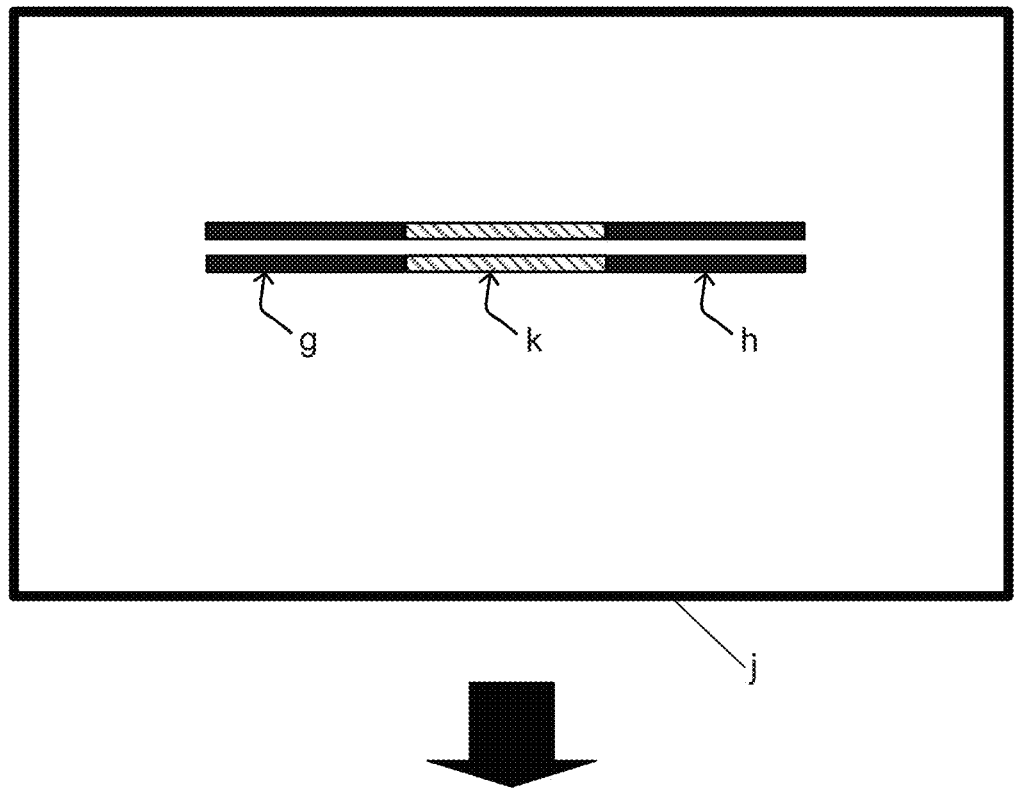

FIG. 21 illustrates a fused amplicon that includes sequences of two target nucleic acids (g and h) and a barcode sequence (k) inside an emulsion droplet or reaction container (j), according to one embodiment of the invention. The fused ("major") amplicon can be isolated by reverse emulsion and bulk sequenced.

Figure 22:
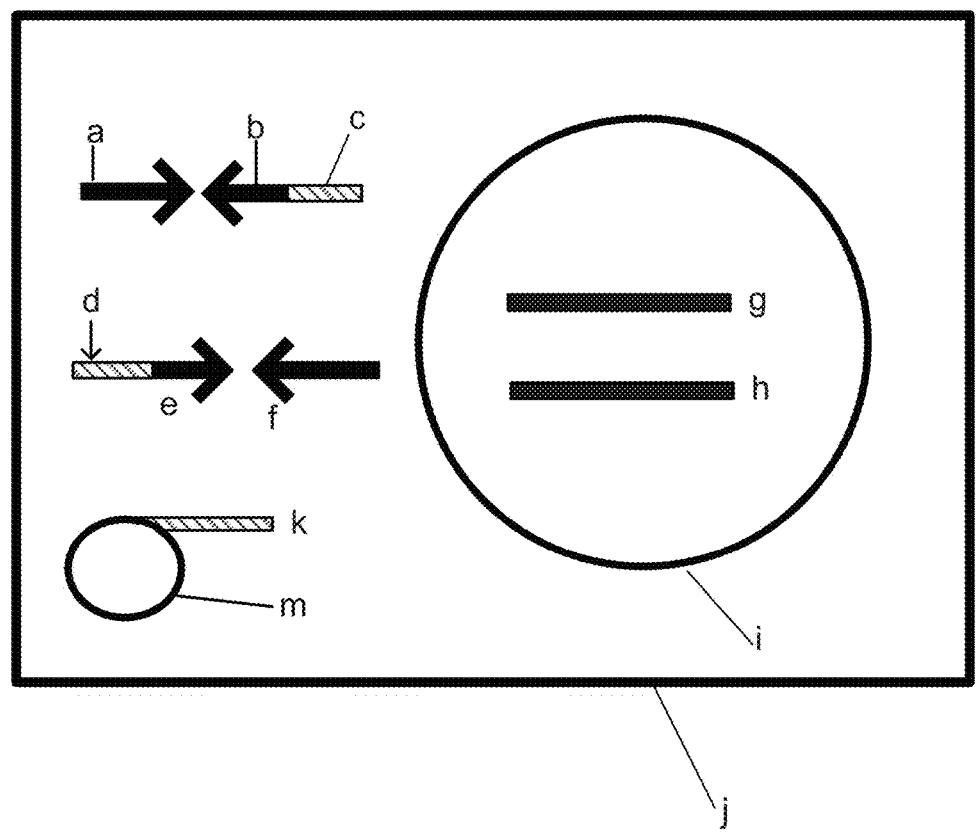

FIG. 22 is an example of molecular linkage between two transcripts (g and h) and a molecular barcode sequence (k) attached to a bead (m), according to one embodiment of the invention.

Figure 23:
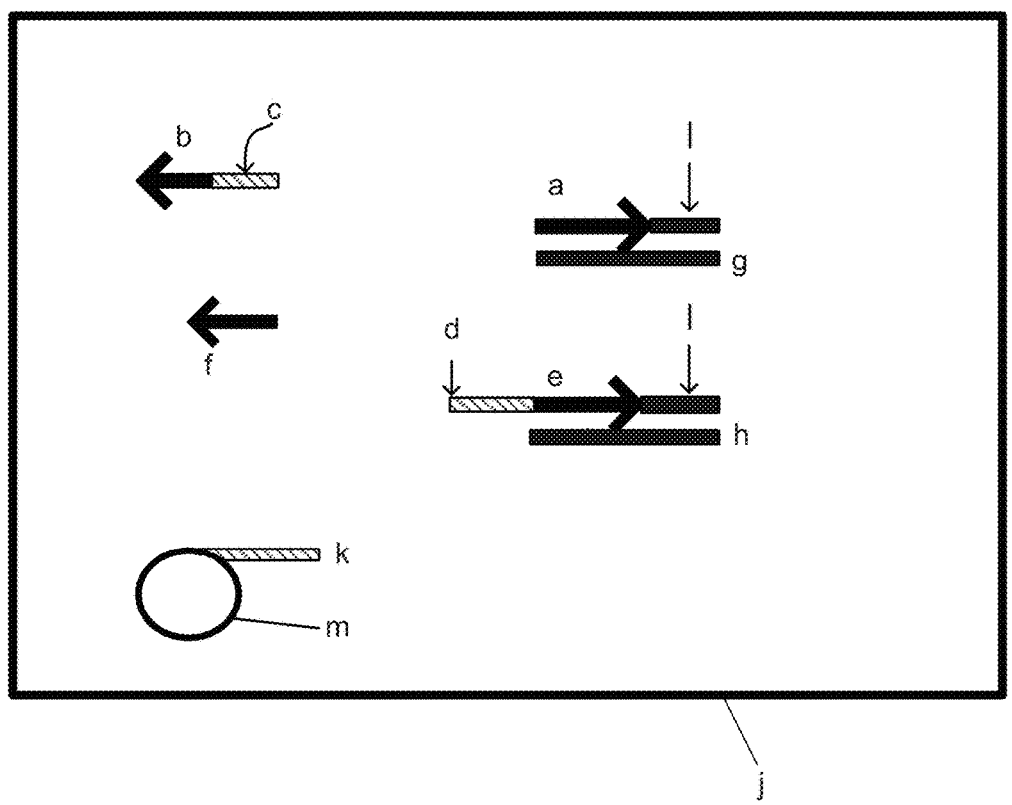

FIG. 23 illustrates the forward and reverse primers that are used in a molecular linkage between two transcripts (g and h) and a molecular barcode sequence (k) attached to a bead (m), according to one embodiment of the invention.

Figure 24:
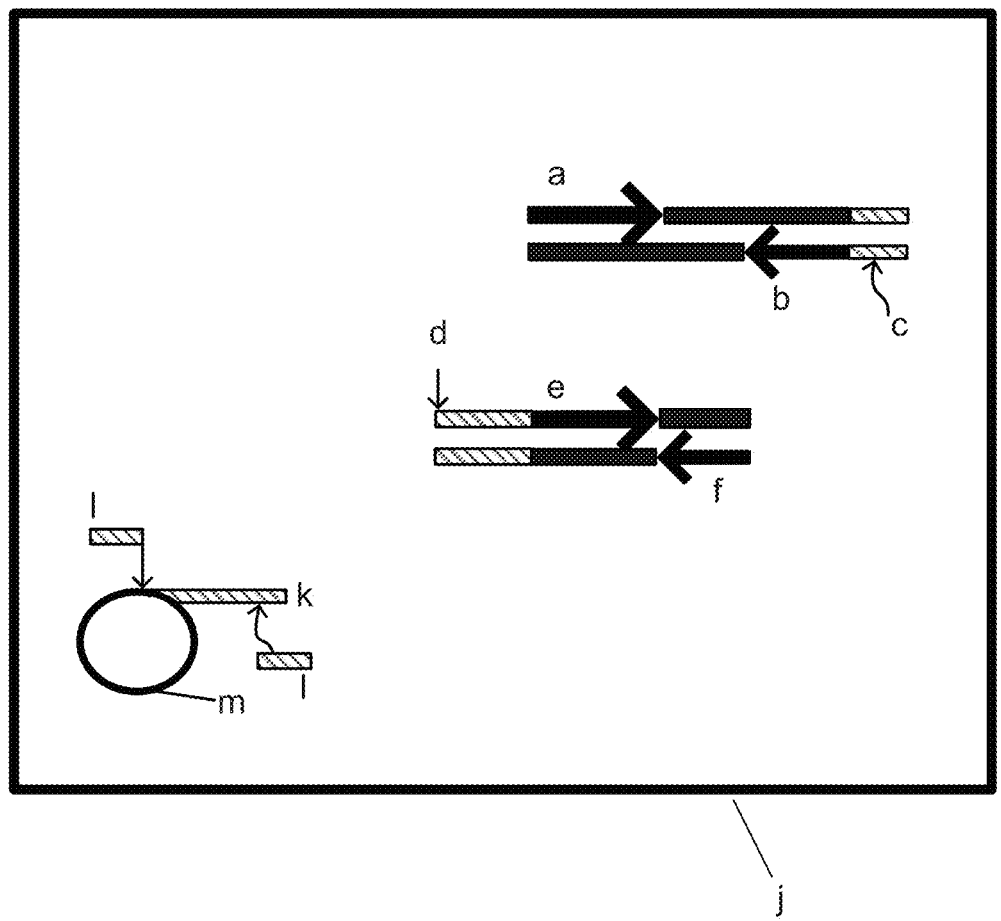

FIG. 24 shows an example of amplicons resulting after amplification of two target nucleic acids and a barcode sequence (k) attached to a bead (m), according to one embodiment of the invention.

Figure 25:
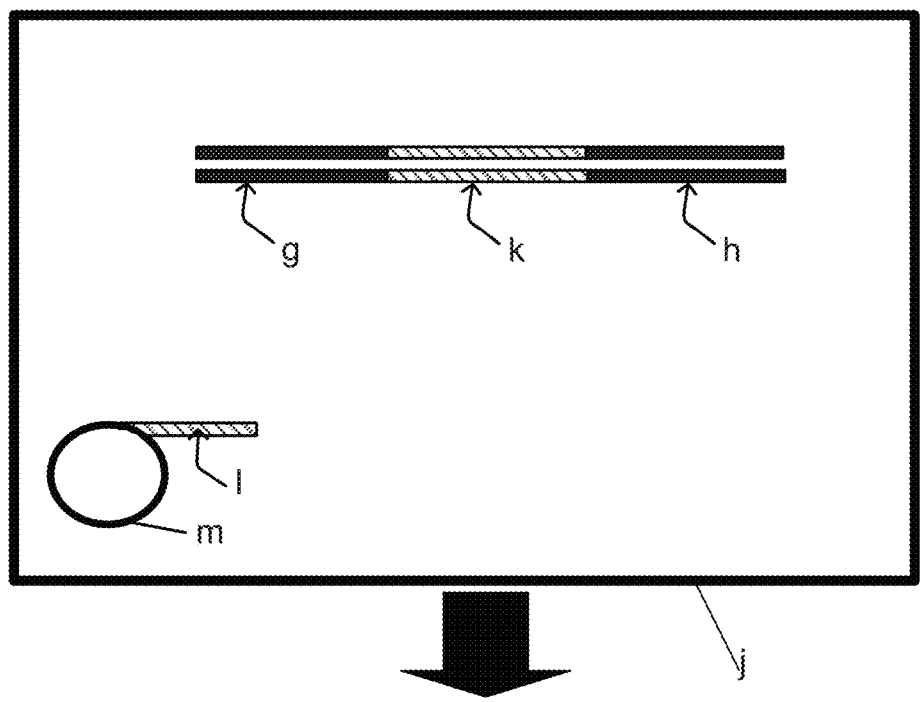

FIG. 25 illustrates a fused amplicon that includes sequences of two target nucleic acids (g and h) and a barcode sequence (k), inside an emulsion droplet or reaction container (j), according to one embodiment of the invention. The fused ("major") amplicon can be isolated by reverse emulsion and bulk sequenced.

Figure 26:
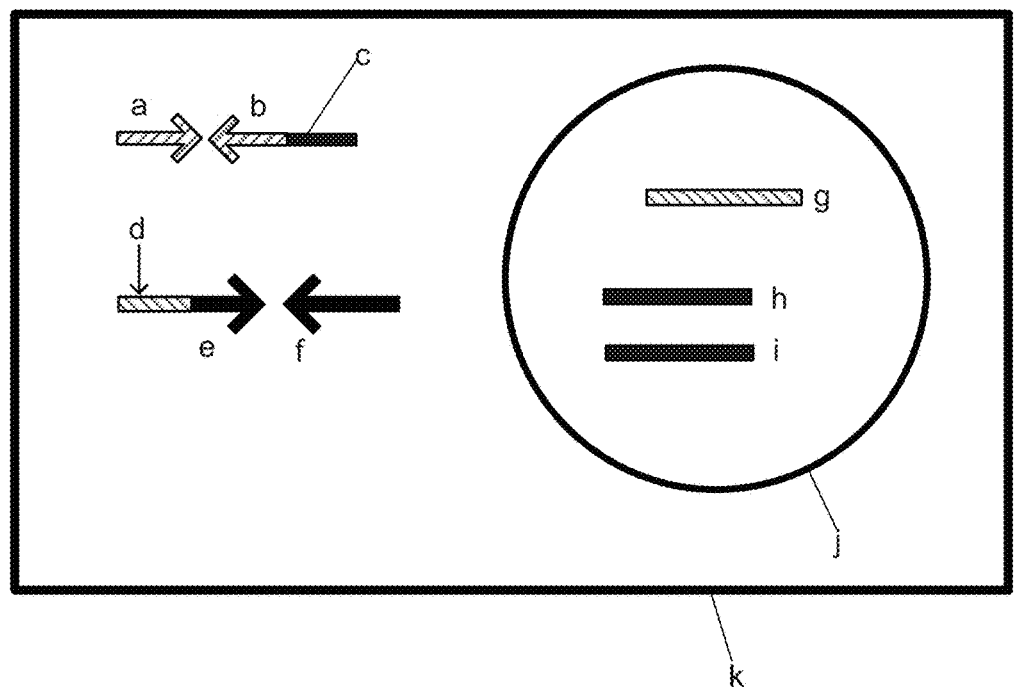

FIG. 26 is an example of single cell sequence linkage by ligase chain reaction combined with overlap extension polymerase chain reaction, as applied to a method for noninvasive prenatal diagnosis, according to one embodiment of the invention.

Figure 27:
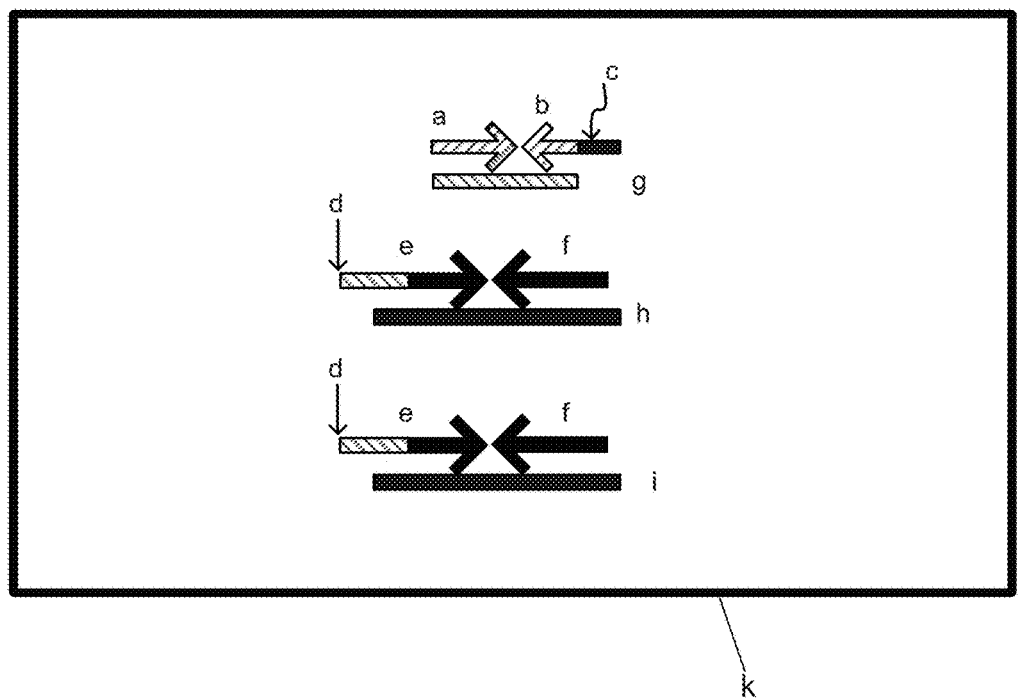

FIG. 27 shows an example of hybridization of primers and target nucleic acids in a single cell sequence linkage by ligase chain reaction combined with overlap extension polymerase chain reaction, as applied to a method for noninvasive prenatal diagnosis, according to one embodiment of the invention. The process is carried out in an emulsion droplet or reaction container (k).

Figure 28:
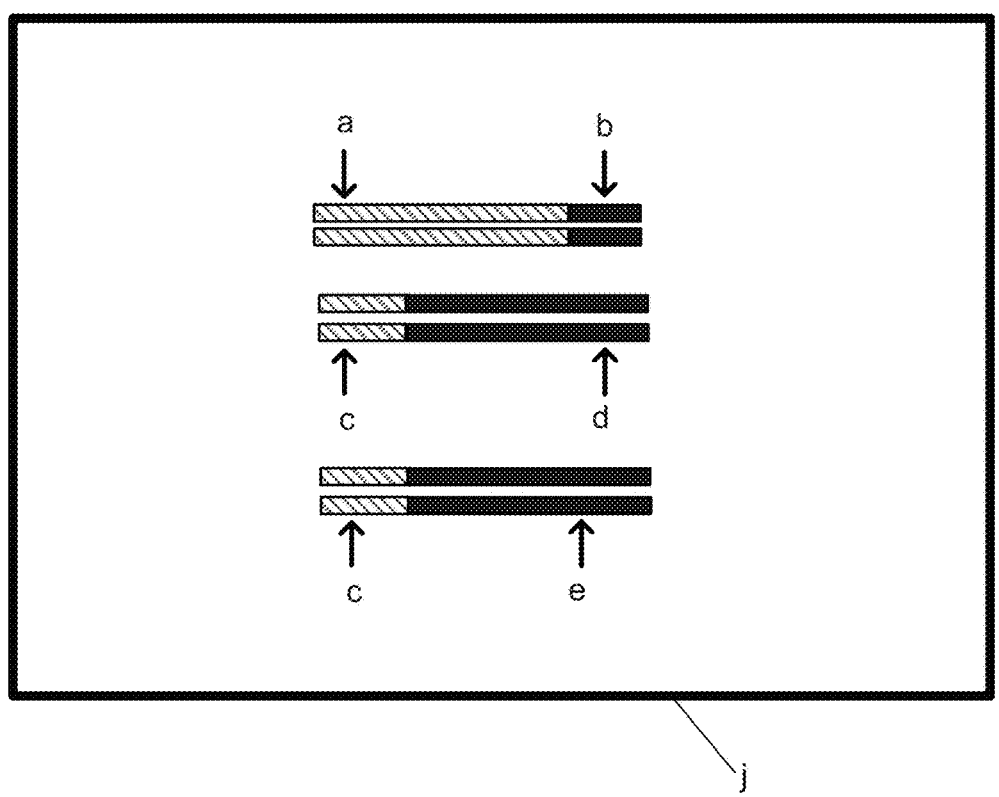

FIG. 28 shows an example of resulting amplicons produced in a single cell sequence linkage by ligase chain reaction combined with overlap extension polymerase chain reaction, as applied to a method for noninvasive prenatal diagnosis, according to one embodiment of the invention.

Figure 29:
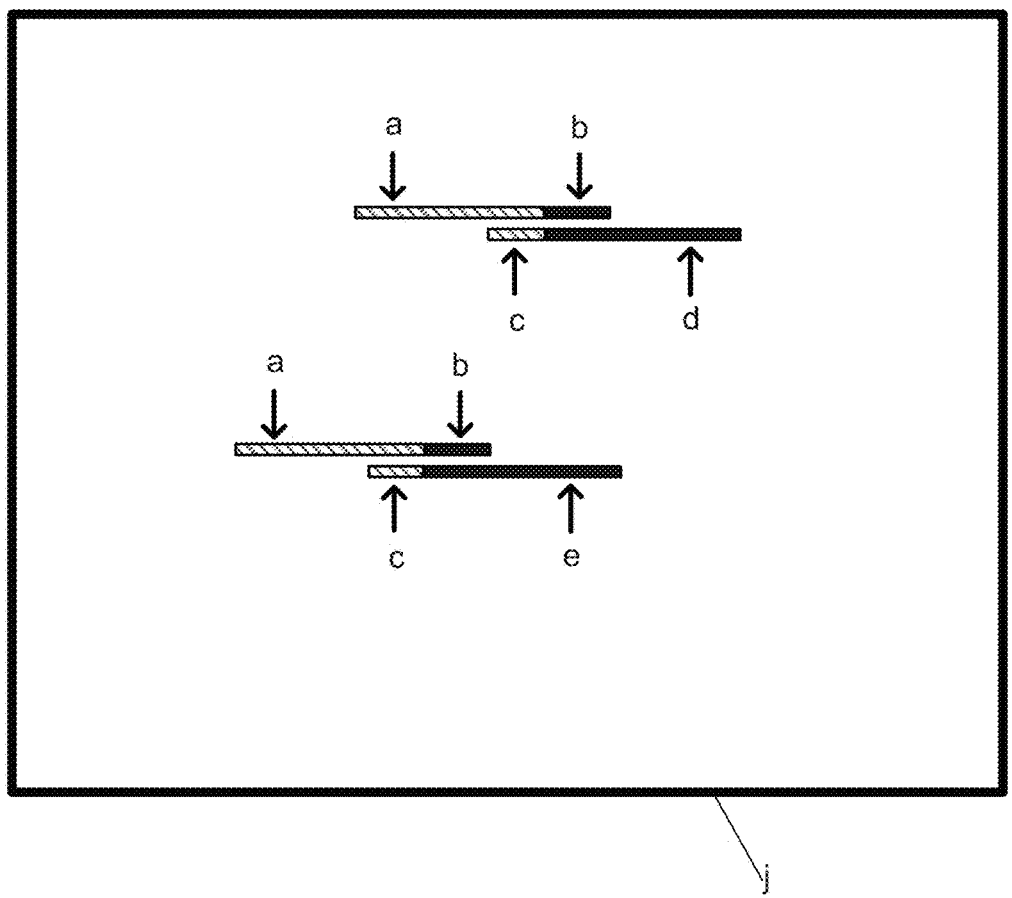

FIG. 29 shows hybridization of overlapping complementary regions of the resulting amplicons, and overlap extension polymerase chain reaction, as applied to a method for noninvasive prenatal diagnosis, according to one embodiment of the invention.

Figure 30:
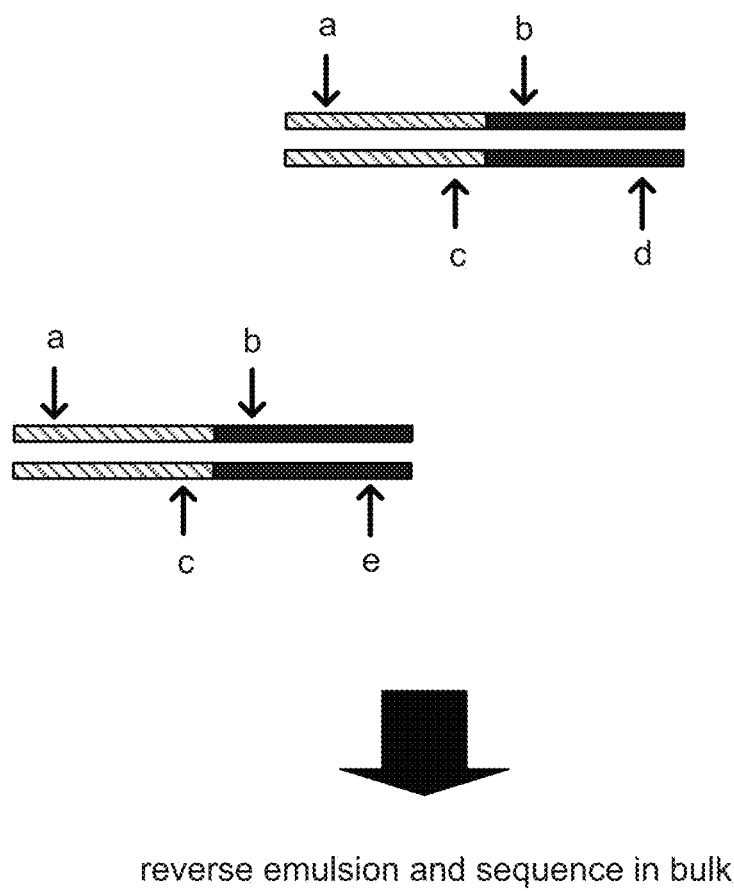

FIG. 30 shows the resulting amplicons from the overlap extension polymerase chain reaction, as applied to a method for noninvasive prenatal diagnosis, according to one embodiment of the invention. The end product is a library of "major amplicons", or linked loci, which can then be sequenced in bulk.

Figure 31:
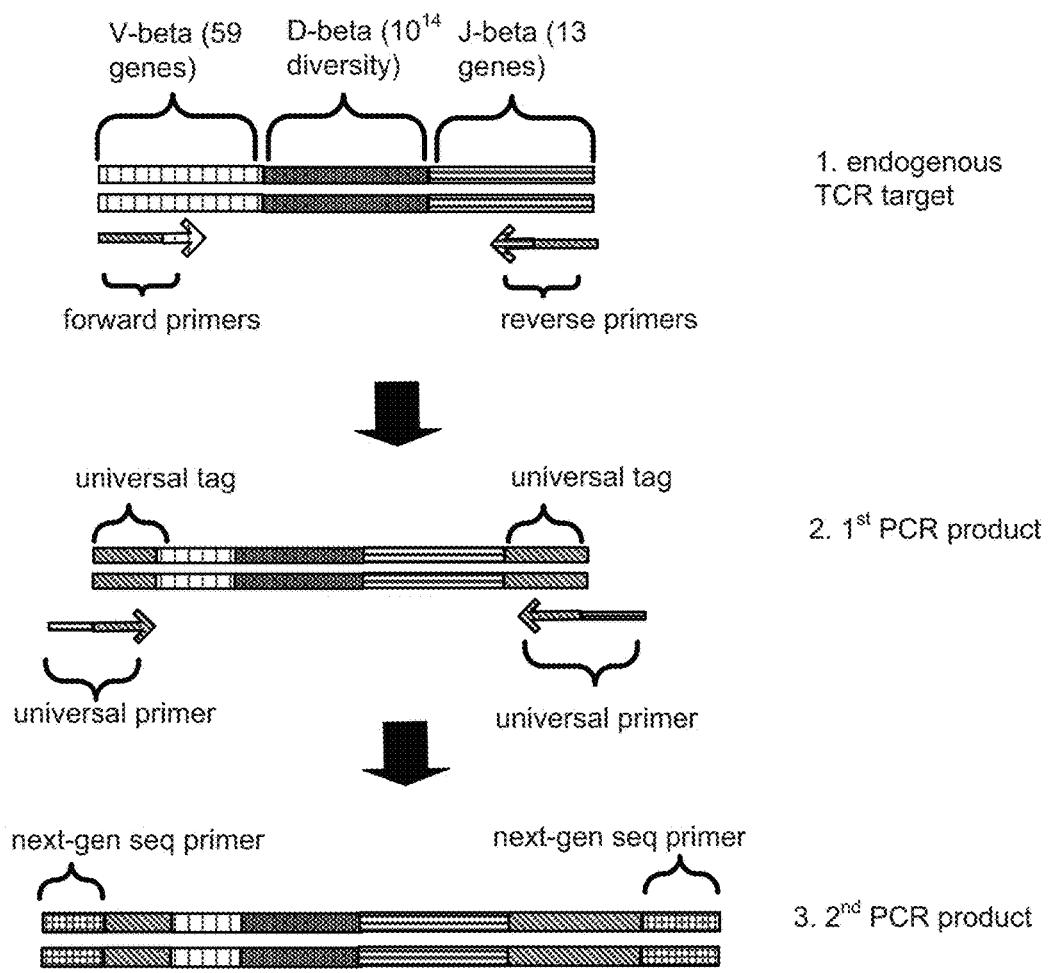

FIG. 31 shows a simplified workflow for high-throughput generation of TCRβ repertoire libraries, according to one embodiment of the invention.

DETAILED DESCRIPTION OF THE INVENTION

Briefly, and as described in more detail below, described herein are methods and systems for massively parallel genetic analysis of single cells in emulsion droplets or reaction containers. Genetic loci of interest are targeted in a single cell using specially-designed probes, and a fusion complex is formed by molecular linkage and amplification techniques. Multiple genetic loci can be targeted, and many sets of probes can be multiplexed by PCR into a single analysis, such that several loci or even the entire transcriptome or genome is analyzed.

The invention is useful for analyzing genetic information in single cells in a high-throughput, parallel fashion for a large quantity of cells ($10^4$ or greater cells). The invention is also useful for tracing genetic information back to a cell or population of cells using unique barcode sequences.

Definitions

Terms used in the claims and specification are defined as set forth below unless otherwise specified.

The term "cell" refers to a functional basic unit of living organisms. A cell includes any kind of cell (prokaryotic or eukaryotic) from a living organism. Examples include, but are not limited to, mammalian mononuclear blood cells, yeast cells, or bacterial cells.

The term "polymerase chain reaction" or PCR refers to a molecular biology technique for amplifying a DNA sequence from a single copy to several orders of magnitude (thousands to millions of copies). PCR relies on thermal cycling, which requires cycles of repeated heating and cooling of the reaction for DNA melting and enzymatic replication of the DNA. Primers (short DNA fragments) containing sequences complementary to the target region of the DNA sequence and a DNA polymerase are key components to enable selective and repeated amplification. As PCR progresses, the DNA generated is itself used as a template for replication, setting in motion a chain reaction in which the DNA template is exponentially amplified. A heat-stable DNA polymerase, such as Taq polymerase, is used. The thermal cycling steps are necessary first to physically separate the two strands in a DNA double helix at a high temperature in a process called DNA melting. At a lower temperature, each strand is then used as the template in DNA synthesis by the DNA polymerase to selectively amplify the target DNA. The selectivity of PCR results from the use of primers that are complementary to the DNA region targeted for amplification under specific thermal cycling conditions.

The term "reverse transcriptase polymerase chain reaction" or RT-PCR refers to a type of PCR reaction used to generate multiple copies of a DNA sequence. In RT-PCR, an RNA strand is first reverse transcribed into its DNA complement (complementary DNA or cDNA) using the enzyme reverse transcriptase, and the resulting cDNA is amplified using traditional PCR techniques.

The term "ligase chain reaction" or LCR refers to a type of DNA amplification where two DNA probes are ligated by a DNA ligase, and a DNA polymerase is used to amplify the resulting ligation product. Traditional PCR methods are used to amplify the ligated DNA sequence. LCR provides greater specificity compared with PCR.

The term "emulsion droplet" or "emulsion microdroplet" refers to a droplet that is formed when two immiscible fluids are combined. For example, an aqueous droplet can be formed when an aqueous fluid is mixed with a non-aqueous fluid. In another example, a non-aqueous fluid can be added to an aqueous fluid to form a droplet. Droplets can be formed by various methods, including methods performed by microfluidics devices or other methods, such as injecting one fluid into another fluid, pushing or pulling liquids through an orifice or opening, forming droplets by shear force, etc. The droplets of an emulsion may have any uniform or non-uniform distribution. Any of the emulsions disclosed herein may be monodisperse (composed of droplets of at least generally uniform size), or may be polydisperse (composed of droplets of various sizes). If monodisperse, the droplets of the emulsion may vary in volume by a standard deviation that is less than about plus or minus 100%, 50%, 20%, 10%, 5%, 2%, or 1% of the average droplet volume. Droplets generated from an orifice may be monodisperse or polydisperse. An emulsion may have any suitable composition. The emulsion may be characterized by the predominant liquid compound or type of liquid compound that is used. The predominant liquid compounds in the emulsion may be water and oil. "Oil" is any liquid compound or mixture of liquid compounds that is immiscible with water and that has a high content of carbon. In some examples, oil also may have a high content of hydrogen, fluorine, silicon, oxygen, or any combination thereof, among others. For example, any of the emulsions disclosed herein may be a water-in-oil (W/O) emulsion (i.e., aqueous droplets in a continuous oil phase). The oil may be or include at least one silicone oil, mineral oil, fluorocarbon oil, vegetable oil, or a combination thereof, among others. Any other suitable components may be present in any of the emulsion phases, such as at least one surfactant, reagent, sample (i.e., partitions thereof), buffer, salt, ionic element, other additive, label, particles, or any combination thereof.

"Droplet" refers to a small volume of liquid, typically with a spherical shape or as a slug that fills the diameter of a microchannel, encapsulated by an immiscible fluid. The volume of a droplet, and/or the average volume of droplets in an emulsion, may be less than about one microliter (i.e., a "microdroplet") (or between about one microliter and one nanoliter or between about one microliter and one picoliter), less than about one nanoliter (or between about one nanoliter and one picoliter), or less than about one picoliter (or between about one picoliter and one femtoliter), among others. A droplet may have a diameter (or an average diameter) of less than about 1000, 100, or 10 micrometers, or of about 1000 to 10 micrometers, among others. A droplet may be spherical or nonspherical. In some embodiments, the droplet has a volume and diameter that is large enough to encapsulate a cell.

The term "barcode" refers to a nucleic acid sequence that is used to identify a single cell or a subpopulation of cells. In some embodiments, a barcode sequence is used to identify a particular organism or a species. As described below, barcode sequences can be introduced into a cell, linked by various amplification methods to a target nucleic acid of interest, and used to trace back the amplicon to the cell. Barcode sequences can be flanked by universal sequences that can be used to amplify libraries of barcodes using universal primer pairs. The barcode sequences can be contained within a circular or linear double-stranded molecule, or in a single-stranded linear molecule.

The term "bulk sequencing" or "next generation sequencing" or "massively parallel sequencing" refers to any high throughput sequencing technology that parallelizes the DNA sequencing process. For example, bulk sequencing methods are typically capable of producing more than one million polynucleic acid amplicons in a single assay. The terms "bulk sequencing," "massively parallel sequencing," and "next generation sequencing" refer only to general methods, not necessarily to the acquisition of greater than 1 million sequence tags in a single run. Any bulk sequencing method can be implemented in the invention, such as reversible terminator chemistry (e.g., Illumina), pyrosequencing using polony emulsion droplets (e.g., Roche), ion semiconductor sequencing (IonTorrent), single molecule sequencing (e.g., Pacific Biosciences), massively parallel signature sequencing, etc.

The term "in situ" refers to examining a biological phenomenon in the environment in which it occurs e.g., the practice of in situ hybridization refers to hybridization of a probe to a nucleic acid target with the cell still intact.

The term "in vivo" refers to processes that occur in a living organism.

The term "mammal" as used herein includes both humans and non-humans and include, but is not limited to, humans, non-human primates, canines, felines, murines, bovines, equines, and porcines.

The term "T cell" refers to a type of cell that plays a central role in cell-mediated immune response. T cells belong to a group of white blood cells known as lymphocytes and can be distinguished from other lymphocytes, such as B cells and natural killer T (NKT) cells by the presence of a T cell receptor (TCR) on the cell surface. T cells responses are antigen-specific and are activated by foreign antigens. T cells are activated to proliferate and differentiate into effector cells when the foreign antigen is displayed on the surface of the antigen-presenting cells in peripheral lymphoid organs. T cells recognize fragments of protein antigens that have been partly degraded inside the antigen-presenting cell. There are two main classes of T cells—cytotoxic T cells and helper T cells. Effector cytotoxic T cells directly kill cells that are infected with a virus or some other intracellular pathogen. Effector helper T cells help to stimulate the responses of other cells, mainly macrophages, B cells and cytotoxic T cells.

The term "B cell" refers to a type of lymphocyte that plays a large role in the humoral immune response (as opposed to the cell-mediated immune response, which is governed by T cells). The principal functions of B cells are to make antibodies against antigens, perform the role of antigen-presenting cells (APCs) and eventually develop into memory B cells after activation by antigen interaction. B cells are an essential component of the adaptive immune system.

It must be noted that, as used in the specification and the appended claims, the singular forms "a," "an," and "the" include plural referents unless the context clearly dictates otherwise.

Methods of the Invention

Methods of Massively Parallel Single Cell Molecular Analysis

A. Microfluidics Methods for Generating Single Cell Emulsion Droplets

In some embodiments, a microfluidic device is used to generate single cell emulsion droplets. The microfluidic device ejects single cells in aqueous reaction buffer into a hydrophobic oil mixture. The device can create thousands of emulsion microdroplets per minute. After the emulsion microdroplets are created, the device ejects the emulsion mixture into a trough. The mixture can be pipetted or collected into a standard reaction tube for thermocycling.

Custom microfluidics devices for single-cell analysis are routinely manufactured in academic and commercial laboratories (Kintses et al., 2010 *Current Opinion in Chemical Biology* 14:548-555). For example, chips may be fabricated from polydimethylsiloxane (PDMS), plastic, glass, or quartz. In some embodiments, fluid moves through the chips through the action of a pressure or syringe pump. Single cells can even be manipulated on programmable microfluidic chips using a custom dielectrophoresis device (Hunt et al., 2008 *Lab Chip* 8:81-87). In one embodiment, a pressure-based PDMS chip comprised of flow-focusing geometry manufactured with soft lithographic technology is used (Dolomite Microfluidics (Royston, UK)) (Anna et al., 2003 *Applied Physics Letters* 82:364-366). The stock design can typically generate 10,000 aqueous-in-oil microdroplets per second at size ranges from 10-150 μm in diameter. In some embodiments, the hydrophobic phase will consist of fluorinated oil containing an ammonium salt of carboxy-perfluoropolyether, which ensures optimal conditions for molecular biology and decreases the probability of droplet coalescence (Johnston et al., 1996 *Science* 271:624-626). To measure periodicity of cell and droplet flow, images are recorded at 50,000 frames per second using standard techniques, such as a Phantom V7 camera or Fastec InLine (Abate et al., 2009 *Lab Chip* 9:2628-31).

The microfluidic system can optimize microdroplet size, input cell density, chip design, and cell loading parameters such that greater than 98% of droplets contain a single cell. There are three common methods for achieving such statistics: (i) extreme dilution of the cell solution; (ii) fluorescent selection of droplets containing single cells; and (iii) optimization of cell input periodicity. For each method, the metrics for success include: (i) encapsulation rate (i.e., the number of drops containing exactly one cell); (ii) the yield (i.e., the fraction of the original cell population ending up in a drop containing exactly one cell); (iii) the multi-hit rate (i.e., the fraction of drops containing more than one cell); (iv) the negative rate (i.e., the fraction of drops containing no cells); and (v) encapsulation rate per second (i.e., the number of droplets containing single cells formed per second).

In some embodiments, single cell emulsions are generated by extreme cell dilution. Under disordered conditions, the probability that a microdroplet will contain k cells is given by the Poisson distribution:

$$f(k; \lambda) = \frac{\lambda^k e^{-\lambda}}{k!},$$

where e is the natural logarithm and the expected number of occurrences in the interval is $\lambda$. Thus, for $P(k=1) \approx 0.98$, the cell solution must be extremely dilute, such that $\lambda \approx 0.04$ and only 3.84% of all drops contain a single cell.

In some embodiments, a simple microfluidic chip with a drop-making junction is used, such that an aqueous stream flows through a 10 μm square nozzle and dispenses the aqueous-in-oil emulsion mixtures into a reservoir. The emulsion mixture can then be pipetted from the reservoir and thermocycled in standard reaction tubes. This method will produce predictably high encapsulation rates and low multi-hit rates, but a low encapsulation rate per second. A design that can achieve filled droplet throughput of 1000 Hz is capable of sorting up to $10^6$ cells in less than 17 minutes.

Fluorescence techniques can also be used to sort microdroplets with particular emission characteristics (Baroud et al., 2007 *Lab Chip* 7:1029-1033; Kintses et al., 2010 *Current Opinion in Chemical Biology* 14:548-555). In these studies, chemical methods are used to stain cells. In some embodiments, autofluorescence is used to select microemulsions that contain cells. A fluorescent detector reduces the negative rate resulting from extreme cell dilution. A microfluidic device can also be equipped with a laser directed at a "Y" sorting junction downstream of the cell encapsulation junction. The Y junction has a "keep" and a "waste" channel. A photomultiplier tube is used to collect the fluorescence of each drop as it passes the laser. The voltage difference is calibrated between empty drops and drops with at least one cell. Next, when the device detects a droplet that contains at least one cell, and electrodes at the Y sorting junction create a field gradient by dielectrophoresis (Hunt et al., 2008 *Lab on a Chip* 8:81-87) and push droplets containing cells in to the keep channel. The microfluidic device uses extreme cell dilution to control the multi-hit rate and fluorescent cell sorting to reduce the negative rate.

In some embodiments, input cell flow is aligned with droplet formation periodicity, such that greater than 98% of droplets contain a single cell (Edd et al., 2008 *Lab Chip* 8:1262-1264; Abate et al., 2009 *Lab Chip* 9:2628-31). In these microfluidic devices, a high-density suspension of cells is forced through a high aspect-ratio channel, such that the cell diameter is a large fraction of the channel's width. The chip is designed with a 27 μm×52 μm rectangular microchannel that flows cells into microdroplets at >10 μL/min (Edd et al., 2008 *Lab Chip* 8:1262-1264). A number of input channel widths and flow rates are tested to arrive at an optimal solution.

In some embodiments, cells with different morphology might behave differently in the microchannel stream of the microfluidic device, confounding optimization of the technique when applied to clinical biological samples. To address this issue, a field gradient perpendicular to the microchannel by dielectrophoresis is induced. Dielectrophoresis pulls the cells to one side of the microchannel, creating in-channel ordering that is independent of cell morphology. This method requires substantial optimization of charge and flow rate and a more complicated chip and device design, so this method may be necessary if existing methodologies fail to perform for certain cell types.

The emulsion microdroplet mixtures are pipetted from the trough in the microfluidic device to a reaction tube for thermocycling. After thermocycling the emulsions, a number of methods might achieve emulsion reversal to recover the aqueous phase of the reaction. Two straightforward reversal processes that have been used by prior investigators are flash-freezing in liquid nitrogen for 10 seconds (Kliss et al., 2008 *Analytical Chem* 80:8975-8981) and passage through a 15 μm mesh filter (Zeng et al., 2010 *Analytical Chem* 82: 3183-90). Emulsion reversal can also be achieved using commercially available reagents designed for this purpose (Brouzes et al., 2009 *PNAS* 106:14195-200). Success of the emulsion reversal is assessed by visualization of the aqueous and hydrophobic phases under a microscope.

In some embodiments, the methods of the invention use single cells in reaction containers, rather than emulsion droplets. Examples of such reaction containers include 96 well plates, 0.2 mL tubes, 0.5 mL tubes, 1.5 mL tubes, 384-well plates, 1536-well plates, etc.

B. Methods for Molecular Linkage in Single Cell Emulsions and Massively Parallel Sequencing 1) Molecular Linkage Using Polymerase Chain Reaction (PCR)

PCR is used to amplify many kinds of sequences, including but not limited to SNPs, short tandem repeats (STRs), variable protein domains, methylated regions, and intergenic regions. Methods for overlap extension PCR are used to create fusion amplicon products of several independent genomic loci in a single tube reaction (Johnson et al., 2005 *Genome Research* 15:1315-24; U.S. Pat. No. 7,749,697).

In some embodiments, at least two nucleic acid target sequences (e.g., first and second nucleic acid target sequences, or first and second loci) are chosen in the cell and designated as target loci. Forward and backward primers are designed for each of the two nucleic acid target sequences, and the primers are used to amplify the target sequences. "Minor" amplicons are generated by amplifying the two nucleic acid target sequences separately, and then fused by amplification to create a fusion amplicon, also known as a "major" amplicon. In one embodiment, a "minor" amplicon is a nucleic acid sequence amplified from a target genomic loci, and a "major" amplicon is a fusion complex generated from sequences amplified between multiple genomic loci. Exemplary primers that can be used for generating minor and major amplicons are listed in Table 2. These primers are used for multiplexed amplification of a single cell's TCRβ and then linkage of the TCRβ to immune effector targets IL-2, IL-4, INFG, TBX21, FOXP3, or TNFA. In one embodiment, SEQ ID NOs: 1-57 are pooled together with primers for a single immune effector target, e.g., SEQ ID NOs: 68 and 69.

The method uses "inner" primers (i.e., the reverse primer for the first locus and the forward primer for the second locus) comprising of one domain that hybridizes with a minor amplicon and a second domain that hybridizes with a second minor amplicon. "Inner" primers are a limiting reagent, such that during the exponential phase of PCR, inner primers are exhausted, driving overlapping domains in the minor amplicons to anneal and create major amplicons.

PCR primers are designed against targets of interest using standard parameters, i.e., melting temperature (Tm) of approximately 55-65° C., and with a length 20-50 nucleotides. The primers are used with standard PCR conditions, for example, 1 mM Tris-HCl pH 8.3, 5 mM potassium chloride, 0.15 mM magnesium chloride, 0.2-2 µM primers, 200 µM dNTPs, and a thermostable DNA polymerase. Many commercial kits are available to perform PCR, such as Platinum Taq (Life Technologies), Amplitaq Gold (Life Technologies), Titanium Taq (Clontech), Phusion polymerase (Finnzymes), HotStartTaq Plus (Qiagen). Any standard thermostable DNA polymerase can be used for this step, such as Taq polymerase or the Stoffel fragment.

In one embodiment, a set of nucleic acid probes (or primers) are used to amplify a first target nucleic acid sequence and a second target nucleic acid sequence to form a fusion complex. The first probe includes a sequence that is complementary to a first target nucleic acid sequence (e.g., the 5' end of the first target nucleic acid sequence). The second probe includes a sequence that is complementary to the first target nucleic acid sequence (e.g., the 3' end of the first target nucleic acid sequence) and a second sequence that is complementary to an exogenous sequence. In some embodiments, the exogenous sequence is a non-human nucleic acid sequence and is not complementary to either of the target nucleic acid sequences. The first and second probes are the forward primer and reverse primer for the first target nucleic acid sequence.

The third probe includes a sequence that is complementary to the portion of the second probe that is complementary to the exogenous sequence and a sequence that is complementary to the second target nucleic acid sequence (e.g., the 5' end of the second target nucleic acid sequence). The fourth probe includes a sequence that is complementary to the second target nucleic acid sequence (e.g., the 3' end of the second target nucleic acid sequence). The third probe and the fourth probe are the forward and reverse primers for the second target nucleic acid sequence.

The second and third probes are also called the "inner" primers of the reaction (i.e., the reverse primer for the first locus and the forward primer for the second locus) and are limiting in concentration, (e.g., 0.01 µM for the inner primers and 0.1 µM for all other primers). This will drive amplification of the major amplicon preferentially over the minor amplicons. The first and fourth probes are called the "outer" primers.

The first and second nucleic acid sequences are amplified independently, such that the first nucleic acid sequence is amplified using the first probe and the second probe, and the second nucleic acid sequence is amplified using the third probe and the fourth probe. Next, a fusion complex is generated by hybridizing the complementary sequence regions of the amplified first and second nucleic acid sequences and amplifying the hybridized sequences using the first and fourth probes. This is called overlap extension PCR amplification.

During overlap extension PCR amplification, the complementary sequence regions of the amplified first and second nucleic acid sequences act as primers for extension on both strands and in each direction by DNA polymerase molecules. In subsequent PCR cycles, the outer primers prime the full fused sequence such that the fused complex is duplicated by DNA polymerase. This method produces a plurality of fusion complexes.

FIGS. 5-6 show an example of the single cell sequence linkage by intracellular overlap extension polymerase chain reaction, according to one embodiment of the invention. In FIG. 5A, a forward primer (a) targets one locus of a first target nucleic acid (g). A reverse primer (b) targets another locus of the first target nucleic acid (g) and has a region of complementarity (c) to a region (d) of the forward primer (e). The forward primer (e) has a region of complementarity to the second target nucleic acid (h) and the reverse primer (f) targets another region of the second target nucleic acid (h). FIG. 5B illustrates an example of the hybridization of the probes (a, b, e and f) to respective target nucleic acids (g and h), according to one embodiment of the invention. FIG. 6A illustrates an example of the complementary regions (c) and (d) between amplicons (g) and (h), according to one embodiment of the invention. FIG. 6B shows linkage amplification of the amplicons (g) and (h) using polymerase (e) to create a linked major amplicon (i). The end product is a library of "major amplicons" that include the linked amplicons (g) and (h), which can be sequenced in bulk. The steps of FIGS. 5-6 can be performed in a reaction container or an emulsion droplet.

In some embodiments, multiple loci are targeted in a single cell, and many sets of probes can be multiplexed into a single analysis, such that several loci or even the entire transcriptome or genome is analyzed. Multiplex PCR is a modification of PCR that uses multiple primer sets within a single PCR mixture to produce amplicons of varying sizes that are specific to different DNA sequences. By targeting multiple genes at once, additional information may be gained from a single test run that otherwise would require several times the reagents and more time to perform. In one embodiment, 10-20 different transcripts are targeted in a single cell and linked to a second target nucleic acid (e.g., linked to a variable region such as a mutated gene sequence, a barcode, or an immune variable region).

In one embodiment, single cells are encapsulated in aqueous-in-oil picoliter microdroplets. The droplets enable compartmentalization of reactions such that molecular biology can be performed on millions of single cells in parallel. Monodisperse aqueous-in-oil microdroplets can be generated on microfluidic devices at size ranges from 10-150 µm in diameter. Alternatively, droplets can be generated by vortexing or by a TissueLyser (Qiagen). Two embodiments of oil and aqueous solutions for creating PCR microdroplets are: (i) PCR buffer that contains 0.5 µg/µL bovine serum albumin (New England Biolabs) combined with mixture of fluorocarbon oil (3M), Krytox 157FSH surfactant (Dupont), and PicoSurf (Sphere Microfluidics); and (ii) PCR buffer with 0.1% Tween 20 (Sigma) combined with a mixture of light mineral oil (Sigma), EM90 (Evonik), and Triton X-100 (Sigma). Several replicate assays quantifying 1 million amplicons by next-generation sequencing have shown that both chemistries form monodisperse microdroplets that are >99.98% stable after 40 cycles of PCR. PCR can occur in a standard thermocycling tube, a 96-well plate, or a 384-well plate, using a standard thermocycler (Life Technologies). PCR can also occur in heated microfluidic chips, or any other kind of container that can hold the emulsion and transfer heat.

After thermocycling and PCR, the amplified material must be recovered from the emulsion. In one embodiment, ether is used to break the emulsion, and then the ether is evaporated from the aqueous/ether layer to recover the amplified DNA in solution. Other methods include adding a surfactant to the emulsion, flash-freezing with liquid nitrogen, and centrifugation.

Once the linked and amplified products are recovered from the emulsion, there are a number of methods to prepare the product for bulk sequencing. In one embodiment, the major amplicon is isolated from the minor amplicons using gel electrophoresis. If yield is not sufficient, the major amplicon is amplified again using PCR and the two outer primers. This material can then be sequenced directly using bulk sequencing. In some embodiments, the outer primers are used to produce molecules than can be sequenced directly. In other embodiments, adapters must be added to the major amplicon before bulk sequencing. Once the sequencing library is synthesized, bulk sequencing can be performed using standard methods and without significant modification.

2) Molecular Linkage Using Reverse Transcriptase Polymerase Chain Reaction (RT-PCR)

The overlap extension PCR method adapts to single tube overlap extension RT-PCR, which amplifies DNA from RNA transcripts. The RT-PCR method combines cDNA synthesis and PCR in enclosed tubes without buffer exchange or reagent addition between the molecular steps. Thermostable reverse transcriptase (RT) enzymes are used that withstand temperatures greater than 95° C., though thermostable RT is not necessary if first strand cDNA synthesis occurs prior to PCR amplification. For example, both ThermoScript RT (Lucigen) and GeneAmp Thermostable rTth (Life Technologies) are designed and used in single-tube reverse transcriptase PCR. In one embodiment, a set of nucleic acid probes (or primers) are used to amplify a first target nucleic acid sequence and a second target nucleic acid sequence to form a fusion complex. The first target nucleic acid sequence or the second target nucleic acid sequence is RNA.

The first probe includes a sequence that is complementary to a first target nucleic acid sequence (e.g., the 5' end of the first target nucleic acid sequence). The second probe includes a sequence that is complementary to the first target nucleic acid sequence (e.g., the 3' end of the first target nucleic acid sequence) and a second sequence that is complementary to an exogenous sequence. In some embodiments, the exogenous sequence is a non-human nucleic acid sequence and is not complementary to either of the target nucleic acid sequences. The first and second probes are the forward primer and reverse primer for the first target nucleic acid sequence.

The third probe includes a sequence that is complementary to the portion of the second probe that is complementary to the exogenous sequence and a sequence that is complementary to the second target nucleic acid sequence (e.g., the 5' end of the second target nucleic acid sequence). The fourth probe includes a sequence that is complementary to the second target nucleic acid sequence (e.g., the 3' end of the second target nucleic acid sequence). The third probe and the fourth probe are the forward and reverse primers for the second target nucleic acid sequence.

The second and third probes are also called the "inner" primers of the reaction (i.e., the reverse primer for the first locus and the forward primer for the second locus) and are limiting in concentration, (e.g., 0.01 µM for the inner primers and 0.1 µM for all other primers). This will drive amplification of the major amplicon preferentially over the minor amplicons. The first and fourth probes are called the "outer" primers.

The method includes amplifying using RT-PCR the first and second nucleic acid sequences independently, such that the first nucleic acid sequence is amplified using the first probe and the second probe, and the second nucleic acid sequence is amplified using the third probe and the fourth probe. Using overlap extension PCR amplification, a fusion complex is generated by hybridizing the complementary sequence regions of the amplified first and second nucleic acid sequences and amplifying the hybridized sequences using the first and fourth probes. (See FIGS. 5-6).

3) Molecular Linkage Using Ligase Chain Reaction

Ligase chain reaction (LCR) is used to target and amplify genetic loci of interest (Landegren et al., 1988 *Science* 241:1077-1080; Benjamin et al., 2003 *Methods in Molecular Biology* 226: 135-149; U.S. Pat. No. 6,235,472). In ligase chain reaction, two polynucleic acid probes target a polynucleic acid locus of interest. Upon hybridization, the two probes are ligated by a ligase enzyme. In contrast with PCR, LCR amplifies both RNA and DNA, facilitating many different kinds of multiplexed analysis. Another notable advantage of ligase chain reaction is the capacity for allele-specific amplification. Whereas PCR amplifies both alleles for a particular variant, the ligation process of LCR is allele-specific.

In some embodiments, LCR probes are used as a molecular "switch." For example, if millions of single cells are screened for a particular variant, only cells that include that variant will produce major amplicons. LCR is used to perform genetic analysis only on cells that contain a particular sequence of interest. Cells that lack the sequence of interest are not substantially amplified and are therefore silent in the reaction. LCR can also be multiplexed more efficiently than PCR, using hundreds of probes targeting hundreds of genetic loci in a single cell microdroplet or intracellular reaction.

Figure 9B:
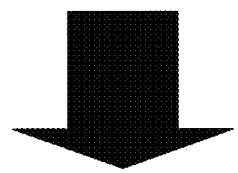

In one embodiment, a single tube-single buffer overlap extension LCR/PCR reaction mixture is formulated using DNA and/or RNA, LCR probes, the PCR primers, Ampligase (Epicentre), a DNA polymerase such as Stoffel fragment (Life Technologies), and reaction buffer (20 mM Tris-HCl, 25 mM KCl, 10 mM $MgCl_2$, 0.5 mM NAD, 0.01% Triton X-100). The method combines LCR with overlap extension PCR to leverage the benefits of both LCR and PCR (FIGS. 7-9). The "inner" probes are added at $\frac{1}{10}^{th}$ of the concentration of the other oligonucleotides in the reaction such that they become a limiting reagent at later cycles. For the initial annealing and ligation, the mixtures can be incubated for 4 minutes at 20° C., 5 minutes at 95° C., and 15 minutes at 60° C. Standard PCR thermocycling conditions are used to amplify the minor and major amplicons (95° C., 5 minutes; [95° C., 30 seconds; 60° C., 30 seconds; 72° C., 30 seconds]×30 cycles). The major amplicon is amplified further by gel size selection and another round of amplification using the outer primers only.

FIGS. 7A and 7B illustrate an example of single cell sequence linkage by intracellular ligase chain reaction combined with overlap extension polymerase chain reaction, according to one embodiment of the invention. A forward LCR primer (a) targets one locus of a first target nucleic acid (g). A reverse LCR primer (b) targets another locus of the first target nucleic acid (g) and has a region of complementarity (c) to a region (d) of the forward primer (e). The forward LCR primer (e) has a region of complementarity to the second target nucleic acid (h) and the reverse LCR primer (f) targets another region of the second target nucleic acid (h).

FIG. 8A shows another example of the complementary regions between amplicons (a) and (d), according to one embodiment of the invention. FIG. 8B shows linkage amplification of the amplicons using polymerase (e) to create a linked major amplicon. The steps of FIGS. 7 and 8 can be performed in a reaction container or an emulsion droplet.

FIG. 9A shows an example of a linked amplicon (f), according to one embodiment of the invention. FIG. 9B shows the resulting amplicon produced from the steps shown in FIGS. 8A and 8B. The end product can be a library of "major amplicons" and are sequenced in bulk.

In another embodiment, the single cell sequence linkage by intracellular ligase chain reaction combined with overlap extension polymerase chain reaction is performed with the following set of probes: a first LCR probe comprising a sequence that is complementary to a first target nucleic acid subsequence, a second probe comprising a sequence that is complementary to a second subsequence of the first target nucleic acid and a second sequence that is complementary to an exogenous sequence, a third probe comprising the exogenous sequence and a sequence that is complementary to a first subsequence of a second target nucleic acid, and a fourth probe comprising a sequence that is complementary to a second subsequence of the second target nucleic acid sequence. The method includes isolating the single cells with at least one set of nucleic acid probes. The first and second probes are hybridized to the first nucleic acid and ligated by a ligase enzyme. Similarly, the third and fourth probes are hybridized to the second target nucleic acid and ligated by a ligase enzyme. Then, the ligated probes for the first and second target nucleic acids are hybridized across the complementary region comprising the exogenous sequence and overlap extension PCR is used to generating a fused complex. The fused complexes can be bulk sequenced.

4) Molecular Linkage Using Padlock Probes

A padlock probe is a circularized, single stranded DNA or RNA molecule with complementarity to a sequence target of interest (Hardenbol et al., 2003 *Nature Biotechnology* 21:673-678; U.S. Pat. No. 6,858,412). After hybridization to the target molecules, a polymerase fills the gap between the two ends of the probe, and a ligase completes the polynucleotide chain to form a circularized polynucleotide molecule. The circularized molecule can then be amplified with multiple displacement amplification (MDA). MDA is an isothermal amplification method that functions by annealing single stranded polynucleotides to the template, followed by DNA synthesis by a high fidelity enzyme such as φ-29 polymerase. Inverse PCR can also be used to amplify only the circularized molecules because PCR primers that amplify the circularized molecules will not amplify the single stranded probes (U.S. Pat. No. 6,858,412).

A notable advantage of padlock probes over PCR is the capacity for allele-specific amplification. Whereas PCR amplifies both alleles for a particular variant, the ligation process of padlock probes is allele-specific. As with LCR, padlock probes are used as a molecular "switch." If millions of single cells are screened for a particular variant, only cells that include that variant will produce major amplicons. Thus, padlock probes are used to perform genetic analysis only on cells that contain a particular sequence of interest. Also, in certain embodiments, padlock probes are highly multiplexed, with tens of thousands of probe types targeting tens of thousands of genetic loci in a single cell microdroplet or intracellular reaction (See U.S. Pat. No. 6,858,412).

Padlock probes are typically hybridized to targets by cycling at least 20 times between 95° C. for 5 min and 55° C. for 20 min (Baner et al., 2003 *Nucleic Acids Research* 31: e103). The single nucleotide gaps are then filled with Stoffel polymerase and ligase, such as Tth ligase or Ampligase (Epicentre). The circularized probes are then be amplified using PCR with universal primers. When multiplexed for overlap extension PCR, two sets of universal primers are used, one for each padlock probe type. The universal primers contain sequence regions of overlap, which enables standard overlap extension PCR following initial sequence capture by the padlock probes. (See FIGS. 10-14). The probes can also be engineered to contain the appropriate primer sequences for bulk sequencing, so the library is sequenced directly after PCR amplification.

FIG. 10 illustrates an example of the components required for a single cell sequence linkage by padlock probes combined with overlap extension polymerase chain reaction, according to one embodiment of the invention. FIG. 11 shows the complementary regions between a first padlock probe (a) and the first target nucleic acid (c) and between a second padlock probe (b) and a second target nucleic acid (d) in a single cell, according to one embodiment of the invention. The reaction components can be contained in a physical reaction container or an emulsion droplet (k). The first padlock probe (a) includes two separate regions that are complementary to the first target nucleic acid (c). The second padlock probe (b) includes two separate regions that are complementary to a second target nucleic acid (d). A polymerase and a ligase are used (m) to amplify and ligate the gap between complementary regions of the padlock probes (a) and (b).

FIG. 12 illustrates the resulting circularized amplicons (g) and (h) and the primers that are used to amplify the circularized amplicons, according to one embodiment of the invention. A forward primer (a) and a reverse primer (i) are used to amplify circular amplicon (g). Forward and reverse primers (j) and (f) are used to amplify circular amplicon (h). Primer (i) has a region (b) that is complementary to a region of amplicon (g) and a region (c) that is complementary to region (d) of primer (j). Primer (j) has a region (e) that is complementary to the amplicon (h) and a region (d) that is complementary to region (c) of primer (i).

FIG. 13 is an example of the resulting amplicons from amplification of the circular probes (g) and (h), according to one embodiment of the invention. In this figure, region (a) is complementary to amplicon (g) and region (b) is complementary to region (c). Region (d) is complementary to amplicon (h) and region (c) is complementary to region (b).

FIG. 14 is an example of overlap extension PCR amplification of the amplicons using a polymerase (e), according to one embodiment of the invention. The resulting amplicon (f) includes sequences (a), (d), and the overlapping sequences (b) and (c). The resulting amplicon (f) can be used for bulk sequencing. The steps can be performed in a reaction container or an emulsion droplet (g).

5) Molecular Linkage Using Multiprobe Circularization

In some embodiments, multiprobe circularization can be used. In multiprobe circularization, two padlock probes target two genetic loci. After hybridization to the target molecules, a polymerase fills the gap between the ends of the two probes, and a ligase completes the polynucleotide chains to form a circularized polynucleotide molecule. (See FIGS. 1A-1C). The circularized molecule can then be amplified with multiple displacement amplification (MDA). Inverse PCR can also be used to amplify only the circularized molecules, because PCR primers that amplify the circularized molecules will not amplify the single stranded probes (See FIGS. 2-3).

Figure 2:
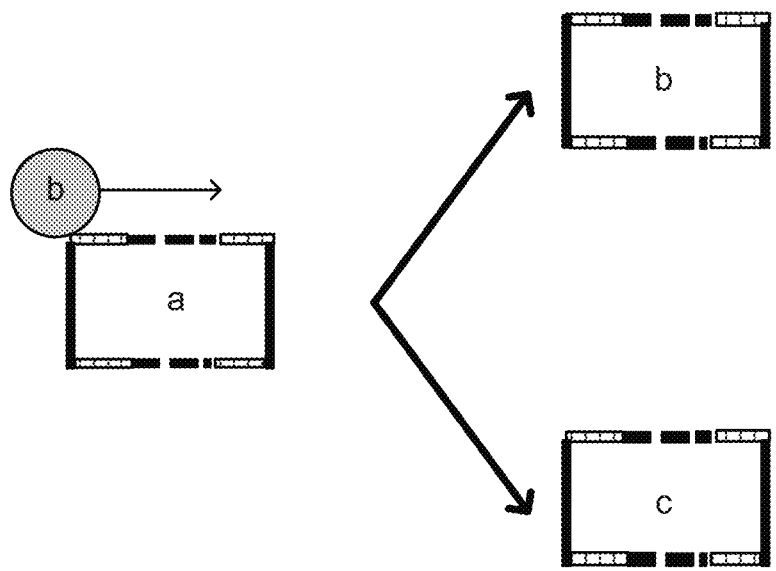
FIG. 2 is an example of amplification of a circularized probe-target linkage complex (a) using a polymerase (b), according to one embodiment of the invention. In some embodiments, a φ-29 polymerase is used in a mediated rolling circle amplification, and copies (b and c) of the circularized probe-target complex are generated.

In one embodiment, the probes are hybridized to targets by cycling at least 20 times between 95° C. for 5 min and 55° C. for 20 min (Baner et al, 2003 *Nucleic Acids Research* 31: e103). The single nucleotide gaps are filled with a Stoffel polymerase and ligase. The circularized probes are amplified using PCR with universal primers. When multiplexed for overlap extension PCR, the two sets of universal primers are used, one for each padlock probe type. The universal primers contain sequence regions of overlap, which enables standard overlap extension PCR following initial sequence capture by the padlock probes (FIGS. 2-3). The probes can also be engineered to contain the appropriate primer sequences for bulk sequencing, so the library is sequenced directly after PCR amplification.

Figure 1A:
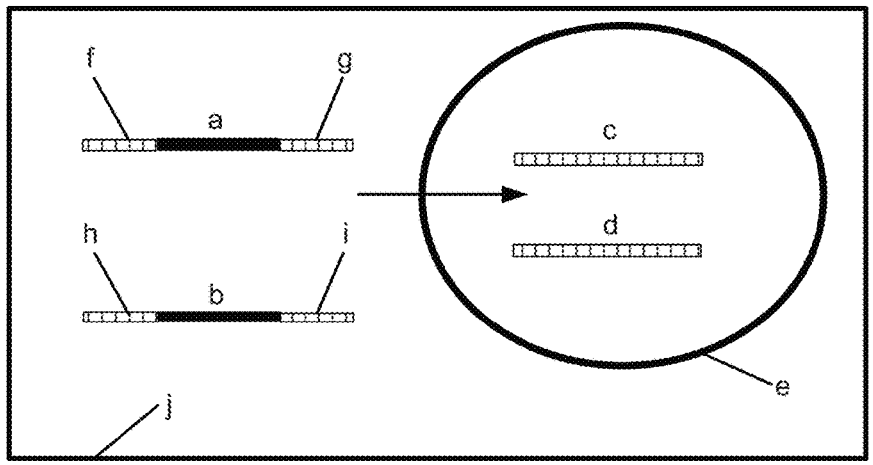
FIG. 1B illustrates an example of sequence linkage in a single cell (also in a reaction container or emulsion droplet (j)) by intra-cellular multiprobe circularization of a complex, according to one embodiment of the invention. The two nucleic acid probes (a and b) are hybridized to the complementary regions of the two target nucleic acids (c and d).
FIG. 1C illustrates an example of circularization of a probe-target linkage complex occurs by amplification, according to one embodiment of the invention.
Figure 1B:
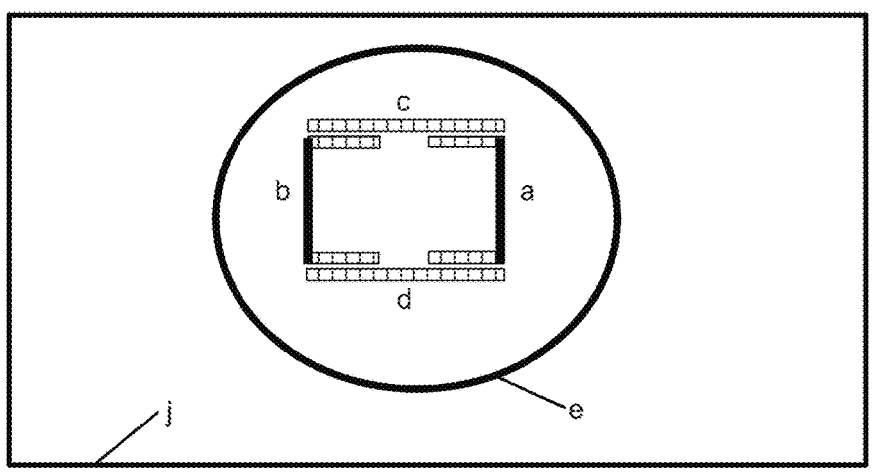
Figure 1C:
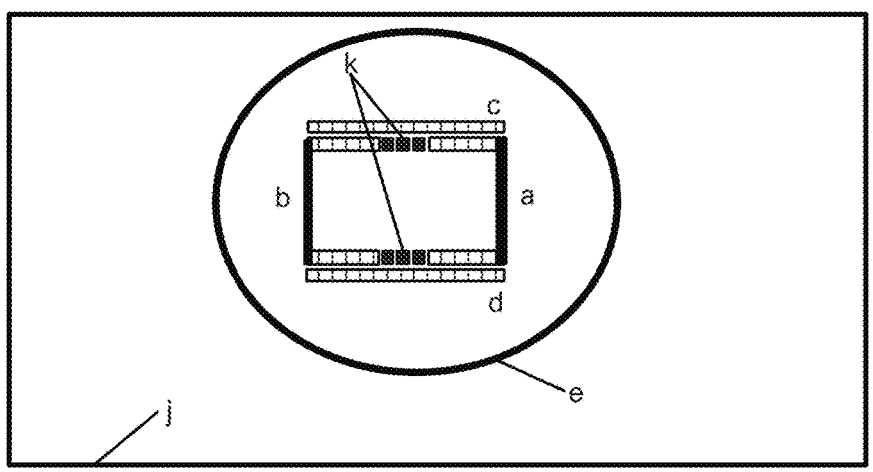

FIG. 1 shows an example of sequence linkage in a single cell by intra-cellular multiprobe circularization of a molecular complex, according to one embodiment of the invention. Each probe has a region of complementarity to each of the target loci. The complex includes two nucleic acid probes (a and b) and two target nucleic acids (c and d). The single cell (e) can be contained in a reaction container or an emulsion droplet (j). FIG. 1A illustrates that the nucleic acid probe (a) has a first region (f) that is complementary to a region on the target nucleic acid (c), and a second region (g) that is complementary to a region on the target nucleic acid (d). The nucleic acid probe (b) has a first region (h) that is complementary to a region on the target nucleic acid (c) and a second region (i) that is complementary to a region on the target nucleic acid (d). FIG. 1B illustrates an example of sequence linkage in a single cell (also in a reaction container or emulsion droplet (j)) by intra-cellular multiprobe circularization of a complex, according to one embodiment of the invention. The two nucleic acid probes (a and b) are hybridized to the complementary regions of the two target nucleic acids (c and d). FIG. 1C illustrates an example of circularization of a probe-target linkage complex occurs by amplification, according to one embodiment of the invention. In one example, a φ-29 polymerase mediated rolling circle amplification is used to circularize the end regions (k) of the two nucleic acid probes (a) and (b).

FIG. 2 shows an example of amplification of a circularized probe-target linkage complex (a) using a polymerase (b), according to one embodiment of the invention. In some embodiments, a φ-29 polymerase is used in a mediated rolling circle amplification, and copies (b and c) of the circularized probe-target complex are generated. In addition, FIG. 3 illustrates an example of amplification of a circularized probe-target linkage complex (a) using a polymerase (b) and primers (c and d), according to one embodiment of the invention. The primers (c and d) are used to amplify the region of the circularized probe-target complex that is complementary to the target nucleic acid. Multiple copies (e) of a linear double-stranded polynucleic acid amplicon are generated and sequenced in bulk.

6) Methods Using Barcode Nucleic Acids

Bulk sequencing requires destruction of cells or emulsion microdroplets, such that all polynucleic acid analytes are pooled into a single reaction mixture. Trace back of a particular sequence target from bulk sequencing data to a particular cell is typically not possible. However, many applications will require trace back of sequences to their original single cells. For example, an investigator may wish to analyze a cell population for single cell expression patterns for two RNA transcripts. Overlap extension reverse transcriptase PCR amplification of two RNA transcript targets followed by bulk sequencing is not adequate for such an analysis because all of the transcripts are mixed together, and transcripts from high-expressing cells are indistinguishable from transcripts from low-expressing cells. To address this problem, polynucleic acid barcodes are used. Each single cell emulsion microdroplet or physical reaction container contains a single unique clonal polynucleic acid barcode. This barcode is then linked to the target polynucleic acids (i.e., RNA transcripts), and is used to trace back the major amplicons to a single cell (See FIGS. 18-25). With trace back of each sequence to an original single cell, it is possible to tabulate genetic data for each single cell, which then enables single cell quantification (i.e., single cell gene expression levels).

In one embodiment, the linker barcode oligonucleotide is highly diluted, such that less than 1% of picoliter emulsion microdroplets carry more than one linker barcode. This enables the linking of a single cell to a single barcode. The linker barcode oligonucleotide is amplified by PCR using universally primers inside each droplet, such that each droplet will contain millions of copies of only one linker barcode sequence, and that barcode will be unique to that droplet (FIGS. 18-21). The dilution follows Poisson statistics such that for $P(k=1) \approx 0.99$, the linker barcodes need to be diluted to $\lambda \approx 0.01$. The barcode is then physically linked to the target molecule by overlap extension PCR. Barcodes can be produced by a number of methods. In one embodiment, a library of random decamers are subcloned into a plasmid vector (e.g., Life Technologies). This produces a mixed plasmid library with >1 million unique decamer barcodes. Then, the plasmids are transformed into bacteria and 3,840 clones are picked. The clones are sequenced by capillary sequencing (Sequetech) and archived in glycerol stocks on 384-well plates. Next, the clones are digested at restriction sites on either side of the random decamer inserts to produce a ~100 bp fragment. These fragments are then biotinylated using Klenow fragment with standard procedures. Washing between molecular steps is performed with the aid of Ampure bead technology (PerkinElmer). The biotinylated fragments are then be affixed to 17 µm diameter streptavidin beads (Life Technologies) in each well, producing 3,840 clonal populations of barcode beads. Nucleic acid amplification using bead emulsions is described in U.S. Pat. No. 7,842,457.

In one embodiment, the method provides beads attached to barcode nucleic acid sequences. A library of random 15-mers is subcloned into a plasmid vector (Life Technologies). This produces a mixed plasmid library with >1 billion unique 15-mer barcodes. The biotinylated fragments are then affixed to 17 µm diameter streptavidin beads (Life Technologies). The plasmid barcode mixture is diluted in PCR mix such that 99% of the droplets that contain a plasmid will contain only a single clonal plasmid. The PCR mix contains biotinylated nucleotides, such that amplified barcodes are biotinylated. Then, streptavidin beads are flowed into this PCR mix to encapsulate single beads in microdroplets. At least 10 million beads are typically encapsulated, and then the bead/plasmid mixes are thermocycled to amplify and biotinylate the barcodes. The barcoded beads are then recovered and can be used in the droplet barcoding method.

In another embodiment, a microfluidic device injects beads coated with clonal linker barcode oligonucleotides into the single cell emulsion microdroplets. Such a device enables visualization of single beads and single cells in each drop, eliminating the requirement for highly dilute linker barcode oligonucleotides. In this embodiment, PCR is also used to amplify the linker barcode oligonucleotide, such that each droplet contains millions of copies of the same barcode sequence, but each barcode would be unique to a single microdroplet. The barcode is then linked to the target nucleic acid sequence using overlap extension PCR. During overlap extension PCR amplification, the complementary sequence regions of the amplified first and second nucleic acid sequences act as primers for extension on both strands in each direction by DNA polymerase molecules. In subsequent PCR cycles, the outer primers prime the full fused sequence such that it is duplicated by DNA polymerase. This method produces a plurality of fusion complexes.

In another embodiment, the method includes steps for providing a pool of unique barcode sequences, where each barcode sequence is linked to a selection resistance gene, providing a population of single cells, transfecting the population of single cells with the pool of unique barcode sequences, selecting cells comprising a unique barcode sequence and the selection resistance gene, and isolating each of the selected cells into reaction containers or emulsion microdroplets. In some embodiments, the selection resistance gene encodes resistance to gentamycin, neomycin, hygromycin, or puromycin. The selection resistance gene enables one to select cells that have incorporated the barcode sequence into the cell. Cells that lack the plasmid also lack the selection resistance gene and therefore are killed in the presence of a mammalian selection chemical such as gentamycin, neomycin, hygromycin, or puromycin.

FIG. 15 illustrates an example of plasmid library deconvolution by barcoded tailed end (5'-end barcoded) polymerase chain reaction, which is followed by bulk sequencing and informatics, according to one embodiment of the invention. The barcode sequence can be traced back to a well and plate position, the barcode sequence can then be traced to a nucleic acid sequence, and the nucleic acid sequence is traced back to a well. Each of the primers in (a) and (b) have a 5'-end barcoded tag. The target nucleic acids in (c) and (d) are amplified using the primers in (a) and (b). The steps can be performed in enclosed containers or emulsion droplets, as shown in (c) and (d). FIG. 16 also shows an example of amplification (e, f) of two target nucleic acids (A and B) using primers that include barcode sequences, according to one embodiment of the invention. The resulting amplicons that include the barcode sequences are shown in (g) and (h). Moreover, FIG. 17 illustrates a simplified example of tracing back a barcode sequence in an amplicon to a cell target (A or B), and tracing back the cell target to a physical location (c, d) (e.g., a well), according to one embodiment of the invention.

In addition, FIG. 18 illustrates the components for molecular linkage between two transcripts (g and h) and a molecular barcode sequence (k), according to one embodiment of the invention. The targets (g and h) can be RNA transcripts, and the molecular barcode sequence (k) is flanked by universal priming sites. Only one copy of the molecular barcode oligonucleotide is contained in the emulsion droplet or reaction container (j), and universal PCR primers amplify the oligonucleotide to produce a plurality of clonal barcode polynucleic acids. A forward primer (a) and reverse primer (m) are used to amplify target nucleic acid (g). A forward primer (n) and reverse primer (f) are used to amplify target nucleic acid (h). The reverse primer (m) includes a region (b) that is complementary to the target nucleic acid (g) and a region (c) that is complementary to region (d) on primer (n). Primer (n) includes a region (e) of complementarity to target nucleic acid (h) and a region (d) of complementarity to region (c) of primer (m). In some embodiments, more than two targets can be linked, and the targets can also be DNA.

In addition, FIG. 19 shows an example of amplification of the target nucleic acids (g and h) using primers as shown, according to one embodiment of the invention. The forward primer (a) is complementary to target nucleic acid (g), and the reverse primer (b) for the target nucleic acid (g) includes a region (c) that is complementary to the barcode sequence (k). Forward primer (e) and reverse primer (f) are used to amplify target nucleic acid (h). The forward primer (e) includes a region (d) that is complementary to the barcode sequence (k).

In FIG. 20, amplicons resulting after amplification of two target nucleic acids and a barcode sequence (k) are shown, according to one embodiment of the invention. FIG. 21 illustrates a fused amplicon that includes sequences of two target nucleic acids (g and h) and a barcode sequence (k) inside an emulsion droplet or reaction container (j), according to one embodiment of the invention. The fused ("major") amplicon can be isolated by reverse emulsion and bulk sequenced. In FIG. 22, the targets (g and h) can be RNA transcripts, and the molecular barcode sequence (k) is flanked by universal priming sites. Only one copy of the molecular barcode sequence (k) is contained in the single cell emulsion droplet or reaction container (j), and universal PCR primers amplify the oligonucleotide to produce a plurality of clonal barcode polynucleic acids. Forward primer (a) and reverse primer (b) are used to amplify target nucleic acid (g). Forward primer (n) and reverse primer (f) are used to amplify target nucleic acid (h). The reverse primer (m) includes a region (b) that is complementary to the target nucleic acid (g) and a region (c) that is complementary to region (d) on primer (n). Primer (n) includes a region (e) of complementarity to target nucleic acid h) and a region (d) of complementarity to region (c) of primer (m). In some embodiments, more than two targets can be linked, and the targets can also be DNA.

FIG. 23 illustrates the forward and reverse primers that are used in a molecular linkage between two transcripts (g and h) and a molecular barcode sequence (k) attached to a bead (m), according to one embodiment of the invention. Forward primer (a) and reverse primer (b) are used to amplify target nucleic acid (g). Forward primer (n) and reverse primer (f) are used to amplify target nucleic acid (h). The reverse primer (m) includes a region (b) that is complementary to the target nucleic acid (g) and a region (c) that is complementary to region (d) on primer (n). Primer (n) includes a region (e) of complementarity to target nucleic acid (h) and a region (d) of complementarity to region (c) of primer (m). The two target nucleic acids are complementary to a DNA sequence (l). FIG. 24 is an example of amplicons resulting after amplification of two target nucleic acids and a barcode sequence (k) attached to a bead (m), according to one embodiment of the invention. FIG. 25 illustrates a fused amplicon that includes sequences of two target nucleic acids (g and h) and a barcode sequence (k), inside an emulsion droplet or reaction container (j), according to one embodiment of the invention. The fused ("major") amplicon can be isolated by reverse emulsion and bulk sequenced. FIGS. 24-25 illustrate an example of amplicons resulting after amplification of two target nucleic acids and a barcode sequence (k) attached to a bead (m), according to one embodiment of the invention.

7) Methods Using Combination Amplification

Targeting and amplification of genetic loci in cells can be performed using PCR, LCR, padlock probes, RT-PCR, or multi-probe circularization. Any combination of these methods to target and amplify different loci can be used. For example, a combination amplification approach is used to amplify a genomic DNA locus and an RNA transcript. In one embodiment, a thermostable reverse transcriptase enzyme, such as ThermoScript RT (Lucigen) or GeneAmp Thermostable rTth (Life Technologies), is combined with a thermostable DNA polymerase, such as the Stoffel fragment or Taq DNA polymerase. Thermocycling can induce first strand cDNA synthesis from the RNA transcript target. Once cDNA from the RNA transcript is synthesized, overlap extension PCR is performed using the cDNA and the genomic DNA target sequences.

8) Bulk Sequencing Methods

There are a number of new commercial methodologies for polynucleic acid sequencing. These technologies are often referred to as "next generation sequencing," "massively parallel sequencing," or "bulk sequencing." These terms are used interchangeably to describe any sequencing method that is capable of acquiring more than one million polynucleic acid sequence tags in a single run. Typically these methods function by making highly parallelized measurements, i.e., parallelized screening of millions of DNA clones on glass slides. The methods for linking multiple polynucleic acid targets in single cells could be used in combination with any commercialized bulk sequencing method. These methods include reversible terminator chemistry (Illumina), pyrosequencing using polony emulsion droplets (Roche), single molecule sequencing (Pacific Biosciences), and others (IonTorrent, Halcyon, etc.).

After the molecular linkage protocols are performed, and before bulk sequencing, it is useful to specifically amplify and purify major amplicons to reduce the overall sequencing required to obtain useful data. Otherwise, many minor amplicons and other kinds of unwanted background sequences will be sequenced unnecessarily. This is accomplished by PCR using only the outer primers and the nucleic acid analyte obtained from the lysed cells, followed by size selection using a method such as gel agarose electrophoresis. Other methods, such as size exclusion columns, microfluidic electrophoresis, or micropore filters, might be used to select the proper size molecules.

In one embodiment, the method provides the step of performing a bulk sequencing reaction to generate sequence information for at least 100,000 fused complexes from at least 10,000 cells within a population of cells. In another embodiment, the bulk sequencing reaction generates sequence information for at least 75,000, 50,000, or 25,000, or 10,000 fused complexes from at least 10,000 cells within a population of cells.

The fused complexes can then be used to quantify the particular biological or clinical phenomenon of interest. In the case of functional T or B cell analysis, particular clonotypes that express functional molecules can be analyzed by first determining the CDR3 peptide sequence of the fused complex, and then tabulating the instances of that CDR3 peptide linked to a particular effector molecule. In this way the bulk sequencing quantifies clonal expansion and biological function of each single clonotype. When primers targeting multiple effector molecules and all possible variable regions are multiplexed into a single assay, and one can separate clonotypes into functional compartments. In the case of linkage between barcodes and transcript targets, one can stratify the bulk sequencing data by barcode and then tabulate the instances of a particular barcode linked to a transcript target. When primers targeting multiple transcripts are multiplexed into a single assay, one can use barcodes to infer multigenic expression patterns for single cells traced back to single droplets. In the case of linkage between a mutant or variable sequence and other mutant or variable sequences, one can analyze the bulk sequencing data to determine the sequence at each locus in each molecule in the bulk sequencing library, and then tabulate the instances of each sequence type. If, for example, a mutation in each of the two linked targets is required to produce a disease phenotype, quantifying the number of linked targets with two mutations can be used to detect disease in an individual.

C. Intracellular Linkage in Fixed Cells Followed by Massively Parallel Sequencing The molecular methods described in section B above can be performed intracellularly in thousands to millions of single fixed cells (Embleton et al., 1992 *Nucleic Acids Research* 20:3831-37; Hviid, 2002 *Clinical Chemistry* 48:2115-2123; U.S. Pat. No. 5,830,663). The cell membranes of the cells serve as reaction compartments, enabling linkage between two or more genetic loci in thousands to millions of single fixed cells analyzed in parallel. Using fixed cells as reaction compartments is more cost-effective than a microfluidic chip to make emulsion microdroplets. Also, heterogeneity in cell size or morphology in a particular cell population is less likely to disrupt the fixed cell method than the emulsion microdroplet method. However, in some cases, leakage of nucleic acids from cells can cause background noise in the molecular genetic analysis, so care must be taken to wash cells between molecular steps and perform rigorous quality analysis of analytes. Therefore, in one embodiment, fixed and permeabilized cells are encapsulated into microdroplets, and amplification occurs using fixed, permeabilized cells in microdroplets instead of lysed cells inside of microdroplets.

1) Molecular Linkage in Fixed Cell Methods

Our work using single cell whole genome amplification (WGA) and PCR from single fixed cells has shown that cell fixation in glutaraldehyde inhibits WGA but not PCR. In any embodiment of intracellular linkage protocols, care must be taken to ensure that fixation and/or permeabilization does not inhibit molecular amplification.

For fixation, reagents such as glutaraldehye, paraformaldehyde, IntraStain (Dako), or similar reagents can be used. For permeabilization, reagents such as Triton X-100, Tween-20, IntraStain (Dako), or similar reagents can be used (Lippincott-Schwartz 2003 *Short Protocols in Cell Biology*; Celis 2005 *Cell Biology: A Laboratory Handbook*). After fixation and/or permeabilization, the cells are washed multiple times in a buffer, such as phosphate-buffered saline (PBS). Once the cells are fixed and/or permeabilized, reaction buffers containing primers/probes and enzymes are delivered to the intracellular compartment without special machinery or methods.

For example, when using RT-PCR to amplify the target loci in single cells, the fixed and permeabilized cells are soaked in reaction buffer and the first strand cDNA is intracellularly synthesized at 55-70° C. for four hours. Without washing or buffer exchange, one could then use standard overlap extension PCR thermocycling conditions to amplify and link the targets. After this amplification procedure, the mixture is washed several times with PBS, and the supernatant is retained for quality control analysis. The membranes of the resuspended cells are then disrupted using alkaline lysis buffer or proteinase K solutions (Johnson et al., 2010 *Human Reproduction* 25:1066-75).

After lysis of the cells and before bulk sequencing, it is useful to specifically amplify linked complexes to reduce the overall sequencing required to obtain useful data. This is accomplished by PCR using only the outer primers and the nucleic acid analyte obtained from the lysed cells, followed by size selection using a method such as gel agarose electrophoresis.

II. Methods of Pooled Clone Library Deconvolution

Highly multiplexed libraries of nucleic acids are often produced using parallelized methods that fail to produce individual molecules at optimized molarity for applications of interest. The method herein provides for parallelized synthesis, deconvolution, and re-multiplexing of polynucleic acid libraries. The method retains the advantages of both parallelized synthesis and individual clone optimization. These polynucleic acid libraries are used for a variety of applications, including but not limited to, multiplexed amplification of target nucleic acid sequences for sequencing and analysis (FIGS. 15-17).

A. Padlock Probe Synthesis Method

1) Pre-Probe Pool Deconvolution Method

In one embodiment, a pool of thousands of padlock probes that target single nucleotide polymorphisms, or SNPs, are generated. DNA oligonucleotide probe precursors are synthesized in pools (Atactic or NimbleGen). Universal primers are then used to PCR amplify double-stranded DNA from the oligonucleotide pool (Porreca et al., 2007 *Nature Methods* 4:931-36). Next, the ends of the double-stranded PCR amplicon library are digested using a restriction enzyme. For example, EcoP15I is used, which cleaves 25 base pairs from the recognition site and removes the universal PCR binding sites. EcoP15I is one example of an enzyme that is adequate for subcloning, and uncleaved products do not affect downstream molecular steps. The digested library is subcloned into custom-engineered plasmid vectors that confer ampicillin resistance. The plasmids are then transformed into bacterial cultures under selection with an antibiotic.

FIG. 4 illustrates an example of amplification of a circularized probe-target linkage complex (a) in a single cell (b), according to one embodiment of the invention. Amplification occurs by transformation into bacteria and subsequent selection with antibiotics. The amplicon (a) contains an antibiotic resistant gene and cells (c) that are transformed with the amplicon are selected in the presence of antibiotics. Cells without the circularized probe-target complex (d) are not selected.

2) Single Stranded Probe Synthesis En Masse

In some embodiments, a bacterial stock containing a mixed library of thousands of clones, each targeting a particular SNP, is used for single stranded probe synthesis en masse. For example, the bacterial cultures are spread on LB agar plates under ampicillin selection, and then individual colonies are picked. Next, PCR with barcoded primers is used to amplify the probe sequence and flanking universal priming regions. The result is an amplicon that contains both the probe sequence and a barcode that can be traced back to a single well. In one embodiment, a unique molecular barcode will indicate a particular well position in a particular 384-well plate. For example, the system could have 3,840 unique barcodes that indicate the well positions and plate number for 3,840 PCRs in one of ten 384-well plates. To deconvolute a 10,000-plex library of clones, four rounds of deconvolution are performed using the set of 3,840 barcoded PCRs, and oversampling and screening a total of 15,360 clones. For each round of deconvolution, the PCR products can then be pooled and sequenced using any bulk sequencing method.

With the probe sequences matched to a barcode, a deconvolution algorithm can then be used to deconvolute the library. Because the barcode is matched to the insert sequence, a table is created that matches the barcode sequence to the original well and plate, and accordingly, this matches the insert sequence to a well. The bacterial clones can then be stored as glycerol stocks, and sequences of these stocks can then be catalogued in a database and stored at −80° C.

To synthesize single stranded padlock probes from the template glycerol stocks, a derivation of the SMART technique is used (Krishnakumar et al., 2008 *PNAS* 105:9296-9301). At a high level, this method involves (i) digestion of a double stranded DNA with a restriction endonuclease; (ii) dephosphorylation of the "sticky end"; (iii) digestion of the second end of the double stranded DNA with a second restriction endonuclease; and (iv) digestion of the desphosphorylated strand of DNA using a λ exonuclease. First, the desired clones are picked, and then cultured in 384-well plates. After incubation overnight, the optical density of each culture is assessed, and then the stocks are equalized. 5 μL from the normalized bacterial cultures is pooled, and the plasmid pool is purified using standard methods (Qiagen). Next, a set of universal PCR primers is used to generate a pool of double-stranded PCR amplicons. The resulting PCR mixture is then subjected to digestion with a restriction enzyme, such as HaeIII (NEB), followed by dephosphorylation with shrimp alkaline phosphatase (SAP). After desphosphorylation, the analyte is digested with a restriction enzyme, such as BstUI (NEB). This product can then be digested with λ exonuclease (NEB), producing single stranded DNA molecules. Finally, single stranded DNA (ssDNA) is purified from any undigested double stranded DNA using a commercial kit (Zymo Research). In this way, hundreds of thousands of probes are synthesized in parallel.

B. Cell Clone Deconvolution

The methods in Section II. A. can also be used to deconvolute mixed libraries of cells or organisms with different underlying genetic characteristics. The goal is to separate the mixed library of clones into reaction compartments, perform barcoded PCR followed by bulk sequencing on the clones, and then map sequence data back to the clones in reaction compartments. In one example, a population of mammalian cells is mutagenized and then clonal populations of mutagenized cells are isolated from the mixed population. In this embodiment, single mutagenized cells are sorted into reaction compartments, and then targeted barcoded PCR or padlock probes are performed at genetic loci of interest. Bulk sequencing data is used to trace back to the original clones, and then the physical clone stocks is used for further investigation or use.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B (1992).

Example 1: Methods of T-Cell Analysis

The immune system responds to disease by inducing cellular responses. Nearly all immunology is involved with detection of clonotype expansion or contraction in response to an antigen and/or functional analysis of the expanded or contracted clonotypes. Described in this example are methods that leverage the information contained in immune response to diagnose and treat disease. Active and/or memory cells are particularly informative because these cells indicate a functional immune response to a disease, and therefore have high information content. Variable DNA regions and RNA transcripts were analyzed in single cells from populations of activated and/or memory immune cells, and then correlated with disease. These profiles were used to develop noninvasive diagnostics, high-value diagnostics that inform treatment regimens, and novel therapeutic agents.

T cells include T cell receptors (TCR) that recognize antigens and control immune responses. The T cell receptor is composed of two subunits: α and β or γ and δ. Current methods to examine T cells by their T cell receptors overwhelmingly sequence T cell receptor subunits from bulk populations that range from a few to millions of cells. This results in a catalogue of subunit sequences (α or δ) that are unlinked to the other corresponding subunit sequence found in individual cells (β or γ). This gives population level information about T cell receptor diversity but does not give a description of individual T cell receptors in individual cells by both subunits (α and β or γ and δ). By linking sequences in a single cell using the methods in Sections I. A-C, the TCRs of individual cells in mixed populations are analyzed with finer resolution, and this allows an unprecedented mapping of human T-cell diversity.

The sequences of TCR subunits and immune functionality molecules were linked using the methods described in Sections I. A-C. This approach, called "functional T cell sequencing," focused specifically on T cells likely to have a clinically or biologically relevant function. For example, the immune function of a T cell is indicated by expression of both clonal TCR and signaling molecules such as interleukin-4 (IL-4). Naïve T cells express clonal TCR but do not express signaling molecules such as IL-4, and have different immune functions. The TCR was linked to the signaling molecule, which in turn linked the TCR to clinical function. Primers amplifying the full TCRβ repertoire were linked to a single immune effector molecule, such as IL-4. Primers amplifying the full TCRβ repertoire were linked to dozens of immune effector molecules, resulting in a full T cell phenotype for each T cell clonotype in the assay.

Examples of molecules that are associated with immune function and that are linked to a TCR sequence include, but are not limited to: interleukin-2 (IL-2), interleukin-4 (IL-4), interferon gamma (IFNγ), interleukin-10 (IL-10), interleukin-1 (IL-1), interleukin-13 (IL-13), interleukin-17 (IL-17), interleukin-18 (IL-18), tumor necrosis factor alpha (TNFα), tumor necrosis factor beta (TNFβ), T-box transcription factor 21 (TBX21), forkhead box P3 (FOXP3), cluster of differentiation 4 (CD4), cluster of differentiation 8 (CD8), cluster of differentiation 1d (CD1d), cluster of differentiation 161 (CD161), cluster of differentiation 3 (CD3), and T-box transcription factor TBX21 (T-BET).

The TCR β chain was linked to a molecule associated with immune function. In another exemplary method, the TCR α and β, or TCR γ and δ, or any of the individual subunits, were linked to immune functionality molecules. Published primers optimized for amplification of recombined genomic TCR were used (Robins et al., 2009 *Blood* 114:4099-107). Much of the peptide variability of the TCR was encoded in CDR3β, which was formed by recombination between noncontiguous variable (V), diversity (D), and joining (J) segments in the b chain loci (Wang et al., 2010 *PNAS* 107:1518-23). Previously published PCR primers targeting the CDR3β locus can also be used (Robins et al., 2009 *Blood* 114:4099-107; Robins et al., 2010 *Science Translational Med* 2:47ra64). This set of forty-five forward primers and thirteen reverse primers amplify the ~200 base pair recombined genomic CDR3β region for multiplex amplification of the full CDR3β complement of a sample of human peripheral blood mononuclear cells. The CDR3β region begins with the second conserved cysteine in the 3' region of the Vβ segment and ends with the conserved phenylalanine encoded by the 5' region of the Jβ segment (Monod et al., 2004 *Bioinformatics* 20:i379-i385). Thus, amplified sequences were informatically translated to locate the conserved cysteine, obtain the intervening peptide sequence, and tabulate counts of each unique clone in the sample.

Examples of primers that can be used for multiplex amplification of TCR sequences and linkage to various immune effector molecules are shown in Table 2. These primers have been used, for example with the methods of Section I. A-C, to amplify and link TCR sequences to various immune effector molecules.

Example 2: High-Throughput Protocol for TCRβ Repertoire Library Construction

In one embodiment, a high-throughput protocol was implemented for human or mouse TCRβ repertoire library construction. The libraries were sequenced directly on the GAIIx next-gen sequencing platform (Illumina). For human samples, multiplex PCR was performed using a set of 20 primers to amplify across all 50 V segments and 10 primers to amplify across all 13 J segments. The primers libraries generated libraries that were the reverse complement of the native TCRβ sequence. This enabled sequencing from the J side of the constructs without further manipulation. The primers also had tails with the same sequence as a portion of the Illumina TruSeq library adapter. The 30 primers were pooled in a single 400 µl PCR, which contained genomic DNA from at least $5 \times 10^5$ cells. The reactions were then thermocycled for no more than 25 cycles, depending on the number of input cells. After thermocycling, a PCR column (Qiagen) was used to remove the primers. Next, a second round of PCR was performed, using an aliquot of the purified first round analyte and a set of universal primers. The universal primers for the second round of PCR annealed to the tails of the first primers, producing final PCR products that had the full Illumina sequencing adapter sequence fused to a library of TCRβ sequences. The universal primers also had barcode tags, which enabled multiplexing of dozens of samples in a single next-generation sequencing lane. Finally, the libraries were purified with gel size selection, and quantified with a quantitative PCR kit (Kapa Biosystems) prior to sequencing. Over 300 TCRβ libraries were built and sequenced using this protocol.

FIG. 31 shows a simplified workflow for high-throughput generation of TCRβ repertoire libraries. The first round used a set of 30 primers to amplify the full TCRβ repertoire and attaches universal priming regions. The second round amplified the repertoire with universal primers and added sequences for next-generation sequencing.

Example 3: Protocol Optimization Using 48-Plex Pool of TCRβ Plasmid Clones

The true content of any particular TCRβ repertoire is not known, so an endogenous TCRβ repertoire cannot serve as a gold standard for protocol optimization. A 48-plex pool of mouse TCRβ plasmid clones was designed to act as template for protocol optimization. First, multiplexed amplification was performed of the mouse TCRβ repertoire as described in Example 2. The PCR products were subcloned using the TOPO-TA vector (Life Technologies), transformed post ligation into TOP10 competent cells (Life Technologies), and 48 transformed colonies were picked. Next, the clones were sequenced by Sanger sequencing to identify the TCRβ clonotype sequences. All of the clones were unique, and represented a broad range of possible V-Jβ combinations. The plasmids were then mixed in a single tube, across three orders of magnitude and with six replicates at each concentration.

The 48-plex mixture was used to optimize the TCRβ amplification protocol. The purification methodology after the first and second PCR steps, the number of cycles in the first PCR, and the annealing temperature in the first PCR were optimized. WA PCR column or gel excision for the purification technology were used. Due to spurious mispriming, the first round of PCR produced multiple bands in addition to a major band in the target size range of 150-200 bp. Gel excision removed the undesired material, but the process was tedious and results in loss of up to 75% of the desired material. Protocols with fewer first PCR amplification cycles typically produce less severe amplification bias, whereas amplification bias is typically skewed in protocols with >30 cycles. Annealing temperature controls the stringency of priming events, with lower temperatures producing higher yields but less specificity.

68 Illumina libraries were constructed using the mixture of 48 plasmids and varying protocol parameters as described above. The libraries were sequenced on a next-generation sequencing machine (Illumina) to obtain >500 k paired-end 80 bp sequence tags for each library. To analyze the sequencing data, each 2×80 bp sequence tag was aligned to the sequences of the 48 known clonotypes to obtain the best match. The number of tags aligned to each plasmid for each library was counted, and then these results were correlated with the expected ratios of the input plasmid clones. A linear regression analysis to fit each data set was performed (see Table 1: yielding correlation, $R^2$ of 1, and a slope of 1. The protocol used 15 cycles of amplification for the first PCR, an annealing temperature of 61° C., PCR column purification after the first PCR, and gel purification following the second PCR.

TABLE 1

Analysis of selected pilot protocol optimization experiments. $R^2$ and slope were computed from a regression analysis between the observed count of sequences in each library versus the known input count. Conditions in row 3 (bold) are an example of an optimized protocol.

| 1st PCR Cycles | 1st PCR Ta | 1st PCR Cleanup | 2nd PCR Cleanup | R2 | Slope |
|---|---|---|---|---|---|
| 15 | 57 | column | gel | 0.56 | 0.54 |
| 15 | 59 | column | gel | 0.7 | 0.68 |
| 15 | 61 | column | gel | 0.72 | 0.71 |
| 15 | 63 | column | gel | 0.69 | 0.7 |
| 25 | 57 | column | gel | 0.47 | 0.43 |
| 25 | 59 | column | gel | 0.44 | 0.4 |
| 25 | 61 | column | gel | 0.45 | 0.45 |
| 25 | 63 | column | gel | 0.41 | 0.39 |
| 35 | 57 | column | gel | 0.47 | 0.41 |
| 35 | 59 | column | gel | 0.43 | 0.37 |
| 35 | 61 | column | gel | 0.42 | 0.4 |
| 35 | 63 | column | gel | 0.41 | 0.4 |

Example 4: TCRβ Repertoire Data Analysis

Because the TCRβ repertoire contains as many as $5 \times 10^6$ clonotypes, and CDR3 regions often differ by only a few nucleotides, a sophisticated custom analysis platform was necessary just to identify the clones in the library. The turnkey fast-alignment methods, such as BLAST (Altschul et al., 1990), BLAT (Kent 2002), and SOAP (Li et al., 2008), were inadequate for the task at hand, because they resulted in many spurious matches. Moreover, highly accurate turnkey methods such as Smith-Waterman (Smith and Waterman, 1981) were cumbersomely slow for this kind of analysis. Finally, all of these methods would require a huge reference library ($10^{15}$ diversity) of all possible CDR3 nucleotide sequences, which is a computational burden.

To address these problems, an algorithm was built that is faster than any current method by almost an order of magnitude, and which has the same accuracy as standard alignment methods. A table of 4-8 nucleotide "words" that uniquely identify the V and J segments of mouse or human within the amplified region is generated. The validity of each match is tested by identifying the distance to and the sequence of the second conserved cysteine. The match was accepted as correct only if both distance and sequence confirm the match. Using data from our TCRβ repertoire sequencing experiments, we typically identified ~99.98% of V-Jβ combinations unambiguously. The remaining reads were discarded.

We also employed two further quality control steps: (i) the CDR3 region must not contain any sequencing errors in the form of uncalled bases; and (ii) the CDR3 region is in frame as defined by the second conserved cysteine. If all quality tests are passed, the method identified the protein coding sequence of the CDR3 region within the known reading frame for that particular gene. This algorithm ensured speed, accuracy and lowest error rates. It can easily be adapted for use with other variable gene families, such as TCRα, or IgH.

A number of experiments were performed to demonstrate the utility of our protocols for deep TCRβ sequencing. Mouse bone marrow transplantations were performed in matched and mismatched genetic backgrounds. To determine the systemic impact of these transplantation events on the mice, the T cell repertoires of the colon were examined. The most common TCRβ clonotypes in colons from replicate mismatched bone marrow transplantations were more closely related than the most common TCR clonotypes in a colon from syngenic transplantation, especially in the top 1% of clones. Profiles of control colons were nearly identical in the top 1% of clonotypes. These data indicate that the protocols described herein produce quality, quantitative data of utility to research customers.

Example 5: Constructing a Control Library of TCRβ Clones and Optimizing PCR Conditions Using the Control Library Additional experiments are performed to build a library of 960 TCRβ clones that contains at least one representative from each of the 650 possible human V-Jβ combinations. This set of clones is used for molecular and statistical optimizations. A plasmid library of human TCRβ is generated as described above in Example 4. About 3,000 transformant colonies are picked and the clones are sequenced using standard capillary sequencing (e.g., Sequetech). The V-Jβ pairing corresponding to each sequenced clone is identified as described above in Example 4. The goal is to obtain at least one representative clone for each V-Jβ pair. If sequencing finds that some V-Jβ pairs are missing, those pairs are rescued by making libraries of TCRβ using only primers for those missing V-Jβ pairs, subcloning, and sequencing. After several rounds, clones are identified for every possible V-Jβ pair. These plasmids are mixed into a single template mixture, with 96 clones at each concentration and 10 different concentrations across three orders of magnitude.

Example 6: Optimizing PCR Conditions Using the Control Library

Previous experiments have shown that the first PCR amplification causes most of the amplification bias. Additional experiments are performed using the 960-clone pool and next-generation sequencing to further optimize first PCR cycle number. About 60 TCRβ libraries are generated from the plasmid mixture, with four replicates for each of the 15 cycle numbers between 10 and 25. The library mixtures are quantified and ~4 million sequences are obtained from each library a GAIIx next-gen sequencer (Illumina). The V-Jβ pairing corresponding to each sequenced clone as described above in Example 4, and the counts of sequence tags are tallied for each clone in each data set.

Prior work has shown that GC content can affect amplification efficiency (Markoulatos et al., 2002). The immense variety of V(D)Jβ combinations result in an assortment GC contents and lengths. The amplification bias is tested after addition of various reagents, such as betaine or magnesium chloride. Approximately 60 TCRβ libraries are generated from the plasmid mixture, with four replicates for each of 15 different buffers. The library mixtures are quantified and ~4 million sequences are obtained from each library using a GAIIx next-gen sequencer (Illumina). The V-Jβ pairing is identified corresponding to each sequenced clone as described above in Example 4, and the counts of sequence tags are tabulated for each clone in each data set.

Example 7: T Cell Analysis and Transplant Monitoring

Methods of the invention are applied to post-transplant immune monitoring. After an allogeneic transplant (i.e., kidney or liver), a host's T cells response to transplants are assessed to monitor the health of the host and the graft. Molecular monitoring of blood or urine is helpful to detect acute or chronic rejection before a biopsy would typically be indicated. For example, detection of alloantibodies to human leukocyte antigen (HLA) has been associated with chronic allograft rejection (Terasaki and Ozawa, 2004 *American Journal of Transplantation* 4:438-43). Other molecular markers include $b_2$-microglobulin, neopterin, and proinflammatory cytokines in urine and blood (Sabek et al., 2002 *Transplantation* 74:701-7; Tatapudi et al., 2004 *Kidney International* 65:2390; Matz et al., 2006 *Kidney International* 69:1683; Bestard et al., 2010 *Current Opinion in Organ Transplantation* 15:467-473). However, none of these methods has become widely adopted in clinical practice, perhaps due to low specificity and sensitivity. Prior work has shown that regulatory T cells (Treg) induce graft tolerance by down-regulating helper T cells (Th) (Graca et al., 2002 *Journal of Experimental Medicine* 195: 1641). Additionally, transplanting hematopoietic stem cells from HLA-mismatched donors into the recipient has resulted in long-term nonimmunosuppressive renal transplant tolerance up to 5 years after transplant (Kawai et al., 2008 *NEJM* 358:353-61).

Primers are designed that target transcripts from several immune functionality genes (described above), which produce overlap extension fusion constructs with CDR3β amplicons. In one embodiment, these primers are designed to specifically amplify cDNA by spanning RNA splice junctions and hybridize to cDNA from processed messenger RNA. Examples of molecules that are associated with immune function include, but are not limited to, T-BET and IFN-g, which indicate T helper 1 cells (Th1); GATA3 and IL-4, which indicate T helper 2 cells (Th2); IL-17, which indicates T helper 17 cells (Th17); and FoxP3 and IL-10, which indicate T regulatory cells (Treg). Such signaling molecules are members of large protein families with strong homology between paralogues, which may result in background amplification during PCR. Accordingly, nucleotide alignments of all of the paralogues in each family (i.e., all of the interleukin genes) are generated and PCR primers are designed that span exons and have the lowest possible sequence homology to other genes in the family.

Functional T cell monitoring involves the following steps: (i) isolation of single peripheral blood mononuclear cells in emulsion microdroplet reactors; (ii) overlap extension amplification of complexes between TCRβ and immune functionality molecules in microdroplet reactors; and (iii) emulsion reversal followed by bulk sequencing. The TCRβ and immune functionality primer sets will be combined to produce major amplicon fusion constructs from the minor amplicons. The overlap extension primers are a combination of the reverse TCRβ primers with approximately half of each immune functionality molecule forward primer, which results in a total of 91 fusion reverse TCRβ primers. The fusion primers between the forward primer for each immune functionality minor amplicon contain approximately half of each of the 13 TCRβ reverse primers, for a total of 91 fusion reverse immune functionality primers. The final result is that the overlap between any pair of TCRβ and immune functionality minor amplicons has a melting temperature of approximately 55-65° C., such that each minor amplicon acts as a primer for the paired amplicon. In the final reaction mixtures, the outer primers are diluted to a final concentration of 0.1 µM, and the inner primers are diluted to 0.01 µM, such that the inner primers are limiting reagents.

Example 8: T Cell Analysis and Latent Tuberculosis Diagnosis

Latent tuberculosis (TB) is a major global epidemic, affecting as many as 2 billion people worldwide. There is currently no reliable test for clinical diagnosis of latent TB. This technology gap has severe clinical consequences, since reactivated TB is the only reliable hallmark of latent TB. Furthermore, clinical trials for vaccines and therapies lack biomarkers for latent TB, and therefore must follow cohorts over many years to prove efficacy.

The major current vaccine for tuberculosis, bacillus Calmette-Guérin (BCG), is an unreliable prophylactic. In a meta-analysis of dozens of epidemiological studies, the overall effect of BCG was 50% against TB infections, 78% against pulmonary TB, 64% against TB meningitis, and 71% against death due to TB infection (Colditz et al., 1994 *JAMA* 271:698-702). Additionally, the rapid rise in multidrug resistant TB has increased the need for new vaccine and immunotherapy approaches. Up to 90% of infected, immunocompetent individuals never progress to disease, resulting in the huge global latent TB reservoir (Kaufmann, 2005 *Trends in Immunology* 26:660-67).

Since tuberculosis is a facultative intracellular pathogen, immunity is almost entirely mediated through T cells. Interferon-g expressing T helper 1 (Th1) cells elicit primary TB response, with some involvement by T helper 2 cells (Th2). After primary response, the bacteria become latent, controlled by regulatory T cell (Treg) and memory T cells (Tmem). Recently, eleven new vaccine candidates have entered clinical trials (Kaufmann, 2005 *Trends in Immunology* 26:660-67). These vaccines are all "post-exposure" vaccines, i.e., they target T cell responses to latent TB and are intended to prevent disease reactivation. Because of the partial failure of BCG to induce full immunity, rational design and validation of future TB vaccines should include systematic analysis of the specific immune response to both TB and the new vaccines.

For decades, the standard of care for diagnosis of latent tuberculosis has been the tuberculin skin test (TST) (Pai et al., 2004 *Lancet Infectious Disease* 4:761-76). More recently, two commercial in vitro interferon-g assays have been developed: the QuantiFERON-TB assay and the T SPOT-TB assay. These assays measure cell-mediated immunity by quantifying interferon-g released from T cells when challenged with a cocktail of tuberculosis antigens. Unfortunately, neither the TST nor the newer interferon-g tests is effective at distinguishing latent from cleared TB (Diel et al., 2007 *American Journal of Respir Crit Care Med* 177:1164-70). This is a significant problem because patients without clinical evidence of latent TB (i.e., visualization of granulomas) but with positive TST or interferon-g test typically receive 6-9 months of isoniazide therapy, even though this empiric intervention is unnecessary in patients who have cleared primary infection and can cause serious complications such as liver failure.

Prior work has demonstrated that T cell responses are used to distinguish latent from active TB (Schuck et al., 2009 *PLoS One* 4:e5590). The premise of this prior work is that immune cells directed against TB antigens will be expanded in the memory T cell population if the TB is latent, but expanded in a helper T cell fraction if the TB is active. Functional T cell sequencing is used to distinguish latent TB from cleared TB. The protocol involves: (i) capture of single T cells in emulsion microdroplets; (ii) microdroplet reverse transcription and amplification at target loci; (iii) microdroplet synthesis of fusion complexes between two or more target loci; and (iv) reversing emulsions and sequencing major amplicons with bulk sequencing. Sequence specific PCR is used after overlap extension RT-PCR to detect the presence of a particular biomarker for latent TB.

Example 9: T Cell Analysis and Diagnosing or Monitoring Disease

Similarly, functional T cell monitoring is used for diagnosis and monitoring of nearly any human disease. These diseases, include but are not limited, to systemic lupus erythmatosis (SLE), allergy, autoimmune disease, heart transplants, liver transplants, bone marrow transplants, lung transplants, solid tumors, liquid tumors, myelodysplastic syndrome (MDS), chronic infection, acute infection, hepatitis, human papilloma virus (HPV), herpes simplex virus, cytomegalovirus (CMV), and human immunodeficiency virus (HIV). Such monitoring includes individual diagnosis and monitoring or population monitoring for epidemiological studies.

T cell monitoring is used for research purposes using any non-human model system, such as zebrafish, mouse, rat, or rabbit. T cell monitoring also is used for research purposes using any human model system, such as primary T cell lines or immortal T cell lines.

Example 10: B Cell Analysis

Antibodies are produced by recombined genomic immunoglobulin (Ig) sequences in B lineage cells. Immunoglobulin light chains are derived from either κ or λ genes. The λ genes are comprised of four constant (C) region genes and approximately thirty variable (V) region genes. In contrast, the κ genes are comprised of one C region gene and 250 V region genes. The heavy chain gene family is comprised of several hundred V gene segments, fifteen D gene segments, and four joining (J) gene segments. Somatic recombination during B cell differentiation randomly chooses one V-D-J combination in the heavy chain and one V-J combination in either κ or λ light chain. Because there are so many gene segments, millions of unique combinations are possible. The V regions also undergo somatic hypermutation after recombination, generating further diversity. Despite this underlying complexity, it is possible to use dozens of primers targeting conserved sequences to sequence the full heavy and light chain complement in several multiplexed reactions (van Dongen et al., 2003 Leukemia 17: 2257-2317).

Any of the individual immunoglobulin subunits are linked to immune functionality molecules that indicate B cell activity or subpopulations. A first target nucleic sequence, a second target nucleic acid sequence or both target nucleic acid sequences can comprise an immunoglobulin sequence. Alternatively the first target nucleic acid sequence can comprise an immunoglobulin sequence, and the second sequence can comprise a second molecule associated with immune cell function. Examples of functional B cell marker molecules include, but are not limited to, major histocompatibility complex (MEW), cluster of differentiation 19 (CD19), interleukin 7 receptor (IL-17 receptor), cluster of differentiation 10 (CD10), cluster of differentiation 20 (CD20), cluster of differentiation 22 (CD22), cluster of differentiation 34 (CD34), cluster of differentiation 27 (CD27), cluster of differentiation 5 (CD5), and cluster of differentiation 45 (CD45), cluster of differentiation 38 (CD38), cluster of differentiation 78 (CD78), interleukin-6 receptor, Interferon regulatory factor 4 (IRF4), and cluster of differentiation 138 (CD138). A primer pool that amplifies the full IgH complement of B cells is combined with a single B cell marker primer pair. This assays all of the B cell clonotypes in a particular functional group, such as Bmem. Alternatively, a primer pool that amplifies the full IgH complement of B cells is combined with dozens of B cell marker primer pairs. This assay provides the full phenotype for each clonotype in the cell mixture.

A method is provided for linking IgH and Igκ. IgH and Igλ are linked in single cells to immune functionality molecules that indicate B cell activity or subpopulations. The vast majority of diversity in the B cell repertoire is comprised of the V-D-J regions of IgH and V-J regions of Igκ (Sandberg et al., 2005 Journal of Molecular Diagnostics 7:495-503; Boyd et al., 2009 Science Translational Med 1: 12ra23). Previously-reported primer pools (van Dongen et al., 2003 Leukemia 17: 2257-2317) are used to amplify these regions of IgH and Igκ. Five primer pools in separate reactions are used to amplify the IgH and Igκ complement of a healthy human. The amplified material sequenced with bulk sequencing. To analyze the bulk sequencing results, the IgBLAST algorithm and database is used to determine the V-D and D-J junctions of IgH and align the IgH and Igκ sequences to germ line gene segments. Overall, this method is more highly parallelized than previously-reported methods for single cell Ig analysis (U.S. Pat. No. 7,749,697).

Example 11: B Cell Analysis and Drug Discovery

Antibody therapeutics are increasingly used by pharmaceutical companies to treat intractable diseases such as cancer (Carter 2006 Nature Reviews Immunology 6:343-357). However, the process of antibody drug discovery is expensive and tedious, requiring the identification of an antigen, and then the isolation and production of monoclonal antibodies with activity against the antigen. Individuals that have been exposed to disease produce antibodies against antigens associated with that disease, so it is possible mine patient immune repertoires for antibodies that could be used for pharmaceutical development. However, a functional monoclonal antibody requires both heavy and light chain immunoglobulins. Overlap extension PCR and/or overlap extension RT-PCR in single cell emulsion microdroplets is used to capture functional antibody sequences from patient B cell repertoires. Briefly, the method involves the following steps: (i) isolation of single B cells in aqueous-in-oil microreactors using a microfluidic device; (ii) molecular linkage between heavy and light chain immunoglobulin (IgH and Igκ) amplicons inside the single cell microreactors; and (iii) reversal of the emulsions followed by bulk sequencing of the linked polynucleic acid sequences. This produces heavy and light chain pairings from millions of single B cells analyzed in parallel, which are mined as potential therapeutic agents.

The fusion primer sequences for overlap extension PCR and overlap extension RT-PCR are identical to the independent IgH and Igκ primers, except certain primers contain additional polynucleotide sequences for overlap extension: (i) the forward primer of the IgH locus has a random 10-20 nt sequence with no complementarity to either target; (ii) the reverse primer of the IgH loci has a 10-20 nt sequence with complementarity to the forward primer of Igκ, and (iii) the forward primer of Igκ has complementarity to the reverse primers for the IgH locus. In the final reaction mixtures, the outer primers are diluted to a final concentration of 0.1 μM, and the inner primers are diluted to 0.01 μM, such that the inner primers will be a limiting reagent. This drives formation of the major amplicon.

Example 12: B Cell Analysis and Monitoring Immunity

Humoral memory B cells (Bmem) help mammalian immune systems retain certain kinds of immunity. After exposure to an antigen and expansion of antibody-producing cells, Bmem cells survive for many years and contribute to the secondary immune response upon re-introduction of an antigen. Such immunity is typically measured in a cellular or antibody-based in vitro assay. In some cases, it is beneficial to detect immunity by amplifying, linking, and detecting IgH and light chain immunoglobulin variable regions in single B cells. Such a method is more specific and sensitive than current methods. Massively parallel B cell repertoire sequencing is used as described in Example 13 to screen for Bmem cells that contain a certain heavy and light chain pairing which is indicative of immunity. In another exemplary method, single cell heavy and light chain pairing are combined with functional B cell sequencing, i.e., developing overlap extension RT-PCR primers that target RNA transcripts that are overrepresented in Bmem cells (i.e., CD27). By combining light and heavy immunoglobulin amplification with gene expression of Bmem or plasma cell immune function transcripts, sorting cells by FACS or other tedious methods are avoided.

Example 13: B Cell Analysis and Diagnosing and Monitoring Disease

B cell monitoring is used for diagnosis and monitoring of nearly any human disease. These diseases include, but are not limited to, systemic lupus erythmatosis (SLE), allergy, autoimmune disease, heart transplants, liver transplants, bone marrow transplants, lung transplants, solid tumors, liquid tumors, myelodysplastic syndrome (MDS), chronic infection, acute infection, hepatitis, human papilloma virus (HPV), herpes simplex virus (HSV), cytomegalovirus (CMV), and human immunodeficiency virus (HIV). Such monitoring could include individual diagnosis and monitoring or population monitoring for epidemiological studies.

B cell monitoring is also used for research purposes using any non-human model system, such as zebrafish, mouse, rat, or rabbit. B cell monitoring is used for research purposes using any human model system, such as primary B cell lines or immortal B cell lines.

Example 14: Methods for Noninvasive Prenatal Diagnosis

In the absence of prenatal diagnosis, approximately 2% of babies have serious physical or mental handicaps, approximately 3.3% of babies have some form of congenital malformation, and approximately 0.5% have a phenotypically-significant chromosome abnormality. Current clinical methods for prenatal diagnosis are invasive and carry significant risks to the fetus, restricting their use to patients of advanced maternal age. Noninvasive, accurate technologies are needed for first trimester prenatal genetic diagnosis. Most current preclinical methods for noninvasive prenatal diagnosis capture and diagnose circulating fetal cells. These methods rely on cell surface proteins and/or cell morphology to enrich for particular populations of fetal cells. Such flawed approaches have failed to reach the clinic despite decades of intense research and development.

Isolation of circulating fetal nucleated red blood cells (FNRBCs) from maternal blood is one approach to noninvasive prenatal diagnosis. Nucleated red blood cells are among the first hematopoietic cell types produced during fetal development. These cells cross the placenta and are detectable at low concentrations in maternal blood during the first trimester (Ganshirt et al., 1994 *Lancet* 343:1038-9). Another attractive feature of FNRBCs is their short lifespan compared to other circulating fetal cell types (Pearson, 1967 *Journal of Pediatrics* 70:166-71), making them unlikely to persist in maternal blood from previous pregnancies.

The scarcity of circulating fetal cells, estimated at one fetal cell per $10^5$-$10^9$ maternal cells (Price et al., 1991 *Am J Obstet Gynecol* 165:1731-7; Ganshirt-Ahlert et al., 1994 *Clin Genet* 38:38-43), necessitates the use of sensitive and specific fetal cell enrichment methods prior to diagnosis. Widely-adopted enrichment methods include combinations of density gradient centrifugation (Samura et al., 2000 *Prenat Diagn* 20:281-6), fluorescence activating cell sorting (FACS), and magnetic cell sorting (MACS) (Busch et al., 1994 *Ann NY Acad Sci* 731: 144-6). Despite the development of these methods, none have been commercialized.

i. Methods for Noninvasive Prenatal Diagnosis of Single Gene Disorders

LCR or padlock probes are used to capture and amplify paternal-specific alleles in an allele-specific manner and to perform overlap extension PCR to detect disease alleles (FIGS. 26-30). The method involves the following steps: (i) parental genotyping to find paternal-specific polymorphisms; (ii) isolation of single mononuclear cells from maternal blood into emulsion microdroplets; (iii) amplification of disease and paternal-specific "linker" loci by a modified LCR/PCR protocol in emulsion microdroplet reactors; (iv) overlap extension amplification of complexes between disease and linker loci in microdroplet reactors; (v) recovery of linked complexes by emulsion reversal; and (vi) massively parallel sequencing. The massively parallel sequencing data are analyzed to quantify instances of linked genotypes. Only microdroplet reactors that contain single fetal cells yield linked complexes between the disease locus and the paternal-specific allele. Both alleles amplify from the fetal cell, providing the physician with status as a carrier, homozygous normal, or homozygous affected.

LCR probes are designed to target a locus associated with a disease and a linker SNP locus. The LCR probes are 20-30 nucleotides long and have melting temperatures (Tm) of approximately 55-65° C. The 5' nucleotides are phosphorylated, and probes are designed to minimize probe self-complementarity, as well as complementarity between probes. In addition to regions of complementarity to target loci, three of the probes include polynucleotide sequences that enable amplification after ligation: (i) the 5' probe for the disease locus have a random 10-20 nt sequence with no complementarity to either target locus; (ii) the 3' probe for the disease locus has a 10-20 nucleotide sequence with complementarity to the 5' end of the linker SNP locus; and (iii) the 5' probe for the linker SNP locus have complementarity to the 3' end of the disease locus (FIGS. 26-30).

For each disease and linker locus pair, a reaction mixture is formulated using cell line genomic DNA, the LCR probes, the PCR primers, Ampligase (Epicentre), Stoffel fragment DNA polymerase (Life Technologies), and reaction buffer (after Hardenbol et al., 2005; 20 mM Tris-HCl, 25 mM KCl, 10 mM $MgCl_2$, 0.5 mM NAD, 0.01% Triton X-100). The "inner" probes are added at $\frac{1}{10}^{th}$ of the concentration of the other oligonucleotides in the reaction. For the initial annealing and ligation, the mixtures are incubated for 4 minutes at 20° C., 5 minutes at 95° C., and 15 minutes at 60° C. Then, standard PCR thermocycling conditions are used to amplify the minor and major amplicons (e.g., 95° C., 5 minutes; [95° C., 30 seconds; 60° C., 30 seconds; 72° C., 30 seconds]×30 cycles).

After bulk sequencing of the major amplicons, disease and unaffected alleles are analyzed to diagnose the fetus as homozygous normal, heterozygous carriers, or homozygous affected. In heterozygous carriers, major amplicons linked to the paternal-specific allele comprise approximately 50% disease alleles and 50% normal alleles. Similarly, in homozygous carriers, major amplicons linked to the paternal-specific allele comprise of nearly 100% disease alleles. This method can be extended beyond single nucleotide mutations to find paternal-allele specific gene expression patterns and/or multiplexed analysis of many germline mutations in circulating fetal cells.

Examples of genes that are often mutated and are of interest in prenatal diagnostics include, but are not limited to, cystic fibrosis transmembrane receptor (CFTR), aspartoacylase (ASPA), Fanconi anemia, complementation group C (FANCC), Glucose-6-phosphatase (G6CP), Glucocerebrosidase (GBA), Hexosaminidase A (HEXA), hemoglobin beta (HBB), Frataxin (FXN), low density lipoprotein receptor (LDLR), and methyl CpG binding protein 2 (MECP2).

For example, in FIG. 26, single cell sequence linkage by ligase chain reaction combined with overlap extension polymerase chain reaction is illustrated, as applied to a method for noninvasive prenatal diagnosis. The target nucleic acid (g) is a paternal-specific allele, the target nucleic acid (h) is a first disease allele, and the target nucleic acid (i) is a second disease allele. Notably, both alleles (h) and (i) are amplified in any cell (j) that contains the paternal-specific variant, and no major amplicons are produced in cells that lack the paternal-specific nucleotide variant. Primer (a) is a forward LCR probe and primer (b) is a reverse LCR probe for amplifying target nucleic acid (g). Primer (e) is a forward PCR primer and primer (f) is a reverse PCR primer for both disease alleles (h) and (i). The forward primer targeting the disease locus has a region of complementarity to the reverse probe targeting the paternal-specific nucleotide variant. The process can be carried out in an emulsion droplet or reaction container (k). FIG. 27 also shows an example of hybridization of primers and target nucleic acids in a single cell sequence linkage by ligase chain reaction combined with overlap extension polymerase chain reaction, as applied to a method for noninvasive prenatal diagnosis, according to one embodiment of the invention. The process is carried out in an emulsion droplet or reaction container (k).

Moreover, FIG. 28 shows an example of resulting amplicons produced in a single cell sequence linkage by ligase chain reaction combined with overlap extension polymerase chain reaction, as applied to a method for noninvasive prenatal diagnosis, according to one embodiment of the invention. FIG. 29 shows hybridization of overlapping complementary regions of the resulting amplicons, and overlap extension polymerase chain reaction, as applied to a method for noninvasive prenatal diagnosis, according to one embodiment of the invention. FIG. 30 illustrates the resulting amplicons that are produced from the overlap extension polymerase chain reaction, as applied to a method for noninvasive prenatal diagnosis. The end product is a library of "major amplicons," or linked loci, which can then be sequenced in bulk.

ii. Methods for Noninvasive Prenatal Molecular Karyotyping

Methods for genetic disease detection are adapted for noninvasive prenatal molecular karyotyping. Such a method involves the following steps: (i) parental genotyping to find paternal-specific polymorphisms; (ii) isolation of single mononuclear cells from maternal blood into emulsion microdroplets; (iii) amplification of disease and paternal-specific "linker" loci by a modified LCR/PCR protocol in emulsion microdroplet reactors; (iv) overlap extension amplification of complexes between tens to thousands to hundreds of thousands of chromosomal probes and linker loci in microdroplet reactors; (v) recovery of linked complexes by emulsion reversal; and (vi) massively parallel sequencing. The massively parallel sequencing data are analyzed to quantify instances of linked genotypes. Only microdroplet reactors that contain single fetal cells yield linked complexes between the chromosomal probes and the paternal-specific allele. The chromosomal probes are used to quantify the number of chromosomes or chromosome segments present in the fetal cells, and, by association, the fetus. Chromosome copy number is quantified by comparing sequence counts from an unknown chromosome to sequence counts from a known reference chromosome within a single experiment, or by looking for allelic imbalance (Johnson et al., 2010 Human Reproduction 25:1066-75). This method is also used to detect a variety of chromosome disorders, including aneuploidy, unbalanced structural chromosome disorders, microdeletions, microinsertions, and other kinds of congenital disorders. Examples of disorders of interest include Trisomy 13, Trisomy 18, and Trisomy 21.

Example 15: Methods of Noninvasive Cancer Diagnosis

The medical community has long sought noninvasive diagnosis and monitoring of cancer patients, and there is already an FDA-approved method (CellSearch, Veridex) for quantification of circulating tumor cells for breast and prostate cancer patients. Noninvasive methods for diagnosis can enable molecular staging of tumors prior to biopsy, which can both reduce cost and lead to better clinical outcomes. After treatment, noninvasive methods are used to assess the success of the treatment regimen without the need for invasive and expensive re-biopsy. There is general consensus among clinicians that noninvasive methods for characterization of tumors would greatly benefit patients and increase the probability of favorable outcomes.

Single cell overlap extension PCR, LCR, padlock probes, and/or RT-PCR are used to specifically analyze only tumor cells in heterogeneous cell populations, such as cerebrospinal fluid (CSF) or blood (FIGS. 18-25). Unlike current methods, this approach completely bypasses the complexities caused by differences in cell surface markers and morphology. Such methods are particularly useful in cancers where a biopsy is invasive and expensive, and the treatment decisions, such as pharmacological therapy decisions, would benefit from molecular analysis of the tumor. The technology is used for any kind of tumor or any kind of genetic problem or combination of genetic problems in tumors.

The methods described above in Sections I and II also are used to detect a gene or SNP associated with cancer. Single cell overlap extension PCR, LCR, padlock probes, and/or RT-PCR is used to amplify a first nucleic acid or a second nucleic acid that is associated with cancer. The first target nucleic acid includes a rare somatic mutation and the second target is a gene transcript associated with cancer. Alternatively, one sequence is a molecular barcode and the second sequence is either a rare mutation sequence or a gene transcript associated with cancer. In either alternative, higher levels of multiplexing produce single-cell expression patterns for 10, 100, 1000, 10,000 transcripts or even all transcripts in the cell. Higher levels of multiplexing also can produce mutation profiles for entire genes, or many entire genes, or even the entire genome. The rare gene sequence is present in fewer than 5% of the cells, fewer than 1% of the cells, or fewer than 0.1% of the cells. The rare gene sequence results from a genetic mutation. The genetic mutation can be a somatic mutation. The genetic mutation can be a mutation in a gene selected from the group consisting of: epidermal growth factor receptor (EGFR), phosphatase and tensin homolog (PTEN), tumor protein 53 (p53), MutS homolog 2 (MSH2), multiple endocrine neoplasia 1 (MEN1), adenomatous polyposis coli (APC), Fas receptor (FASR), retinoblastoma protein (Rb1), Janus kinase 2 (JAK2), (ETS)-like transcription factor 1 (ELK1), v-ets avian erythroblastosis virus E26 oncogene homolog 1 (ETS1), breast cancer 1 (BRCA1), breast cancer 2 (BRCA2), hepatocyte growth factor receptor (MET), ret protoco-oncogene (RET), V-erb-b2 erythroblastic leukemia viral oncogene homolog 2 (HER2), V-Ki-ras2 Kirsten rat sarcoma viral oncogene homolog (KRAS), B-cell lymphoma 2 (BCL2), V-myc myelocytomatosis viral oncogene homolog (MYC), neurofibromatosis type 2 gene (NF2), v-myb myeloblastosis viral oncogene homolog (MYB), and mutS homolog 6 (*E. coli*) (MSH6). The cancer-associated transcript is a gene selected from the group consisting of epidermal cell adhesion molecule (EpCAM), V-erb-b2 erythroblastic leukemia viral oncogene homolog 2 (HER2), estrogen receptor (ER), Signal transducer and activator of transcription 3 (STAT3), CCAAT-enhancer-binding proteins (C/EBP), prostate-specific antigen (PSA), androgen receptor (AR), progesterone receptor (PR), Jun B (JUNB), Ras-related protein Rab-31 (RAB31), Early growth response protein 1 (EGR1), B-cell lymphoma 2 (BCL2), Protein C-ets-1 (ETS1), FBJ murine osteosarcoma viral oncogene homolog (c-Fos), and Insulin-like growth factor 1 (IGF-1). Signal transducer and activator of transcription 2 (STAT2) (Irgon et al., 2010 *BMC Cancer* 10: 319).

The cancer-associated transcripts can multiplexed to produce a signal from 10, 100, 1000, 10,000 transcripts, or all of the transcripts in the cell, which is analyzed by next-generation sequencing to identify a mutation. The mutation is associated with cancer. The cancer is selected from the group consisting of lung carcinoma, non-small cell lung cancer, small cell lung cancer, uterine cancer, thyroid cancer, breast carcinoma, prostate carcinoma, pancreas carcinoma, colon carcinoma, lymphoma, Burkitt lymphoma, Hodgkin lymphoma, myeloid leukemia, leukemia, sarcoma, blastoma, melanoma, seminoma, brain cancer, glioma, glioblastoma, cerebellar astrocytoma, cutaneous T-cell lymphoma, gastric cancer, liver cancer, ependymona, laryngeal cancer, neck cancer, stomach cancer, kidney cancer, pancreatic cancer, bladder cancer, esophageal cancer, testicular cancer, medulloblastoma, vaginal cancer, ovarian cancer, cervical cancer, basal cell carcinoma, pituitary adenoma, rhabdomyosarcoma, and Kaposi sarcoma.

The methods in this Example can be applied in an assay using intact mammalian cell mixtures to detect cancer cells. The non-small cell lung carcinoma cells CRL-5908 (ATCC) is used as a cancer model and Jurkat cells are used as a stand-in for primary lymphocytes. CRL-5908 has an L858R point mutation in EGFR, and expresses EpCAM. Jurkat does not express EpCAM (Landolin et al., 2010). Cell mixtures are created at six CRL-5908:Jurkat ratios between of 0% and 1%. Cells are encapsulated from the mixtures with beads into a lysis mix, and then merged with a stream containing a RT-PCR mix using the methods described above. The cells are diluted such that the cell distribution follows Poisson statistics with $\lambda=1.5$, and ~44% of the droplets with cells have multiple cells. Using this method, >1 million droplets are generated in each of six replicate experiments for each cell mixture. A fast-speed camera is used to obtain bead and cell encapsulation rates. The major amplicons are purified by gel electrophoresis and sequenced by next-generation sequencing to obtain at least 10 million sequence tags for each library.

Detecting cancer cells in these cell mixtures requires a special analytical framework. Sequencing generates counts of mutated EGFR and EpCAM linked to each barcode, and the barcodes are traced back to cells. If each droplet contains a single cell only, then these counts are used to directly quantify the percentage of CRL-5908 in the cell mixture. However, there may be an arbitrary number of cells encapsulated in droplets according to a Poisson distribution, resulting in many droplets with multiple cells.

Therefore, for such analysis, an algorithm is used that computes the number of cancer cells in a sample given counts of cancer markers such as mutated EGFR or EpCAM and statistics for cell encapsulation Poisson $\lambda$. To test the validity of this algorithm and to estimate the limits of detection that encapsulation of multiple cells per droplet imposes, the process of encapsulation is simulated, and the ratio of cancer marker expression in cancer cells to normal cells is determined. A Poisson distribution for the cell encapsulation rate is assumed, log-normally distributed expression levels over a fixed background, and the signal-to-noise ratio (SNR) is defined as the ratio of the mean expression level to the mean background. This simulation indicates a <1% error rate in a scenario where ~44% of droplets containing cells will have multiple cells ($\lambda=1.5$) and SNR=10.

Example 16: Noninvasive Gene Expression Analysis in Glioblastoma Multiforme

Certain genes are co-expressed specifically only in circulating tumor cells, so linkage of two tumor-specific transcripts in the same cell is a potentially powerful method for detection of circulating tumor cells in peripheral blood or CSF. The method enables noninvasive molecular staging of glioblastoma multiforme (GBM). GBM is the most common type of primary malignant brain tumor, with an incidence of 16,000 new cases per year in the United States. After characterization by magnetic resonance imaging (MRI) and clinical work-up, molecular characterization of biopsies is often performed to guide treatment regimens. There is growing consensus that distinct molecular categories of tumor should be subjected to distinct targeted treatment regimens (Mischel et al., 2003 *Cancer Biol Ther* 2:242-247). Prior GBM research has indicated that poor prognosis is indicated by coexpression of the genes C/EBPβ and STAT3 (Carro et al., 2010 *Nature* 463:318-26). These transcripts are not coexpressed in normal tissues. However, biopsies of GBM are highly invasive and expensive, so there is clinical demand for minimally invasive methods for molecular staging.

The method involves the following steps: (i) isolation of mononuclear cells from CSF (Spriggs 1954; *Journal of Clinical Pathology* 7:122) with emulsion microdroplet technology; (ii) reverse transcriptase polymerase chain reaction targeting C/EBPβ, STAT3, and a linker barcode sequence unique to each microdroplet; (iii) overlap extension amplification of complexes between C/EBPβ, STAT3, and the linker sequence; (iv) recovery of linked complexes by emulsion reversal; and (v) digital quantification of fusion complexes using next-generation sequencing. Only microdroplet reactors that contain tumor cells co-expressing C/EBPβ and STAT3 yield large numbers of complete linked complexes. Though next-generation sequencing pools all analytes from all cells, linker barcode sequences enable the trace back of gene expression to single cells. The final result is digital quantification of multiple linked transcripts that are traced back to millions of single cells analyzed in parallel.

The method also provides cDNA synthesis and PCR in emulsion microdroplets without buffer exchange or reagent addition between the molecular steps. Thermostable reverse transcriptase (RT) enzymes are used that withstand temperatures >95° C., such as ThermoScript RT (Lucigen) and GeneAmp Thermostable rTth (Life Technologies). In addition to primer regions targeting C/EBPβ and STAT3 (FIGS. 18-25), three of the primers in the set include polynucleotide sequences that enable amplification of a fusion complex: (i) the 5' primer of the C/EBPβ locus has a random 10-20 nt sequence with no complementarity to either target locus; (ii) the 3' primer of the C/EBPβ locus has a 10-20nt sequence with complementarity to the 5' end of the linker barcode oligonucleotide; (iii) the 5' probe of the STAT3 locus has complementarity to the 3' end of the linker. Two more oligonucleotides act as forward and reverse PCR primers to specifically amplify the linker barcode oligonucleotide. The "inner" primers of the STAT3 and C/EBPβ loci (i.e., the reverse primer for C/EBPβ and the forward primer for STAT3) are at limiting concentration, i.e., 0.01 µM for the inner primers and 0.1 µM for all other primers. This drives amplification of the major amplicon preferentially over the minor amplicons.

After emulsion reversal, the major amplicons are subjected to bulk sequencing. The barcode is linked to C/EBPβ and STAT3 sequences, and are used to trace back the major amplicons to a single cell (FIGS. 18-25). With trace back of each sequence to an original single cell, it is possible to tabulate genetic data for each single cell, which then enables single cell transcript quantification, i.e., single cell gene expression levels which are translated to a clinically actionable diagnosis.

Example 17: Molecular Karyotyping

Often structural chromosome changes, such as loss of heterozygosity (LOH) or gain of full chromosomes or segments thereof, will lead to progression of a tumor (Parsons et al., 2008 *Science* 321:1807-1812). Clinicians often examine the karyotype of a tumor to formulate a prognosis and treatment regimen. The methods outlined above are adapted to analyze both gene expression and detect chromosome abnormalities for any tumor type in a single multiplexed reaction.

A mutant cancer sequence is linked to probes to determine chromosome copy number or structural chromosome aberrations. Such a method involves the following steps: (i) isolation of single mononuclear cells from blood into emulsion microdroplets; (ii) amplification of chromosome probes and cancer mutation "linker" loci by a modified LCR/PCR protocol in emulsion microdroplet reactors; (iii) overlap extension amplification of complexes between chromosomal probes and mutant linker loci in microdroplet reactors; (iv) recovery of linked complexes by emulsion reversal; and (v) massively parallel sequencing.

The massively-parallel sequencing data is analyzed to quantify instances of linked genotypes. Only microdroplet reactors that contain cells with cancer mutations yield linked complexes between the chromosomal probes and the cancer-specific sequence. The chromosomal probes are used to quantify the number of chromosomes or chromosome segments present in circulating cancer cells, and, by association, the tumor. Chromosome copy number is quantified by comparing sequence counts from an unknown chromosome to sequence counts from a known reference chromosome within a single experiment, or by looking for allelic imbalance (Johnson et al., 2010 Human Reproduction 25:1066-75). This method is also used to detect a variety of chromosome disorders, including aneuploidy, unbalanced structural chromosome disorders, microdeletions, microinsertions, and other kinds of congenital disorders. The chromosome probes are linked to a barcode sequence rather than a cancer mutation, such that massively parallel sequencing measures chromosomal disorders in all of the cells in the assay rather than just cells that harbor a particular mutation.

Example 18: Somatic Cell Mutations

Often somatic cell mutations, i.e., in tumor promoter genes such as p53, p16, and/or EGFR, contribute to the progression of cancer (Parsons et al., 2008 *Science* 321: 1807-1812). Clinicians often analyze tumors for such known somatic cell mutations to formulate a prognosis and treatment regimen. In particular, somatic cell mutations are often indicative of progression to more aggressive stages of a tumor. The methods described above are adapted to analyze gene expression, somatic cell mutations, and/or chromosomal changes for any tumor type in multiplexed emulsion microdroplet reactions on millions of single cells in parallel. If somatic cell mutations are known, a molecular barcode is not necessary because allele-specific LCR or padlock probes are used to specifically amplify major amplicons only in cells that harbor the somatic cell mutation.

Any combination of gene expression, molecular karyotyping, and somatic cell mutation analysis is carried out in single tumor cells in heterogeneous cell populations. For example, LCR or padlock probes are used to affect allele-specific locus capture and major amplicon amplification only in cells with a particular somatic cell mutation. This method is an alternative to the molecular barcode method described above at least at Section B.6), achieving tumor cell-specific genetic analysis in a highly heterogeneous mixed background of cells. The allele-specific somatic cell mutation amplification are linked to RNA transcripts associated with disease outcomes and/or probes for quantification of loss of heterozygosity (LOH) or regional duplications in chromosome. The method is used to analyze co-expression of two or more microRNA sequences in single cells, or co-expression of a microRNA with another transcript, a methylated DNA sequence, or somatic cell mutation.

Example 19: Methods of Chimeric Cell Population Analysis

Certain applications require multiplexed analysis of cell populations that are chimers between two organisms. For example, after hematopoietic stem cell (HSC) transplantation, the host's T and B cells are chimeric between the host and graft. PCR amplification in a chimeric cell population of a variable genetic locus combined with some kind of functional genetic locus, such as an RNA transcript, enables analysis of the functional genetic locus in an individual-specific manner.

The methods described herein are applied to nonmyeloablative hematopoietic stem cell transplantation. Physicians lack powerful tools for monitoring patients after nonmyeloablative allogeneic hematopoietic stem cell (HSC) transplants (Pollack et al., 2009 *American Journal of Clinical Oncology* 32:618-28). After nonmyeloablative transplantation, the host immune system is a chimera between host and graft T cells. The chimera is a poorly characterized tissue, and chimeric instability is associated with poor outcome. The balance of donor-recipient immune reconstitution appears to influence a number of transplant immunological outcomes, including graft-versus-tumor effect (GVT), graft-versus-host disease (GVHD), and susceptibility to infection. T cells appear to play a major role in mediating each of these processes through adaptive immunity and T cell receptor (TCR) antigen recognition. Doctors currently lack tools for monitoring host and graft T cell identity after HSC transplant. Such methods are used to directly monitor GVT, GVHD, and response to infections (Kristt et al., 2007 *Bone Marrow Transplantation* 39:255-68).

A method is used to monitor chimeric T cell populations. For T cell chimerism analysis, TCRβ and host- and graft-specific single nucleotide polymorphisms (SNPs) are linked by overlap extension PCR or overlap extension RT-PCR in single cell microdroplets. This method involves the following steps: (i) genotyping to find SNPs specific to the graft and host; (ii) post-transplant isolation of single cells from host blood in emulsion microdroplets; (iii) overlap extension PCR amplification of fusion complexes between SNPs and TCRβ in microdroplet reactors; and (iv) recovery and sequencing of SNP-TCRβ linkage complexes by emulsion reversal. The result is a library of TCRβ sequences with linkage to host or graft. The TCRβ sequences are correlated with clinical outcomes over time.

Similar types of analysis are carried out using LCR, multi-probe circularization, or padlock probes, or any combination thereof. Also, other types of variant sequences, such as STRs, are also useful to indicate cell source in a chimeric population of cells. The T cell chimerism analysis is adaptable to applications such as B cell analysis or any other subpopulation of mononuclear cells in blood. Additionally, the method is combinable with functional T cell sequencing to indicate the immune activity of particular T cell clones.

There are many applications for chimeric cell population analysis outside of the field of medicine. For example, an investigator may create chimeric organisms, such as fruit flies, mice, or rats, which are chimers between multiple individuals with different genetic backgrounds, or even between multiple species. Chimeric cell populations for RNA transcripts, DNA methylation, somatic cell mutations, presence of a recombinant gene, or a variable DNA region are also capable of analysis with this method. Thus methods for analysis of chimeric T and B cell populations are adapted to other organisms and other kinds of cell populations. Additionally, such methods are used for allogeneic or autologous cellular therapeutics. Currently physicians lack powerful tools for monitoring patients after immune cells have been introduced either from a donor or as previously harvested from the patient. T cells, B cells, or NK cells are monitored to establish characteristics and efficacy of therapy.

Example 20: Methods for Gene Regulatory Sequence Analysis

Variants in regulatory DNA have an impact on expression levels of RNA transcripts (Brown et al., 2007 *Science* 317:1557-60). Functional screens of regulatory variants are time-consuming and expensive. In one exemplary method, the method includes mutagenizing cells, capturing single cells in aqueous-in-oil microdroplets, and then fusing an amplified putative regulatory locus with RNA transcripts from the nearby gene. In this way, mutations in regulatory sequences could be linked with gene expression levels.

Often an investigator wishes to understand how genomic nucleic acid sequences impact expression of transcripts. Because many nucleotides impact gene expression, these experiments are tedious. Ideally, an investigator would want to analyze quantitative gene expression at the single cell level as a function of mutagenized regulatory sequences. Suspected regulatory sequences are mutagenized to create a library of variable regulatory sequences. Then, a combination of overlap extension PCR and overlap extension RT-PCR in single cell emulsion microdroplets is used to link regulatory DNA sequence to RNA transcript levels. In this way, the effect of regulatory sequence mutagenesis on RNA transcript levels is measured in single cells.

Example 21: Methods for Molecular Haplotyping

Many kinds of genetic analysis, such as PGD or whole genome association studies, benefit from haplotype linkage of several genetic loci in DNA derived from a single sperm cell. In one exemplary method, single sperm cells are captured in aqueous-in-oil microdroplets, and then several variable genetic loci are fused in the cells, such as SNPs or STRs. This enables massively parallel molecular phasing.

An method for phasing of two loci is provided. Haplotypes millions of single sperm are analyzed in parallel. The method involves the following steps: (i) isolation of single sperm cells using emulsion microdroplet technology; (ii) amplification of two genetic variants by PCR in microdroplet reactors; (iii) overlap extension PCR amplification of fusion complexes between the variants in microdroplet reactors; and (iv) recovery of linked complexes by emulsion reversal. The result is a library of phased haplotypes, which are then sequenced using next-generation sequencing.

An alternate method for phasing of multiple loci is provided in this paragraph. In some cases, phasing of only two loci is not adequate for improvement of whole genome association studies or other kinds of analysis. In such situations, molecular methods such as LCR or padlock probes, which enable higher probe multiplexing, are used as an alternative. Additionally, a variety of PCR primer pairs are affixed to beads, such that thousands of PCR primer pairs are distributed to emulsion microdroplets that contain a single bead and a single sperm cell.

Example 22: Methods of Detecting Directed Molecular Evolution

Some kinds of industrial applications require improved enzymes and/or biological strains to optimize engineered biosystems. For example, enzymes that degrade a particular kind of industrial waste might not be found in nature, but in vitro evolution of existing enzymes might result in an optimized enzyme. Many such processes benefit from molecular genetic analysis of multiple loci in millions of single cells analyzed in parallel.

Yeast Evolution

Industrial in vitro evolution often involves mutagenesis of cells followed by growth in selective media. In an exemplary method, yeast cells are mutagenized and grown on special media containing xylose as the primary food source. The single yeast cells are captured in aqueous-in-oil microdroplets, and then several metabolic pathway genes are sequenced. At least one company (Microbiogen, Sydney, AUS) is developing yeast strains for growth on xylose, but is using slow, traditional screening methods.

Other Applications

Many groups are currently researching methods for improving natural strains of algae and bacteria for the purpose of biofuel production. The methods for linked genotyping and/or single cell gene expression analysis are used to enable in vitro evolution of these organisms for the purpose of biofuel or other kinds of energy production.

Example 23: Other Applications and Derivative Methods

Agriculture

All of the clinical methods described above (e.g., T cell sequencing and B cell sequencing) are applicable to animals. These animals include, but are not limited to, cows, pigs, chickens, or salmon, etc. In particular, livestock and other agricultural animals suffer from infectious disease, which results in considerable economic hardships. The methods described herein are adaptable to improve monitoring and detection of infectious disease in an agricultural setting.

Metagenomics

Metagenomics is a method of studying genetic diversity in ecosystems in which environmental samples are directly sequenced. In an exemplary method, cells such as algae in environmental samples such as seawater are separated into single cell emulsion microdroplets, and then analyzed for at least two genetic loci. For example, an investigator may be interested to find a particular species of algae that expresses a particular form of chlorophyll and belongs to a particular algal species. Genotyping by LCR is used to amplify major amplicons only algal cells from a particular species that harbor that particular form of chlorophyll. One skilled in the art can also appreciate that such a method are also useful to sample chlorophyll diversity in a particular class, species, or genus of algae by linking species-specific LCR or padlock probes with PCR amplification of chlorophyll exons. Algae and chlorophyll are only one specific example; the cells are from any species, and there are many kinds of target genetic loci, including RNA transcripts, genomic variants, and mitochondrial DNA.

Detection of DNA Methylation

DNA methylation is a type of epigenetic modifier that helps cells control RNA transcription and other cellular processes (Brunner et al., 2009 Genome Research 19:1044-56). For example, blood lymphocytes can suffer aberrant DNA methylation, leading to liquid tumors. The methods described above are useful for analyzing DNA methylation in single cells (e.g., multiple DNA methylation loci in single cells, or at least one DNA methylation locus with an RNA transcript target or DNA sequence target). DNA methylation is analyzed by methylation-specific restriction enzymes, bisulfite conversion, or precipitation with anti-methylcytosine. Most of these analyses would require multiple inputs of reaction buffers if using a microfluidic chip to create emulsion microdroplets. For example, performing bisulfite conversion requires a buffer that is inappropriate for PCR, LCR, RT-PCR, or padlock probes. In an exemplary method, single cells are encapsulated in emulsion microdroplets using a standard bisulfite conversion buffer. Then, after bisulfite conversion, the microdroplets are merged with a second aqueous buffer. This second buffer dilutes the bisulfite conversion buffer, enabling PCR, LCR, RT-PCR, or padlock probe methods. Similar approaches are useful for anti-methylcytosine or methylation sensitive restriction digestion.

Chromatin Immunoprecipitation

Chromatin immunoprecipitation is a method in which DNA is crosslinked to proteins in cell nuclei (Johnson et al., 2007 Science 316:1497-502). An antibody directed against a DNA binding protein of interest is then used to specifically precipitate DNA-protein complexes, and then the DNA is sequenced or analyzed with a DNA microarray. The molecular linkage methods described above are used to analyze multiple DNA-protein binding loci in single cells, or at least one DNA-protein binding locus with an RNA transcript target or DNA sequence target. Most of these analyses require multiple inputs of reaction buffers if using a microfluidic chip to create emulsion microdroplets. For example, performing chromatin immunoprecipitation requires a buffer that is inappropriate for PCR, LCR, RT-PCR, or padlock probes. In an exemplary method, single cells are encapsulated in emulsion microdroplets using a standard immunoprecipitation buffer. Then, after precipitation, the microdroplets are merged with a second aqueous buffer. This second buffer dilutes the precipitation buffer, enabling PCR, LCR, RT-PCR, or padlock probe methods.

While the invention has been particularly shown and described with reference to a preferred s and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE 2

| SEQ ID NO | NAME | GENOME TARGETING REGION | OVERLAP SEQUENCE | DESCRIPTION |
|---|---|---|---|---|
| SEQ ID NO: 1 | TRBV2.F | TCAAATTTCACTCTGAAGATCCGGTCCACAA | | outer forward |
| SEQ ID NO: 2 | TRBV3-1.F | GCTCACTTAAATCTTCACATCAATTCCCTGG | | outer forward |
| SEQ ID NO: 3 | TRBV4-1.F | CTTAAACCTTCACCTACACGCCCTGC | | outer forward |
| SEQ ID NO: 4 | TRBV4-2_4-3.F | CTTATTCCTTCACCTACACACCCTGC | | outer forward |
| SEQ ID NO: 5 | TRBV5-1.F | GCTCTGAGATGAATGTGAGCACCTTG | | outer forward |
| SEQ ID NO: 6 | TRBV5-3.F | GCTCTGAGATGAATGTGAGTGCCTTG | | outer forward |
| SEQ ID NO: 7 | TRBV5-4_5-5_5-6_5-7_5-8.F | GCTCTGAGCTGAATGTGAACGCCTTG | | outer forward |
| SEQ ID NO: 8 | TRBV6-1.F | TCGCTCAGGCTGGAGTCGGCTG | | outer forward |
| SEQ ID NO: 9 | TRBV6-2_6-3.F | GCTGGGGTTGGAGTCGGCTG | | outer forward |
| SEQ ID NO: 10 | TRBV6-4.F | CCCTCACGTTGGCGTCTGCTG | | outer forward |
| SEQ ID NO: 11 | TRBV6-5.F | GCTCAGGCTGCTGTCGGCTG | | outer forward |

TABLE 2-continued

INFORMAL SEQUENCE LISTING

| SEQ ID NO | NAME | GENOME TARGETING REGION | OVERLAP SEQUENCE | DESCRIPTION |
|---|---|---|---|---|
| SEQ ID NO: 12 | TRBV6-6.F | CGCTCAGGCTGGAGTTGGCTG | | outer forward |
| SEQ ID NO: 13 | TRBV6-7.F | CCCCTCAAGCTGGAGTCAGCTG | | outer forward |
| SEQ ID NO: 14 | TRBV6-8.F | CACTCAGGCTGGTGTCGGCTG | | outer forward |
| SEQ ID NO: 15 | TRBV6-9.F | CGCTCAGGCTGGAGTCAGCTG | | outer forward |
| SEQ ID NO: 16 | TRBV7-1.F | CCACTCTGAAGTTCCAGCGCACAC | | outer forward |
| SEQ ID NO: 17 | TRBV7-2.F | CACTCTGACGATCCAGCGCACAC | | outer forward |
| SEQ ID NO: 18 | TRBV7-3.F | CTCTACTCTGAAGATCCAGCGCACAG | | outer forward |
| SEQ ID NO: 19 | TRBV7-4.F | CCACTCTGAAGATCCAGCGCACAG | | outer forward |
| SEQ ID NO: 20 | TRBV7-6.F | CACTCTGACGATCCAGCGCACAG | | outer forward |
| SEQ ID NO: 21 | TRBV7-7.F | CCACTCTGACGATTCAGCGCACAG | | outer forward |
| SEQ ID NO: 22 | TRBV7-8.F | CCACTCTGAAGATCCAGCGCACAC | | outer forward |
| SEQ ID NO: 23 | TRBV7-9.F | CACCTTGGAGATCCAGCGCACAG | | outer forward |
| SEQ ID NO: 24 | TRBV9.F | GCACTCTGAACTAAACCTGAGCTCTCTG | | outer forward |
| SEQ ID NO: 25 | TRBV10-1.F | CCCCTCACTCTGGAGTCTGCTG | | outer forward |
| SEQ ID NO: 26 | TRBV10-2.F | CCCCCTCACTCTGGAGTCAGCTA | | outer forward |
| SEQ ID NO: 27 | TRBV10-3.F | CCTCCTCACTCTGGAGTCCGCTA | | outer forward |
| SEQ ID NO: 28 | TRBV11-1_11-3.F | CCACTCTCAAGATCCAGCCTGCAG | | outer forward |
| SEQ ID NO: 29 | TRBV11-2.F | CTCCACTCTCAAGATCCAGCCTGCAA | | outer forward |
| SEQ ID NO: 30 | TRBV12-3_12-4_12-5.F | CCACTCTGAAGATCCAGCCCTCAG | | outer forward |
| SEQ ID NO: 31 | TRBV13.F | CATTCTGAACTGAACATGAGCTCCTTGG | | outer forward |
| SEQ ID NO: 32 | TRBV14.F | CTACTCTGAAGGTGCAGCCTGCAG | | outer forward |
| SEQ ID NO: 33 | TRBV15.F | GATAACTTCCAATCCAGGAGGCCGAACA | | outer forward |
| SEQ ID NO: 34 | TRBV16.F | CTGTAGCCTTGAGATCCAGGCTACGA | | outer forward |
| SEQ ID NO: 35 | TRBV17.F | CTTCCACGCTGAAGATCCATCCCG | | outer forward |

TABLE 2-continued

INFORMAL SEQUENCE LISTING

| SEQ ID NO | NAME | GENOME TARGETING REGION | OVERLAP SEQUENCE | DESCRIPTION |
|---|---|---|---|---|
| SEQ ID NO: 36 | TRBV18.F | GCATCCTGAGGATCCAGCAGGTAG | | outer forward |
| SEQ ID NO: 37 | TRBV19.F | CCTCTCACTGTGACATCGGCCC | | outer forward |
| SEQ ID NO: 38 | TRBV20-1.F | CTTGTCCACTCTGACAGTGACCAGTG | | outer forward |
| SEQ ID NO: 39 | TRBV23-1.F | CAGCCTGGCAATCCTGTCCTCAG | | outer forward |
| SEQ ID NO: 40 | TRBV24-1.F | CTCCCTGTCCCTAGAGTCTGCCAT | | outer forward |
| SEQ ID NO: 41 | TRBV25-1.F | CCCTGACCCTGGAGTCTGCCA | | outer forward |
| SEQ ID NO: 42 | TRBV27.F | CCCTGATCCTGGAGTCGCCCA | | outer forward |
| SEQ ID NO: 43 | TRBV28.F | CTCCCTGATTCTGGAGTCCGCCA | | outer forward |
| SEQ ID NO: 44 | TRBV29-1.F | CTAACATTCTCAACTCTGACTGTGAGCAACA | | outer forward |
| SEQ ID NO: 45 | TRBV30.F | CGGCAGTTCATCCTGAGTTCTAAGAAGC | | outer forward |
| SEQ ID NOS 46 and 74 | TRBJ1-1.R | TTACCTACAACTGTGAGTCTGGTGCCTTGTCCAAA | GCTCATCTGGCATAATTCTCCT | inner reverse |
| SEQ ID NOS 47 and 74 | TRBJ1-2.R | ACCTACAACGGTTAACCTGGTCCCCGAACCGAA | GCTCATCTGGCATAATTCTCCT | inner reverse |
| SEQ ID NOS 48 and 74 | TRBJ1-3.R | ACCTACAACAGTGAGCCAACTTCCCTCTCCAAA | GCTCATCTGGCATAATTCTCCT | inner reverse |
| SEQ ID NOS 49 and 74 | TRBJ1-4.R | CCAAGACAGAGAGCTGGGTTCCACTGCCAAA | GCTCATCTGGCATAATTCTCCT | inner reverse |
| SEQ ID NOS 50 and 74 | TRBJ1-6.R | CTGTCACAGTGAGCCTGGTCCCGTTCCCAAA | GCTCATCTGGCATAATTCTCCT | inner reverse |
| SEQ ID NOS 51 and 74 | TRBJ2-1.R | CGGTGAGCCGTGTCCCTGGCCCGAA | GCTCATCTGGCATAATTCTCCT | inner reverse |
| SEQ ID NOS 52 and 74 | TRBJ2-2.R | CCAGTACGGTCAGCCTAGAGCCTTCTCCAAA | GCTCATCTGGCATAATTCTCCT | inner reverse |
| SEQ ID NOS 53 and 74 | TRBJ2-3.R | ACTGTCAGCCGGGTGCCTGGGCCAAA | GCTCATCTGGCATAATTCTCCT | inner reverse |
| SEQ ID NOS 54 and 74 | TRBJ2-4.R | AGAGCCGGGTCCCGGCGCCGAA | GCTCATCTGGCATAATTCTCCT | inner reverse |
| SEQ ID NOS 55 and 74 | TRBJ2-5.R | GGAGCCGCGTGCCTGGCCCGAA | GCTCATCTGGCATAATTCTCCT | inner reverse |
| SEQ ID NOS 56 and 74 | TRBJ2-6.R | GTCAGCCTGCTGCCGGCCCCGAA | GCTCATCTGGCATAATTCTCCT | inner reverse |

TABLE 2-continued

INFORMAL SEQUENCE LISTING

| SEQ ID NO | NAME | GENOME TARGETING REGION | OVERLAP SEQUENCE | DESCRIPTION |
|---|---|---|---|---|
| SEQ ID NOS 57 and 74 | TRBJ2-7.R | GTGAGCCTGGTGCCCGGCCCGAA | GCTCATCTGGC ATAATTCTCCT | inner reverse |
| SEQ ID NOS 58 and 74 | IL2.F | TCACCAGGATGCTCACATTTAAGT | AGGAGAATTAT GCCAGATGAGC | inner forward |
| SEQ ID NO: 59 and 74 | IL2.F | GAGGTTTGAGTTCTTCTTCTAGACACTGA | | outer reverse |
| SEQ ID NOS 60 and 74 | IL4.F | CCACGGACACAAGTGCGATA | AGGAGAATTAT GCCAGATGAGC | inner forward |
| SEQ ID NO: 61 and 74 | IL4.R | CCCTGCAGAAGGTTTCCTTCT | | outer reverse |
| SEQ ID NOS 62 and 75 | INFG.F | TCAGCTCTGCATCGTTTTGG | AGGAGAATTAT GCCAGATGAGC | inner forward |
| SEQ ID NO: 63 | INFG.R | GTTCCATTATCCGCTACATCTGAA | | outer reverse |
| SEQ ID NOS 64 and 75 | TNFA.F | GCCCAGGCAGTCAGATCATC | AGGAGAATTAT GCCAGATGAGC | inner forward |
| SEQ ID NO: 65 | TNFA.R | GGGTTTGCTACAACATGGGCT | | outer reverse |
| SEQ ID NOS 66 and 75 | FOXP3.F | AACAGCACATTCCCAGAGTTCCT | AGGAGAATTAT GCCAGATGAGC | inner forward |
| SEQ ID NO: 67 | FOXP3.R | CATTGAGTGTCCGCTGCTTCT | | outer reverse |
| SEQ ID NOS 68 and 75 | TBX21.F | GTCCAACAATGTGACCCAGAT | AGGAGAATTAT GCCAGATGAGC | inner forward |
| SEQ ID NO: 69 | TBX21.R | GCTGGTACTTATGGAGGGACTG | | outer reverse |
| SEQ ID NOS 70 and 75 | TBX21.F | AGCTGACTCACGCCGTCC | AGGAGAATTAT GCCAGATGAGC | inner forward |
| SEQ ID NO: 71 | TBX21.F | CACAGAAACCCTCGCACAAGCC | | outer reverse |
| SEQ ID NOS 72 and 75 | IL2.F | CTGGAATAGCCAATACTGATTACCTG | AGGAGAATTAT GCCAGATGAGC | inner forward |
| SEQ ID NO: 73 | IL2.R | CATGAATTTTATACCTTAGGAGACGG | | outer reverse |

The invention claimed is:

1. A method for creating a library of polynucleotides, comprising the steps of:
introducing multiple sets of initial probes into a plurality of compartments under conditions selected such that more than a half of the plurality of compartments contain one or less than one set of the initial probes, wherein each set of the initial probes comprises (1) an initial forward probe, wherein the initial forward probe (i) is affixed to a bead or a solid surface, and (ii) comprises a sequence complementary to a first subsequence of a first target sequence and one of at least 1,000 unique barcode sequences, and (2) an initial reverse probe, wherein the initial reverse probe comprises (i) a sequence complementary to a second subsequence of the first target sequence and (ii) a sequence complementary to a non-human, exogenous sequence;
introducing multiple sets of second probes into the plurality of compartments, wherein each set of the second probes comprises (1) a second forward probe, wherein the second forward probe comprises (i) the non-human, exogenous sequence and (ii) a sequence that is complementary to a first subsequence of a second target sequence, and (2) a second reverse probe comprising a sequence that is complementary to a second subsequence to the second target sequence;
amplifying the first target sequence using the multiple sets of the initial probes;
amplifying the second target sequence using the multiple sets of the second probes;
hybridizing the non-human exogenous sequence to its complement; and
amplifying a fused sequence comprising one of the at least 1,000 barcode sequences, the first target sequence and the second target sequence, thereby generating a library of fused polynucleotides, wherein each of the fused polynucleotides comprises one of the at least 1,000 unique barcode sequences.

2. The method of claim 1, further comprising the step of: bulk sequencing the library of fused polynucleotides.

3. The method of claim 2, further comprising the step of: separating a plurality of single cells from a population of at least 10,000 cells into the plurality of compartments.

4. The method of claim 3, further comprising the step of: identifying at least one of the plurality of compartments based on the unique barcode sequences.

5. The method of claim 3, further comprises the step of: identifying a sequence that comprises one of the unique barcode sequences; and
tracing a cell that the sequence originates from.

6. The method of claim 3, wherein the plurality of compartments comprises emulsion microdroplets.

7. The method of claim 1, wherein the first target sequence and the second target sequence are RNA molecules.

8. The method of claim 7, wherein the steps of amplifying the first target sequence and the second target sequence comprise: performing RT-PCR.

9. The method of claim 1, wherein the first target sequence and the second target sequence are DNA molecules.

10. The method of claim 9, wherein the steps of amplifying the first target sequence and the second target sequence comprise: performing a polymerase chain reaction.

11. The method of claim 9, wherein the steps of amplifying the first target sequence and the second target sequence comprise: a ligase chain reaction.

12. The method of claim 3, wherein the single cell is contained in a population of at least 25,000 cells.

13. The method of claim 12, wherein the single cell is contained in a population of at least 50,000 cells.

14. The method of claim 13, wherein the single cell is contained in a population of at least 75,000 cells.

15. The method of claim 14, wherein the single cell is contained in a population of at least 100,000 cells.

16. The method of claim 1, wherein the first target sequence and the second target sequence are human sequences.

* * * * *

SEQUENCE LISTING

<160> NUMBER OF SEQ ID NOS: 75

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tcaaatttca ctctgaagat ccggtccaca a     31

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gctcacttaa atcttcacat caattccctg g     31

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
cttaaacctt cacctacacg ccctgc     26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
cttattcctt cacctacaca ccctgc     26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gctctgagat gaatgtgagc accttg     26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
gctctgagat gaatgtgagt gccttg     26

<210> SEQ ID NO 7
<211> LENGTH: 26
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 7
gctctgagct gaatgtgaac gccttg                                         26

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcgctcaggc tggagtcggc tg                                             22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctggggttg gagtcggctg                                                20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccctcacgtt ggcgtctgct g                                              21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gctcaggctg ctgtcggctg                                                20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgctcaggct ggagttggct g                                              21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
cccctcaagc tggagtcagc tg                                        22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cactcaggct ggtgtcggct g                                         21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgctcaggct ggagtcagct g                                         21

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccactctgaa gttccagcgc acac                                      24

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cactctgacg atccagcgca cac                                       23

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctctactctg aagatccagc gcacag                                    26

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccactctgaa gatccagcgc acag								24

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cactctgacg atccagcgca cag								23

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccactctgac gattcagcgc acag								24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccactctgaa gatccagcgc acac								24

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caccttggag atccagcgca cag								23

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcactctgaa ctaaacctga gctctctg								28

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 25
cccctcactc tggagtctgc tg                                              22

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26 cccctcact ctggagtcag cta                                              23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cctcctcact ctggagtccg cta                                             23

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccactctcaa gatccagcct gcag                                            24

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctccactctc aagatccagc ctgcaa                                          26

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccactctgaa gatccagccc tcag                                            24

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
```

```
cattctgaac tgaacatgag ctccttgg                                          28
```

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
ctactctgaa ggtgcagcct gcag                                              24
```

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
gataacttcc aatccaggag gccgaaca                                          28
```

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

```
ctgtagcctt gagatccagg ctacga                                            26
```

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

```
cttccacgct gaagatccat cccg                                              24
```

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

```
gcatcctgag gatccagcag gtag                                              24
```

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
cctctcactg tgacatcggc cc                                              22
```

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

```
cttgtccact ctgacagtga ccagtg                                          26
```

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
cagcctggca atcctgtcct cag                                             23
```

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
ctccctgtcc ctagagtctg ccat                                            24
```

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
ccctgaccct ggagtctgcc a                                               21
```

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
ccctgatcct ggagtcgccc a                                               21
```

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
ctccctgatt ctggagtccg cca                                             23
```

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctaacattct caactctgac tgtgagcaac a                                    31

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cggcagttca tcctgagttc taagaagc                                        28

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ttacctacaa ctgtgagtct ggtgccttgt ccaaa                                35

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acctacaacg gttaacctgg tccccgaacc gaa                                  33

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acctacaaca gtgagccaac ttccctctcc aaa                                  33

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccaagacaga gagctgggtt ccactgccaa a                                    31

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctgtcacagt gagcctggtc ccgttcccaa a                              31

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cggtgagccg tgtccctggc ccgaa                                     25

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ccagtacggt cagcctagag ccttctccaa a                              31

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
actgtcagcc gggtgcctgg gccaaa                                    26

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
agagccgggt cccggcgccg aa                                        22

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggagccgcgt gcctggcccg aa                                        22

```
<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gtcagcctgc tgccggcccc gaa                                            23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtgagcctgg tgcccggccc gaa                                            23

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tcaccaggat gctcacattt aagt                                           24

<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gaggtttgag ttcttcttct agacactga                                      29

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ccacggacac aagtgcgata                                                20

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccctgcagaa ggtttccttc t                                              21

<210> SEQ ID NO 62
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tcagctctgc atcgttttgg                                              20

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gttccattat ccgctacatc tgaa                                         24

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcccaggcag tcagatcatc                                              20

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gggtttgcta caacatgggc t                                            21

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
aacagcacat tcccagagtt cct                                          23

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cattgagtgt ccgctgcttc t                                            21

<210> SEQ ID NO 68
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gtccaacaat gtgacccaga t                                              21

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gctggtactt atggagggac tg                                             22

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
agctgactca cgccgtcc                                                  18

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cacagaaacc ctcgcacaag cc                                             22

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ctggaatagc caatactgat tacctg                                         26

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
catgaatttt ataccttagg agacgg                                         26

<210> SEQ ID NO 74
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 74
gctcatctgg cataattctc ct                                                  22

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
aggagaatta tgccagatga gc                                                  22
```